United States Patent
Mitchell et al.

(10) Patent No.: US 11,225,667 B2
(45) Date of Patent: Jan. 18, 2022

(54) **MULTI-COPY STRATEGY FOR HIGH-TITER AND HIGH-PURITY PRODUCTION OF MULTI-SUBUNIT PROTEINS SUCH AS ANTIBODIES IN TRANSFORMED MICROBES SUCH AS *PICHIA PASTORIS***

(71) Applicant: ALDERBIO HOLDINGS LLC, Las Vegas, NV (US)

(72) Inventors: Danielle Marie Mitchell, Seattle, WA (US); Leon F. Garcia-Martinez, Woodinville, WA (US); Patricia Dianne McNeill, Federal Way, WA (US); Ethan Wayne Ojala, Snohomish, WA (US); Mehmet Inan, Antalya (TR); John Latham, Seattle, WA (US)

(73) Assignee: H. LUNDBECK A/S, Valby (DK)

( * ) Notice: Subject to any disclaimer, the term of this patent is extended or adjusted under 35 U.S.C. 154(b) by 83 days.

(21) Appl. No.: 16/172,965

(22) Filed: Oct. 29, 2018

(65) Prior Publication Data

US 2019/0119692 A1    Apr. 25, 2019

Related U.S. Application Data

(60) Division of application No. 13/589,584, filed on Aug. 20, 2012, now Pat. No. 10,150,968, which is a continuation-in-part of application No. 13/466,795, filed on May 8, 2012.

(60) Provisional application No. 61/525,307, filed on Aug. 19, 2011.

(51) Int. Cl.
| | |
|---|---|
| *C12N 1/16* | (2006.01) |
| *C07K 16/00* | (2006.01) |
| *C12N 15/00* | (2006.01) |
| *C12N 15/81* | (2006.01) |
| *C12P 21/00* | (2006.01) |
| *C12P 21/02* | (2006.01) |

(52) U.S. Cl.
CPC .......... *C12N 15/815* (2013.01); *C07K 16/00* (2013.01); *C12N 1/16* (2013.01); *C12P 21/005* (2013.01); *C12P 21/02* (2013.01); *C07K 2317/14* (2013.01); *C07K 2319/036* (2013.01); *C07K 2319/50* (2013.01)

(58) Field of Classification Search
CPC ...... C12N 1/16; C12N 15/00; C07K 2317/14; C07K 16/00; C07K 2317/41
See application file for complete search history.

(56) References Cited

U.S. PATENT DOCUMENTS

| | | | |
|---|---|---|---|
| 7,319,139 B2 | 1/2008 | Braslawsky et al. | |
| 7,560,249 B2 | 7/2009 | Van De Laar et al. | |
| 7,927,863 B2 | 4/2011 | Cregg et al. | |
| 7,935,340 B2 | 5/2011 | Garcia-Martinez et al. | |
| 8,222,386 B2 | 7/2012 | Cregg et al. | |
| 8,268,582 B2 | 9/2012 | Cregg et al. | |
| 8,785,613 B2 | 7/2014 | Cregg et al. | |
| 9,765,321 B2 | 9/2017 | Cregg et al. | |
| 9,873,746 B2 | 1/2018 | Cregg et al. | |
| 10,155,819 B2 | 12/2018 | Cregg et al. | |
| 10,259,883 B2 | 4/2019 | Cregg et al. | |
| 2001/0036647 A1 | 11/2001 | Choudary et al. | |
| 2003/0027213 A1 | 2/2003 | Zhu et al. | |
| 2003/0157641 A1 | 8/2003 | Reff et al. | |
| 2004/0077069 A1 | 4/2004 | Van De Laar et al. | |
| 2006/0270045 A1 | 11/2006 | Cregg et al. | |
| 2008/0108513 A1 | 5/2008 | Pannier et al. | |
| 2009/0022658 A1 | 1/2009 | Braslawsky et al. | |
| 2009/0028784 A1 | 1/2009 | Garcia-Martinez et al. | |
| 2011/0020222 A1 | 1/2011 | Braslawsky et al. | |
| 2020/0031949 A1 | 1/2020 | Cregg et al. | |

FOREIGN PATENT DOCUMENTS

| | | |
|---|---|---|
| JP | 2007-508847 | 4/2007 |
| WO | WO 2000/056903 | 9/2000 |
| WO | WO 2002/048382 | 6/2002 |
| WO | 2002060955 | 8/2002 |
| WO | 2002096948 | 12/2002 |
| WO | WO 03/048306 | 6/2003 |
| WO | WO 2005-040395 | 6/2005 |
| WO | WO 2008/063302 | 5/2008 |
| WO | WO 2012/075340 | 6/2012 |

OTHER PUBLICATIONS

Sreekrishna, K., et al., "High-level expression, purification, and characterization of recombinant human tumor necrosis factor synthesized in the methylotrophic yeast *Pichia pastoris*," Biochemistry. May 2, 1989;28(9):4117-25.

Romanos, M., et al., "Foreign Gene Expression in Yeast: a Review," Yeast Jun. 1992; 8(6):423-88.

Romanos, M., et al., "Expression of tetanus toxin fragment C in yeast: gene synthesis is required to eliminate fortuitous polyadenylation sites in AT-rich DNA," Nucleic Acids Res. Apr. 11, 1991; 19(7):1461-67.

Krogh, B., et al., "Recombination Proteins in Yeast," Annu. Rev Genet. 2004;38:233-271.

Clare J.J., et al., "High-level expression of tetanus toxin fragment C in Pichia pastoris strains containing multiple tandem integrations of the gene," Biotechnology (NY). May 1991;9(5):455-60.

Macauley-Patrick, S., et al., "Heterologous protein production using the Pichia pastoris expression system," Yeast Mar. 2005;22(4):249-70.

(Continued)

*Primary Examiner* — Daniel E Kolker
*Assistant Examiner* — Aditi Dutt
(74) *Attorney, Agent, or Firm* — Robin L. Teskin; Baker, Donelson, Bearman, Caldwell & Berkowitz PC

(57) ABSTRACT

Methods for producing heterologous multi-subunit proteins in transformed cells are disclosed. In particular, the present disclosure provides improved methods of producing multi-subunit proteins, including antibodies and other multi-subunit proteins, which may or may not be secreted, with a higher yield and decreased production of undesired side-products. In exemplary embodiments, the transformed cells are a yeast, e.g., methylotrophic yeast such as *Pichia pastoris*.

9 Claims, 53 Drawing Sheets

Specification includes a Sequence Listing.

(56) References Cited

OTHER PUBLICATIONS

Simmons, L.C., et al., "Expression of full-length immunoglobulins in *Escherichia coli*: rapid and efficient production of aglycosylated antibodies," J Immunol Methods May 1, 2002;263(1-2):133-47.

Baumann K., et al., "Hypoxic fed-batch cultivation of Pichia pastoris increases specific and volumetric productivity of recombinant proteins," Biotechnol Bioeng. May 1, 2008;100(1)177-83.

Bier M., et al., "How yeast cells synchronize their glycolytic oscillations: a perturbation analytic treatment," Biophys J. Mar. 2000;78(3):1087-93.

Chusainow J., et al., "A study of monoclonal antibody-producing CHO cell lines: what makes a stable high producer?" Biotechnol Bioeng. Mar. 1, 2009;102(4)1182-96.

David ET., et al., "Studies on the effect of ethanol on eukaryotic protein synthesis in vitro," J Biol Chem. Jun. 25, 1983;258(12):7702-6.

Gasser B., et al., "Engineering of Pichia pastoris for improved production of antibody fragments," Biotechnol Bioeng. Jun. 5, 2006;94(2):353-61.

Görgens JF., et al., "Amino acid supplementation improves heterologous protein production by *Saccaromyces cerevisiae* in defined medium," Appl Microbiol Biotechnol. Jun. 2005;67(5):684-91.

Inan M., et al., "Enhancement of protein secretion in Pichia pastoris by overexpression of protein disulfide isomerase," Biotechnol Bioeng. Mar. 5, 2006;93(4):771-8.

Inan M., et al., "The effect of ethanol and acetate on protein expression in Pichia pastoris," J Biosci Bioeng. 2001;92(4)337-41.

Jiang Z., et al., "Regulation of recombinant monoclonal antibody production in chinese hamster ovary cells; a comparative study of gene copy number, mRNA level, and protein expression," Biotechnol Prog. Jan.-Feb. 2006;22(1):313-8.

Li Z., et al., "An improved method for enhanced production and biological activity of human secretory leukocyte protease inhibitor (SLPI) in Pichia pastoris," Biochem Biophys Res commun. Nov. 19, 2010;402(3):519-24.

Mühlbauer E., et al., "Impaired immunoglobulin M production by incubation of hybridoma cells with ethanol," Alcohol. Jul. 2001;24(3):179-87.

Reisinger H., et al., "The absence of effect of gene copy number and mRNA level on the amount of mAb secretion from mammalian cells," Appl Microbiol Biotechnol. Dec. 2008;81(4):701-10.

Tapani E., et al., "Toxicity of ethanol in low concentrations. Experimental evaluation in cell culture," Acta Radiol. Nov. 1996;37(6):923-6.

van de Laar T., et al., "Increased heterologous protein production by *Saccharomyces cerevisiae* growing on ethanol as sole carbon source," Biotechnol Bioeng. Feb. 15, 2007;96(3):483-94.

Weaver-Feldhaus JM., et al., "Yeast mating for combinatorial Fab library generation and surface display," FEBS Lett. Apr. 23, 2004:564(1-2):24-34.

Schlatter S., et al., "On the optimal ratio of heavy to light chain genes for efficient recombinant antibody production by CHO cells," Biotechnol Prog. Jan.-Feb. 2005;21(1):122-33.

Goel A., et al., "Divalent forms of CC49 single-chain antibody constructs in Pichia pastoris: expression, purification, and characterization," J Biochem. May 2000;127(5):829-36.

Hellwig S., et al., "Analysis of single-chain antibody production in Pichia pastoris using online methanol control in fed-batch and mixed-feed fermentations," Biotechnol Bioeng. Aug. 20, 2001;74(4):344-52.

Saliola M., et al., "Use of the KlADH4 promoter for ethanol-dependent production of recombinant human serum albumin in Kluyveromyces lactis," Appl Environ Microbiol. Jan. 1999;65(1):53-60.

Li H, et al. "Optimization of humanized IgGs in glycoengineered Pichia pastoris," Nat Biotechnol. Feb. 2006;24(2):210-5.

Agilent Technologies: Recombinant protein characterization: pp. 1-36, Aug. 8, 2011.

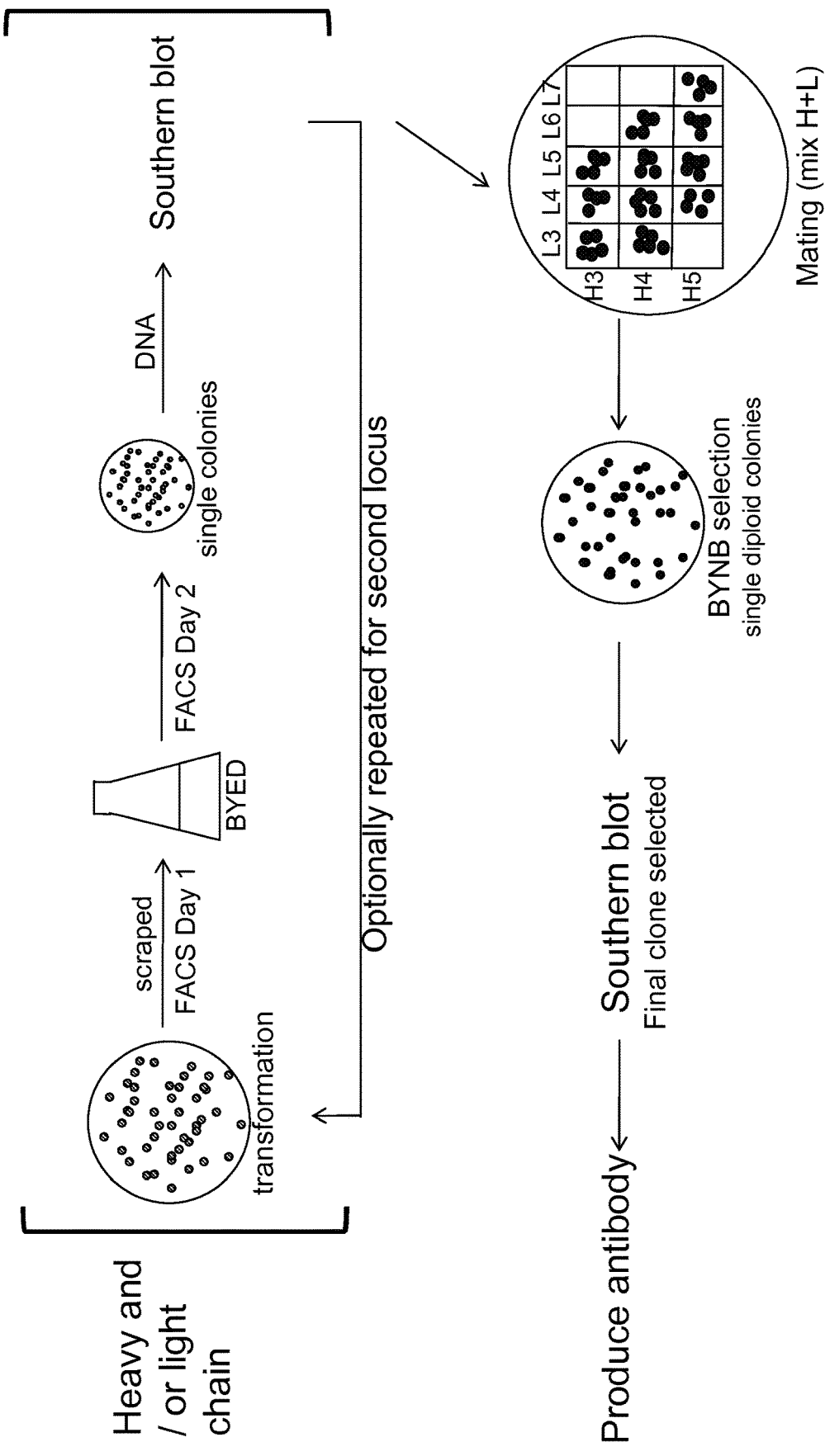
Fig. 1. Overview of methodology

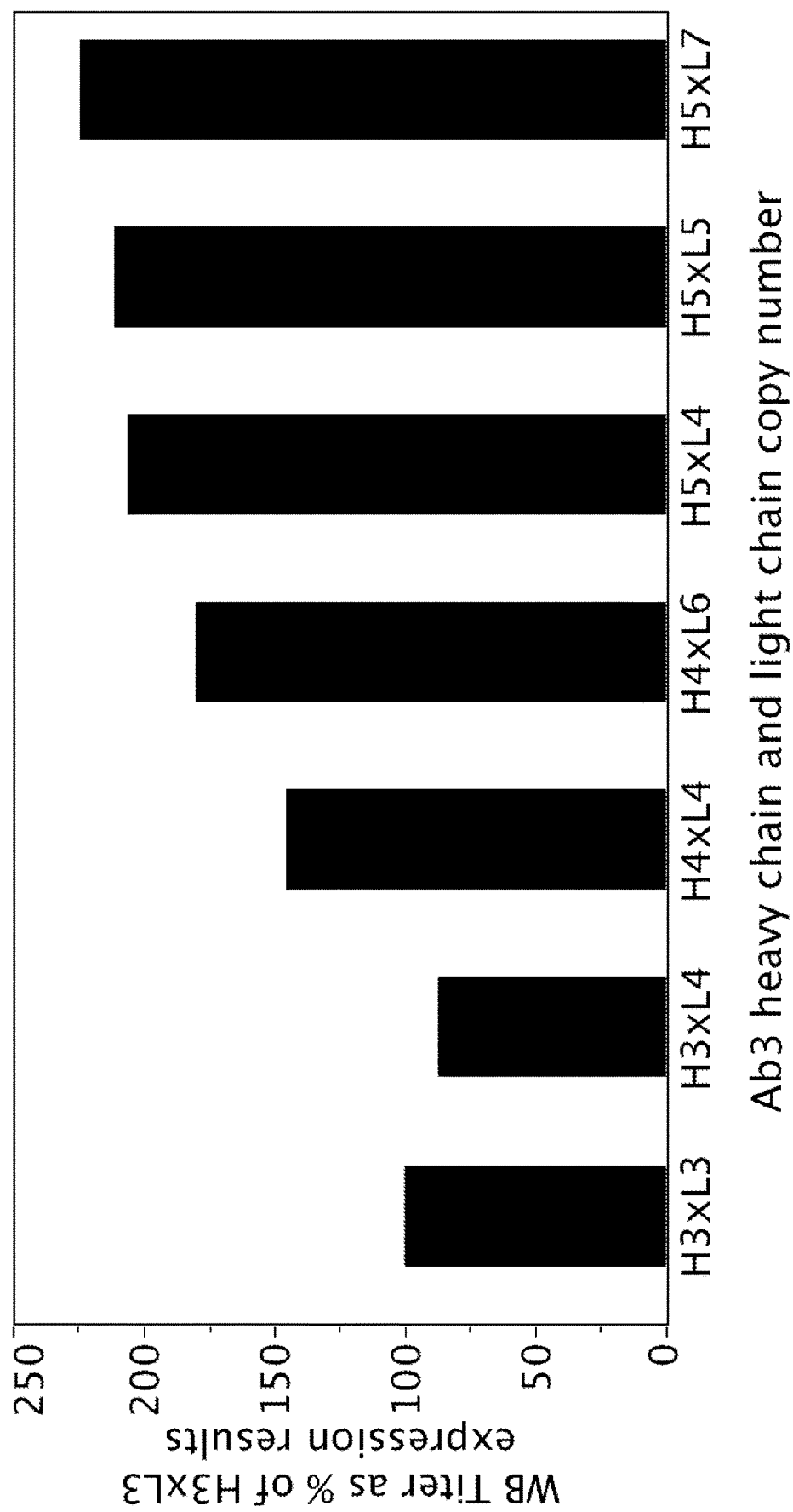

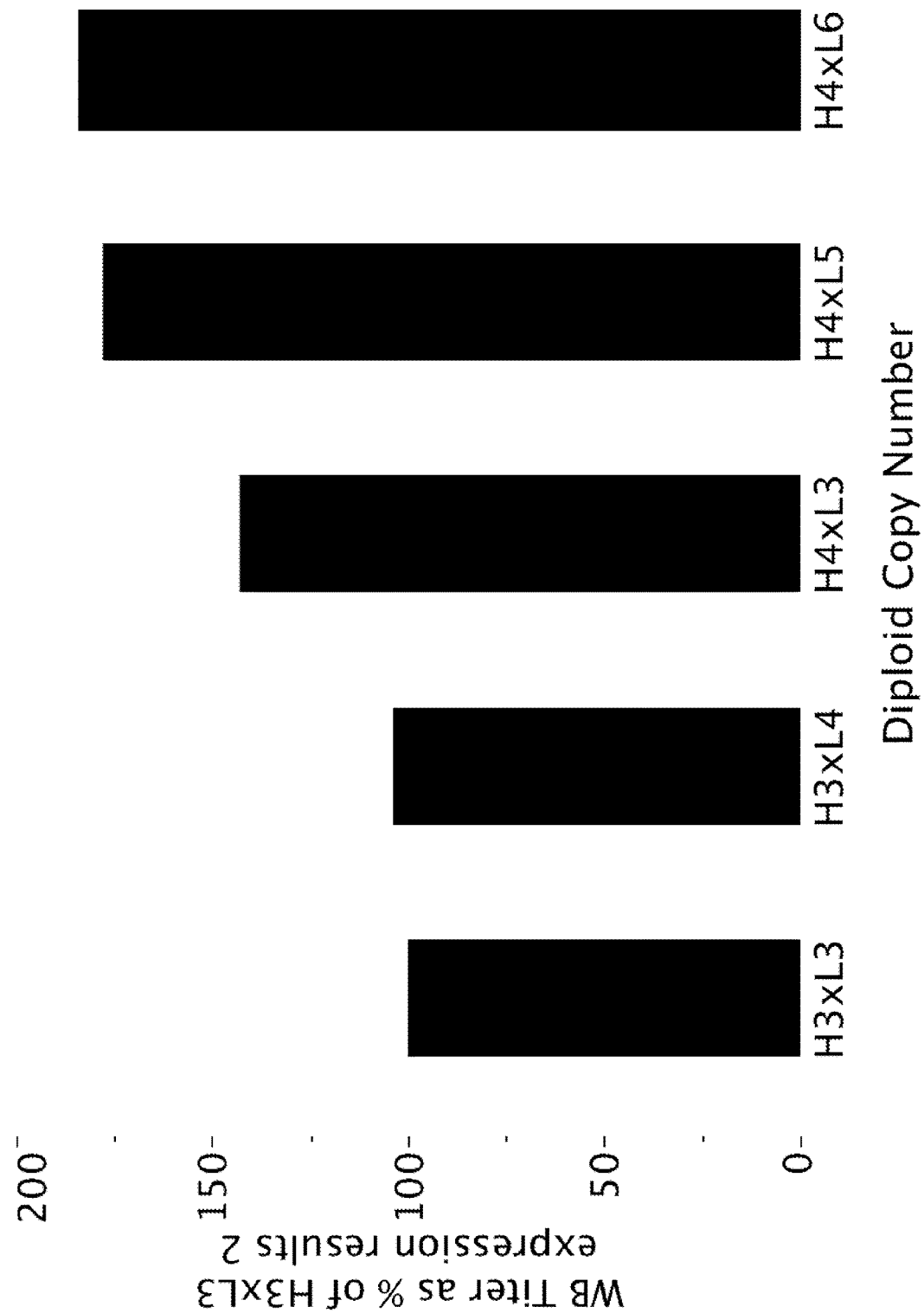

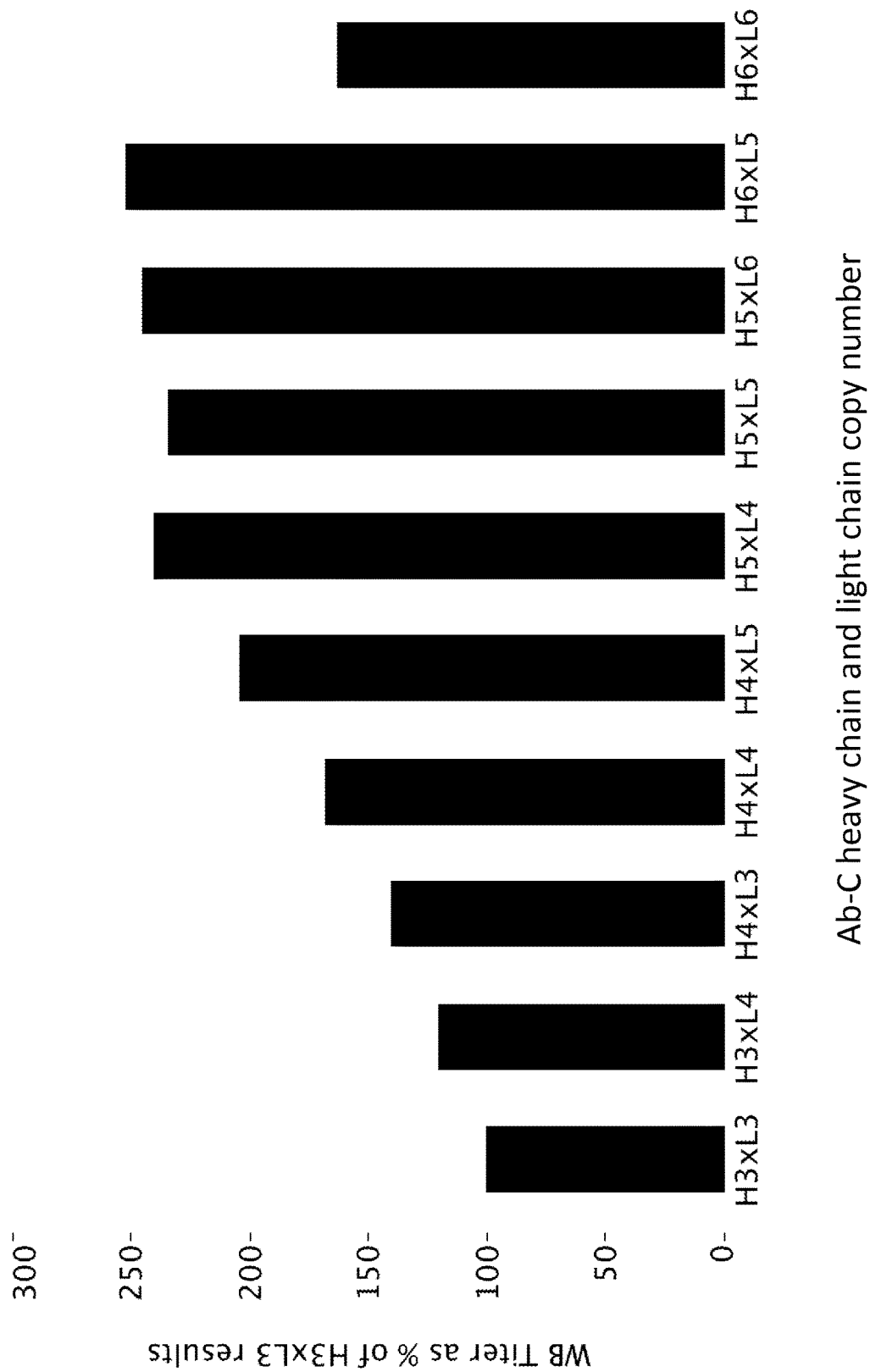
FIG. 4. Ab-C Yield

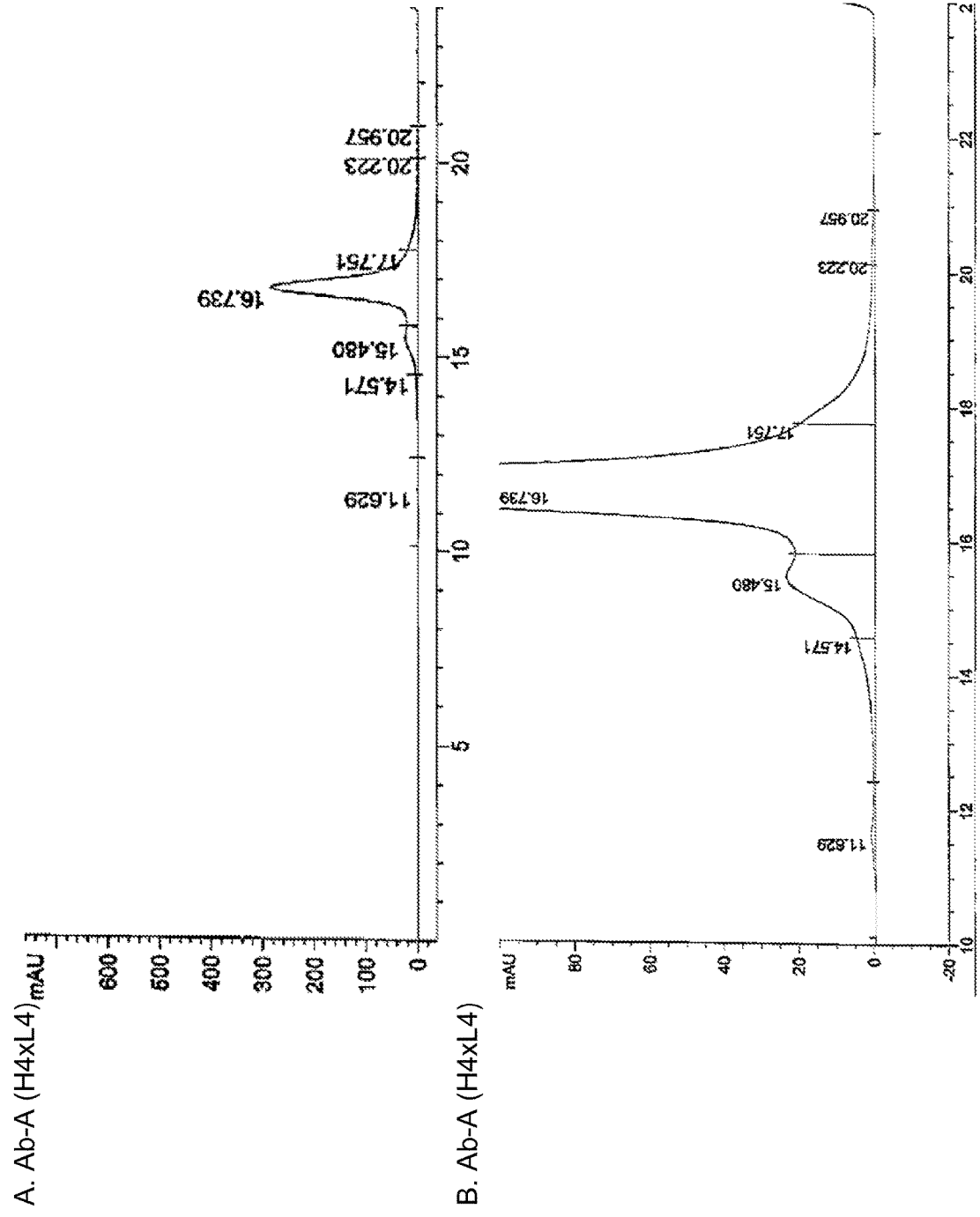
FIG. 5. Ab-A Purity by HPLC

| Retention time | Ab-A-H4xL4<br>% of total signal | Ab-A-H4xL6<br>% of total signal |
|---|---|---|
| 0 to 14.6 min | 2.07 | 3.24 |
| 15.5 | 8.81 | 1.58 |
| 16.7 | 83.71 | 86.97 |
| 18 to 22 min | 5.42 | 8.19 |

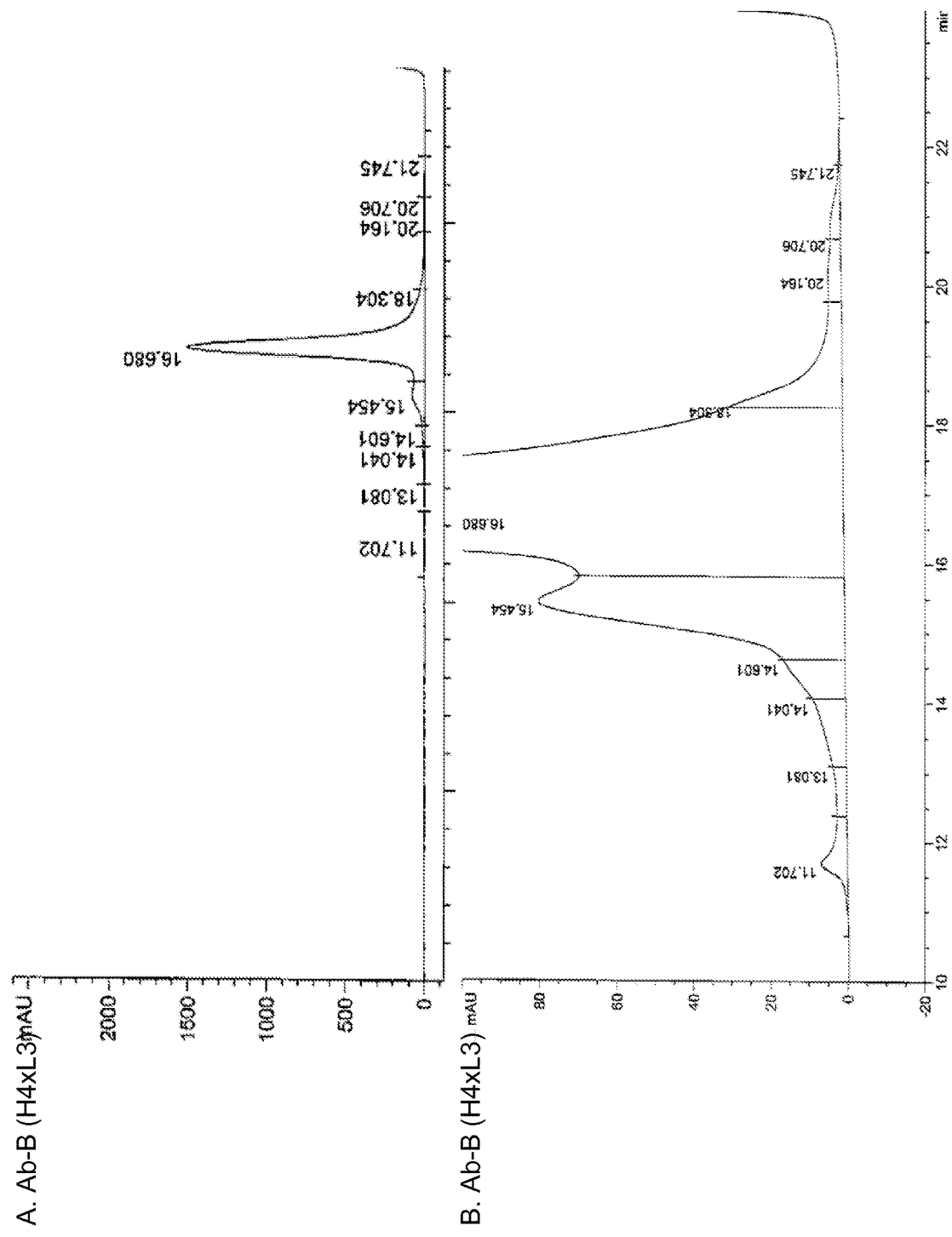

| Retention time | Ab-B-H4xL3<br>% of total signal | Ab-B-H4xL5<br>% of total signal |
|---|---|---|
| 0 to 14.6 min | 1.82 | 1.83 |
| 15.5 | 6.26 | 2.54 |
| 16.7 | 90.05 | 92.18 |
| 18 to 22 min | 1.87 | 3.46 |

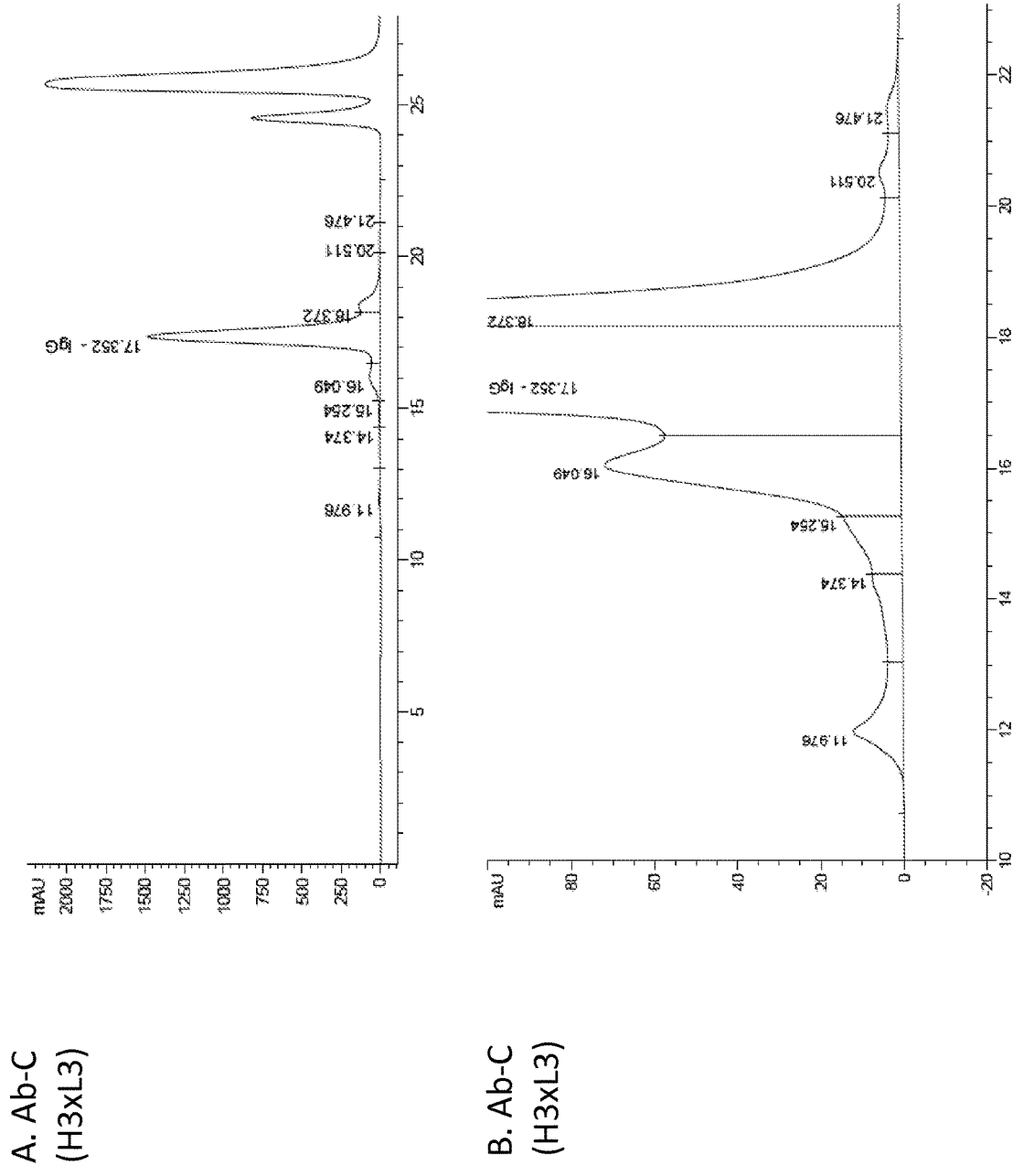
FIG. 7. Ab-C Purity by HPLC
A. Ab-C (H3xL3)
B. Ab-C (H3xL3)

| Retention Time | Ab-C-H3xL3<br>% of Total Signal | Ab-C-H5xL5<br>% of Total Signal |
|---|---|---|
| 0 to 14.4 min | 1.54 | 1.92 |
| 15.2 to 16.1 min | 6.55 | 4.00 |
| 17.4 min | 83.48 | 72.16 |
| 18 to 22 min | 0.52 | 21.92 |

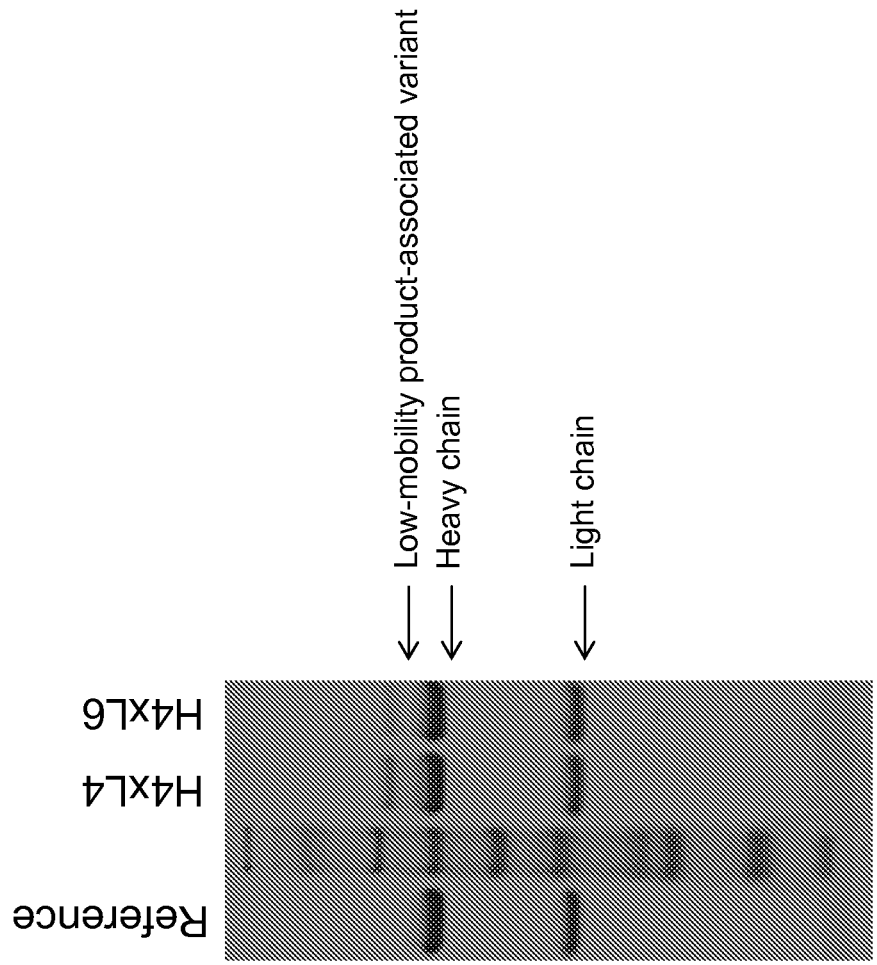
FIG. 8. Ab-A Purity

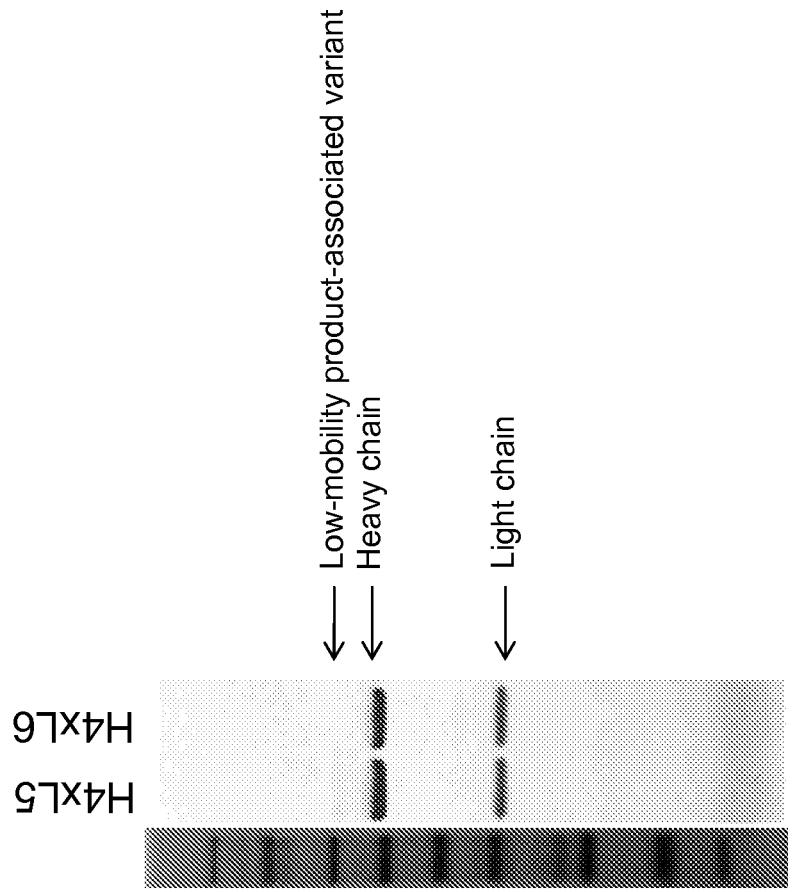
FIG. 9. Ab-B Purity

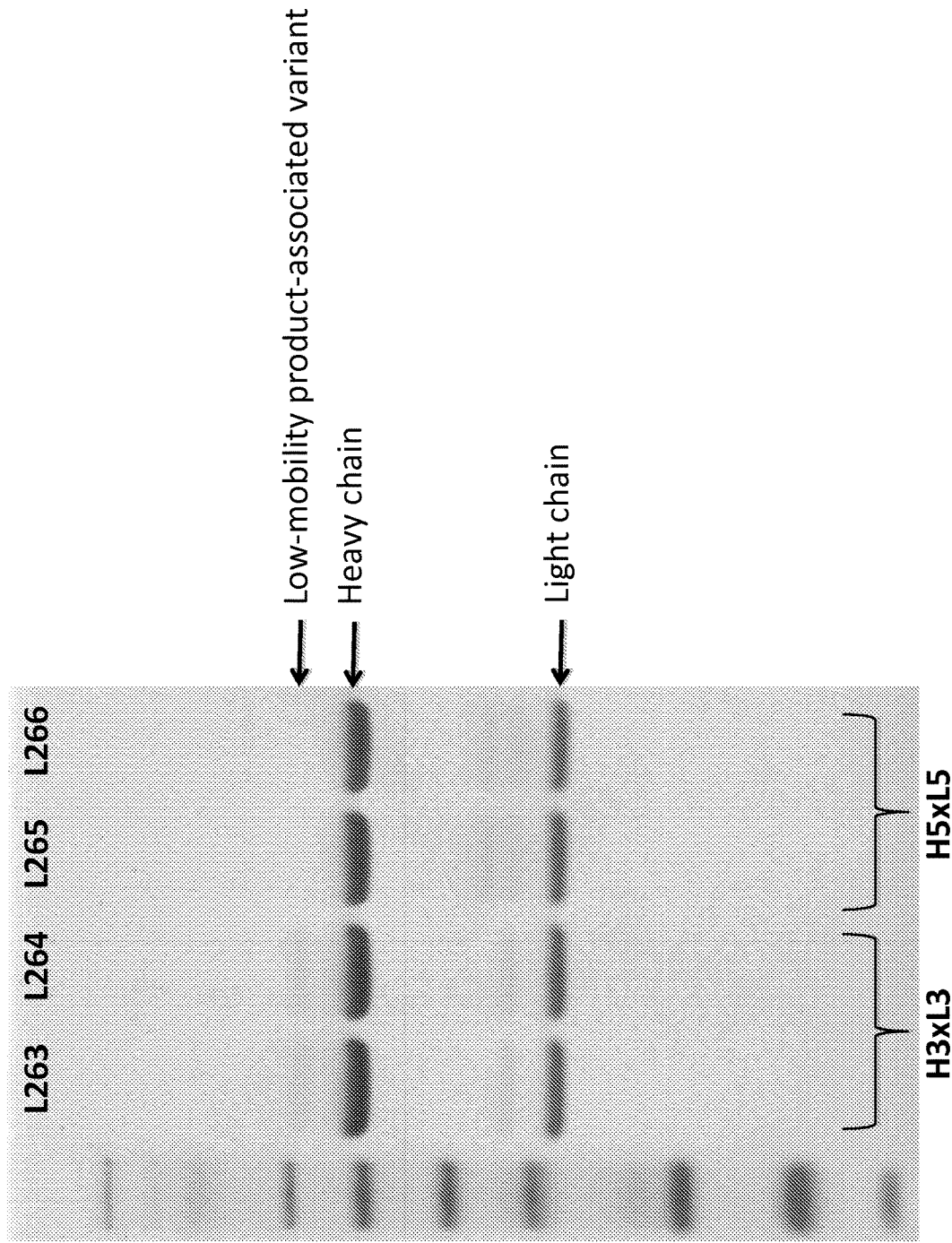
FIG. 10. Ab-C Purity

FIG. 11. Identity of Ab-B species: Low-mobility impurity is related to human Fc and is glycosylated.
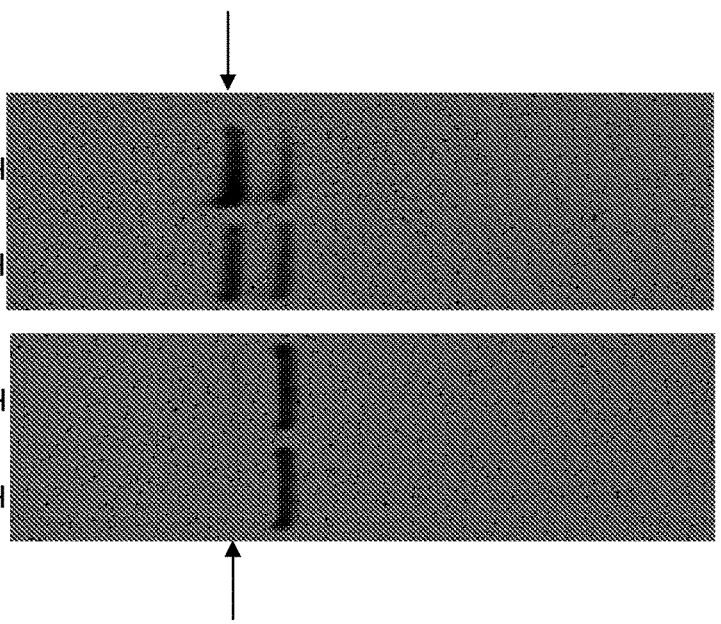
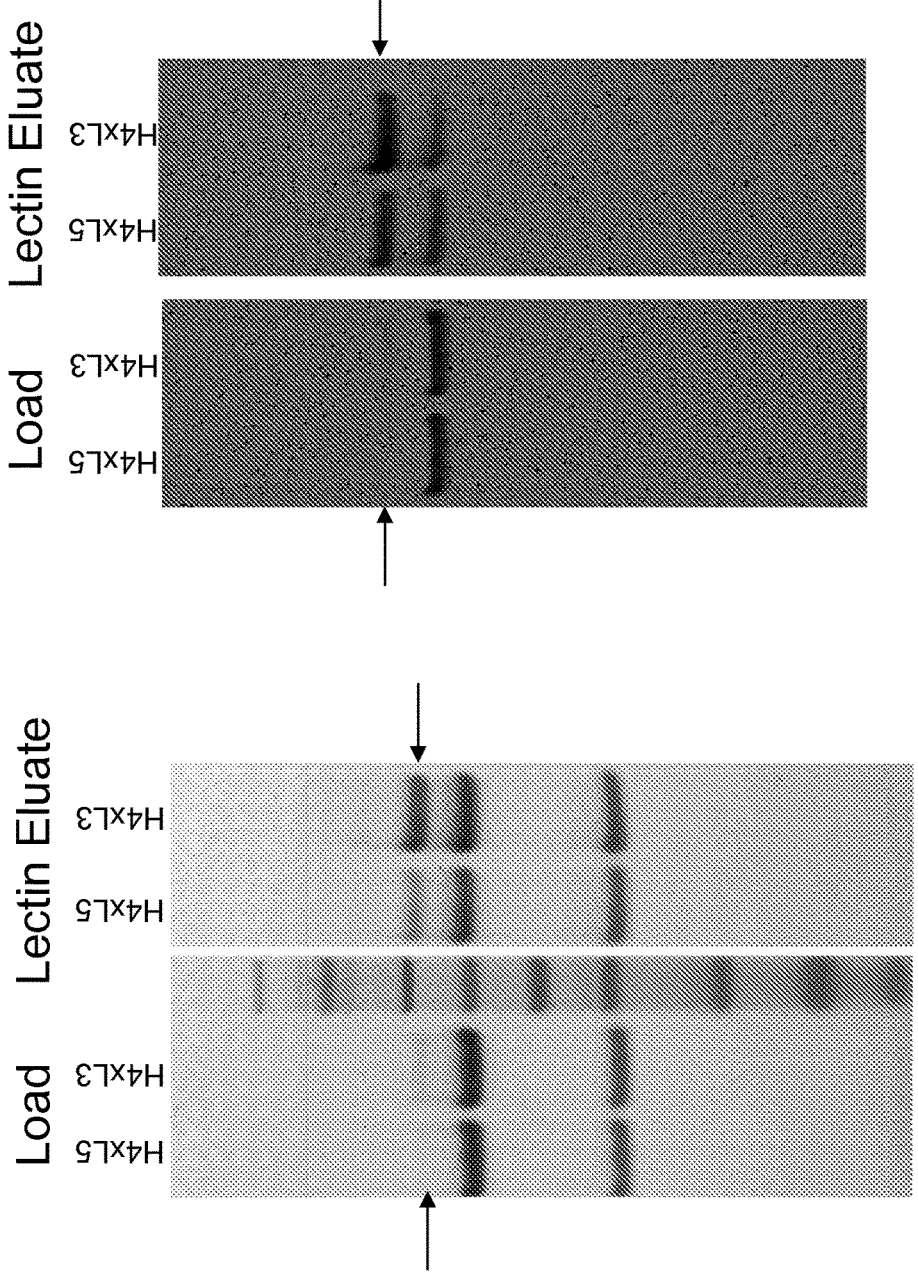

A. Ab-B H4xL3, load

B. Ab-B H4xL3, load

C. Ab-B
H4xL3, lectin eluate

D. Ab-B
H4xL3, lectin eluate

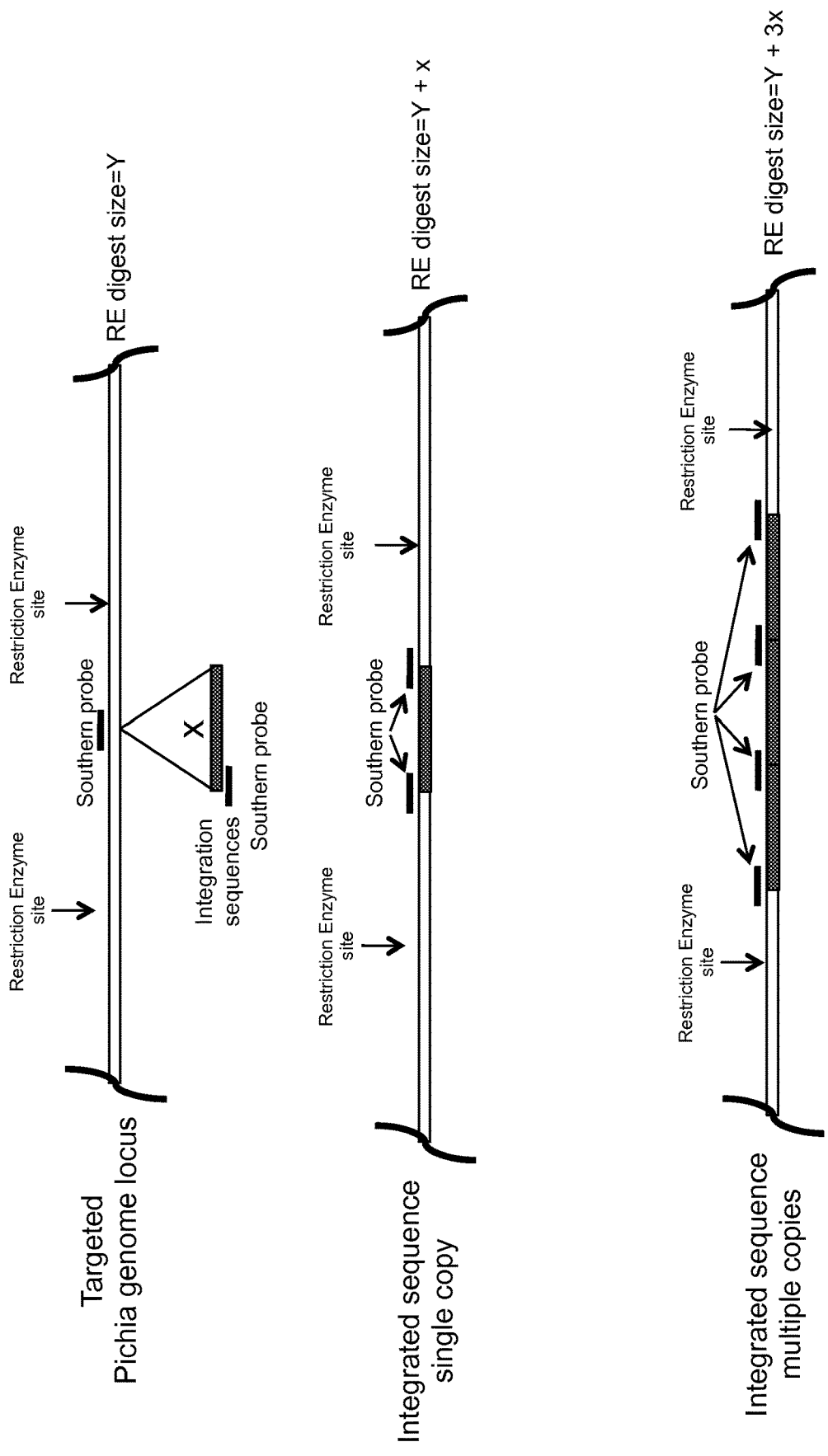
FIG. 22. Molecular Biology Overview Single Locus

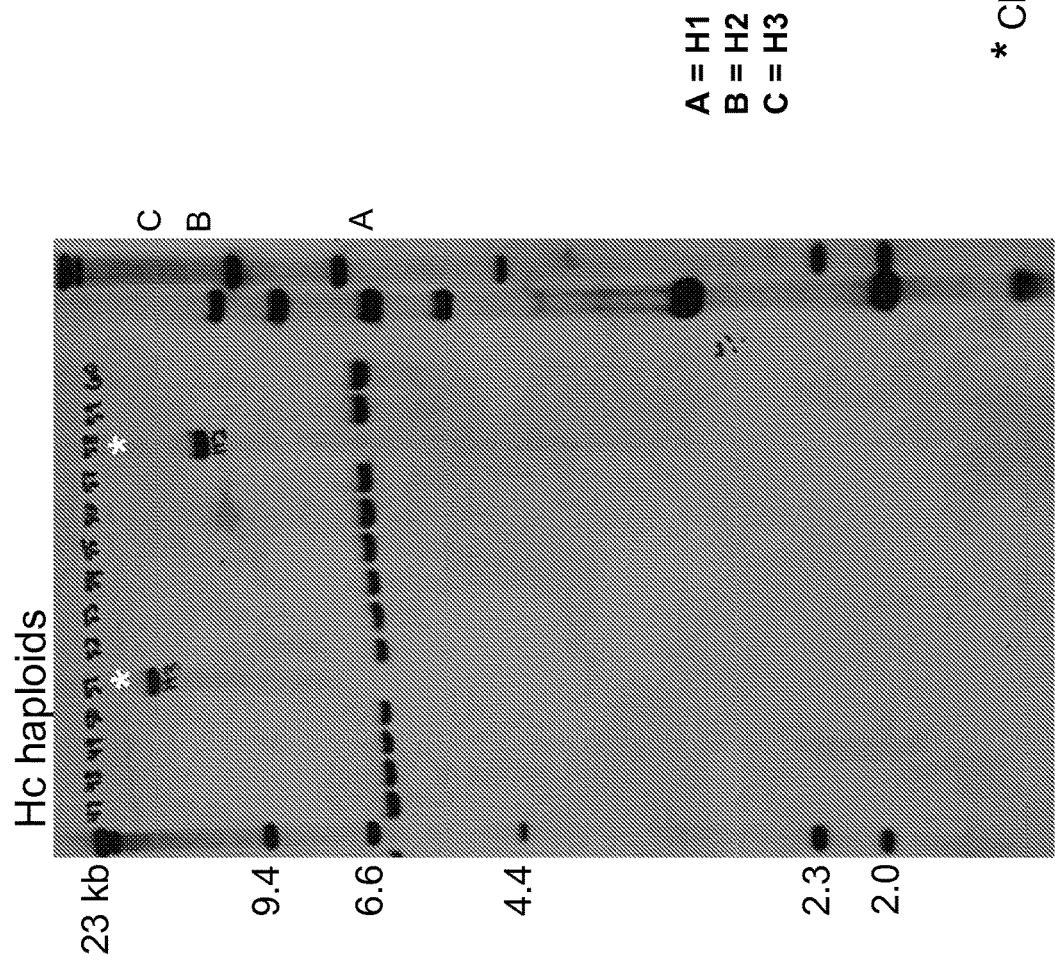
FIG. 23. Ab-A – Haploid Southern (pGAP locus)

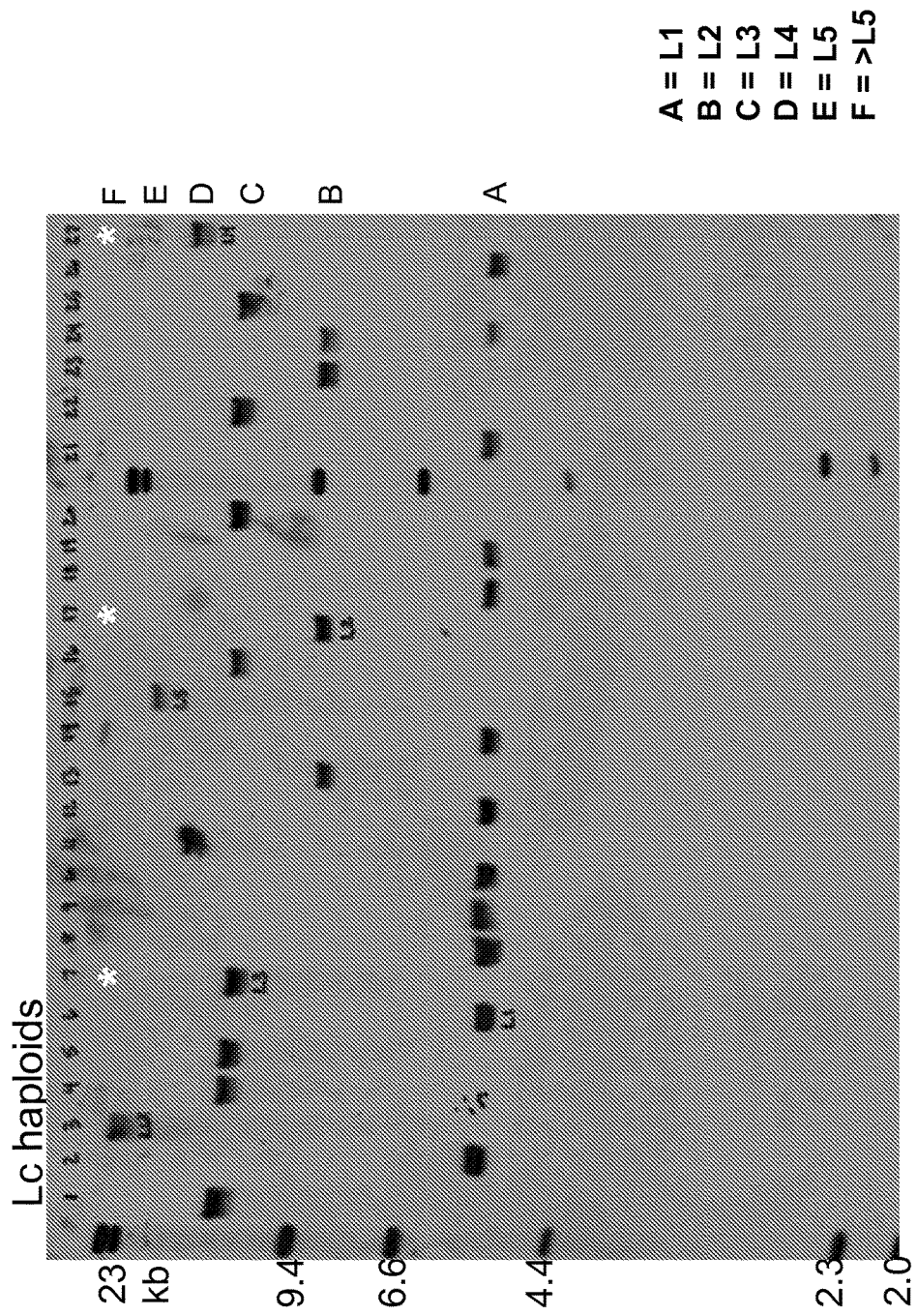
FIG. 24. Ab-A – Haploid Southern (pGAP locus)

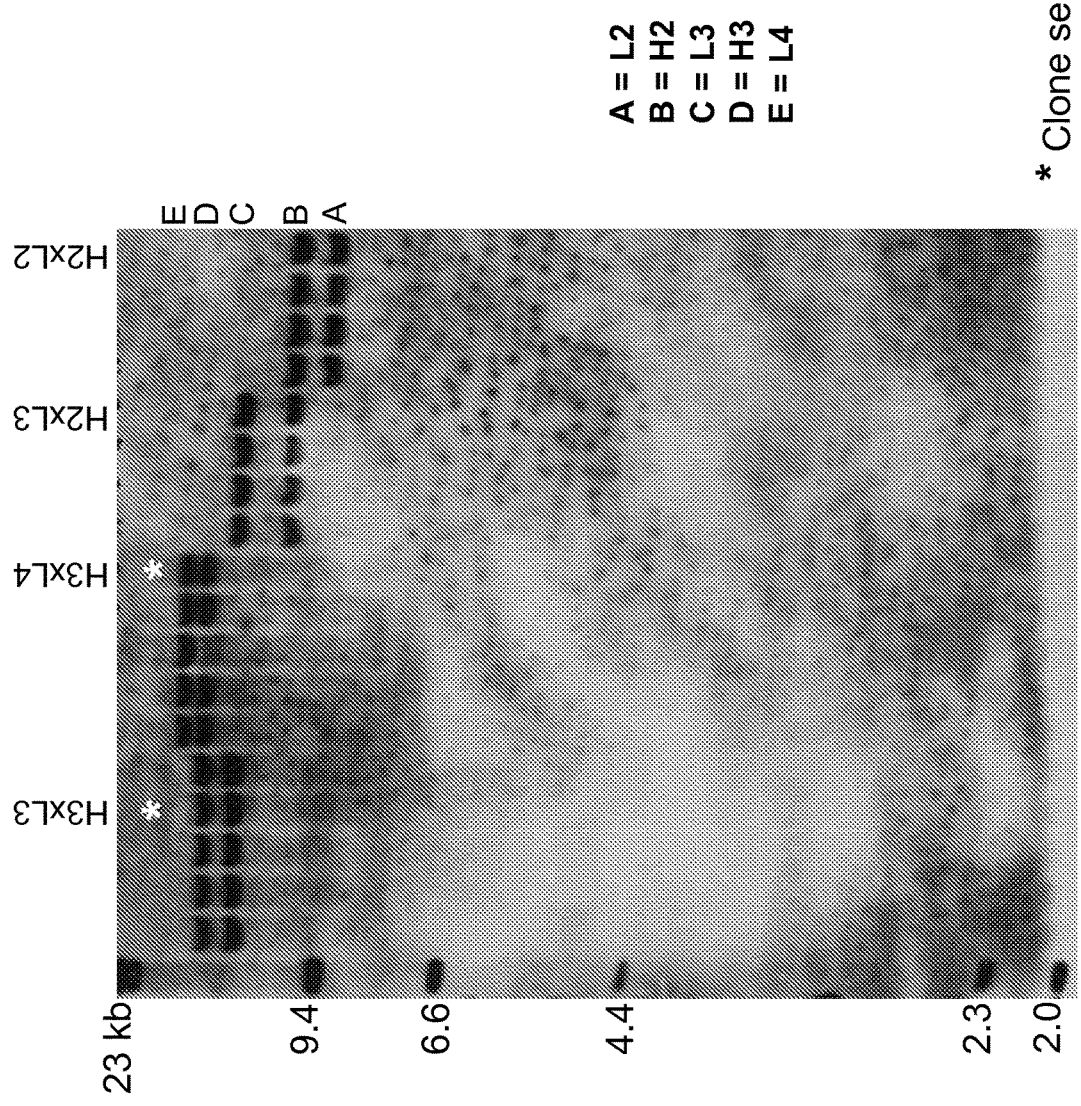
FIG. 25. Ab-A – Diploid Southern (pGAP locus)

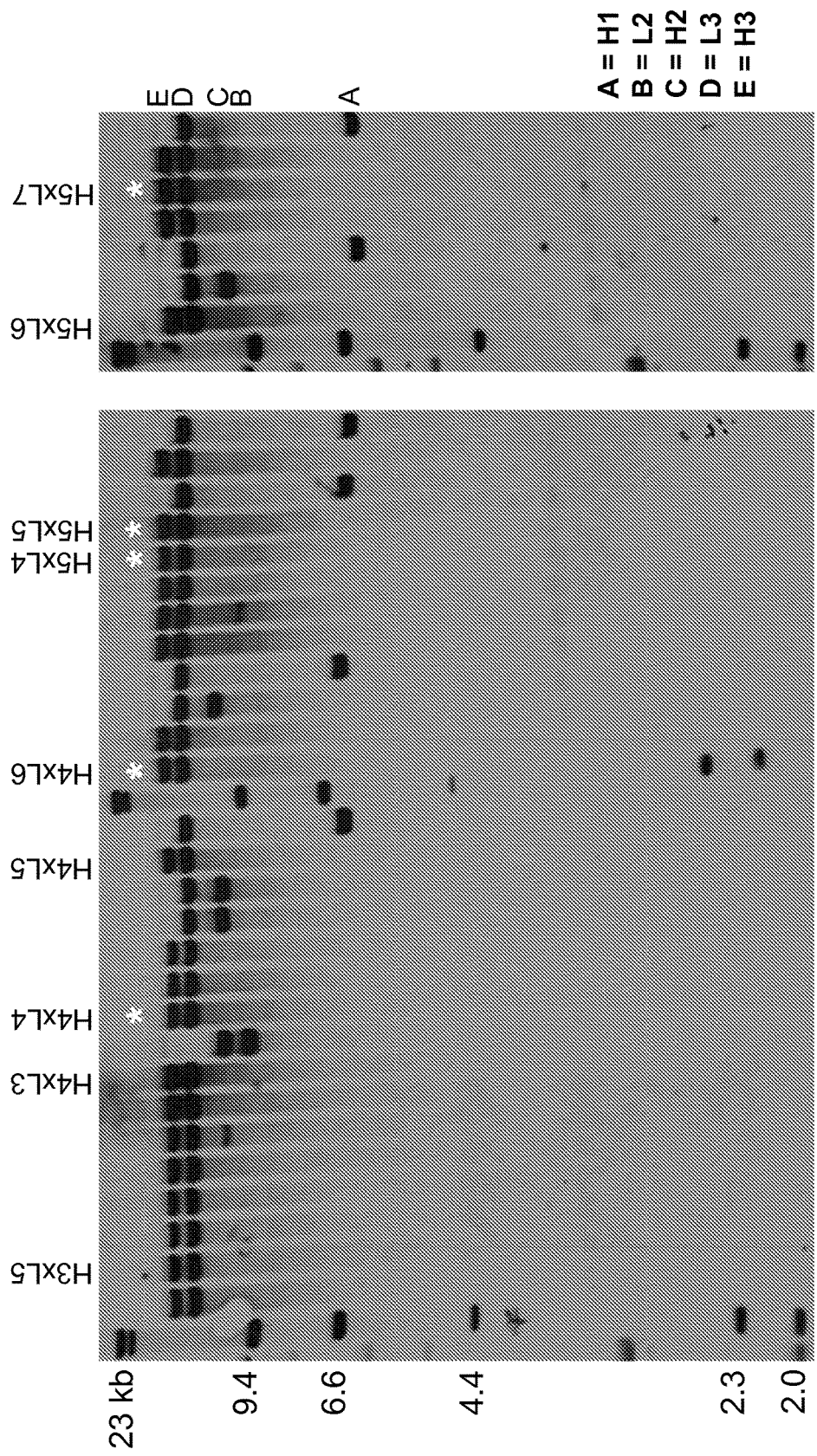

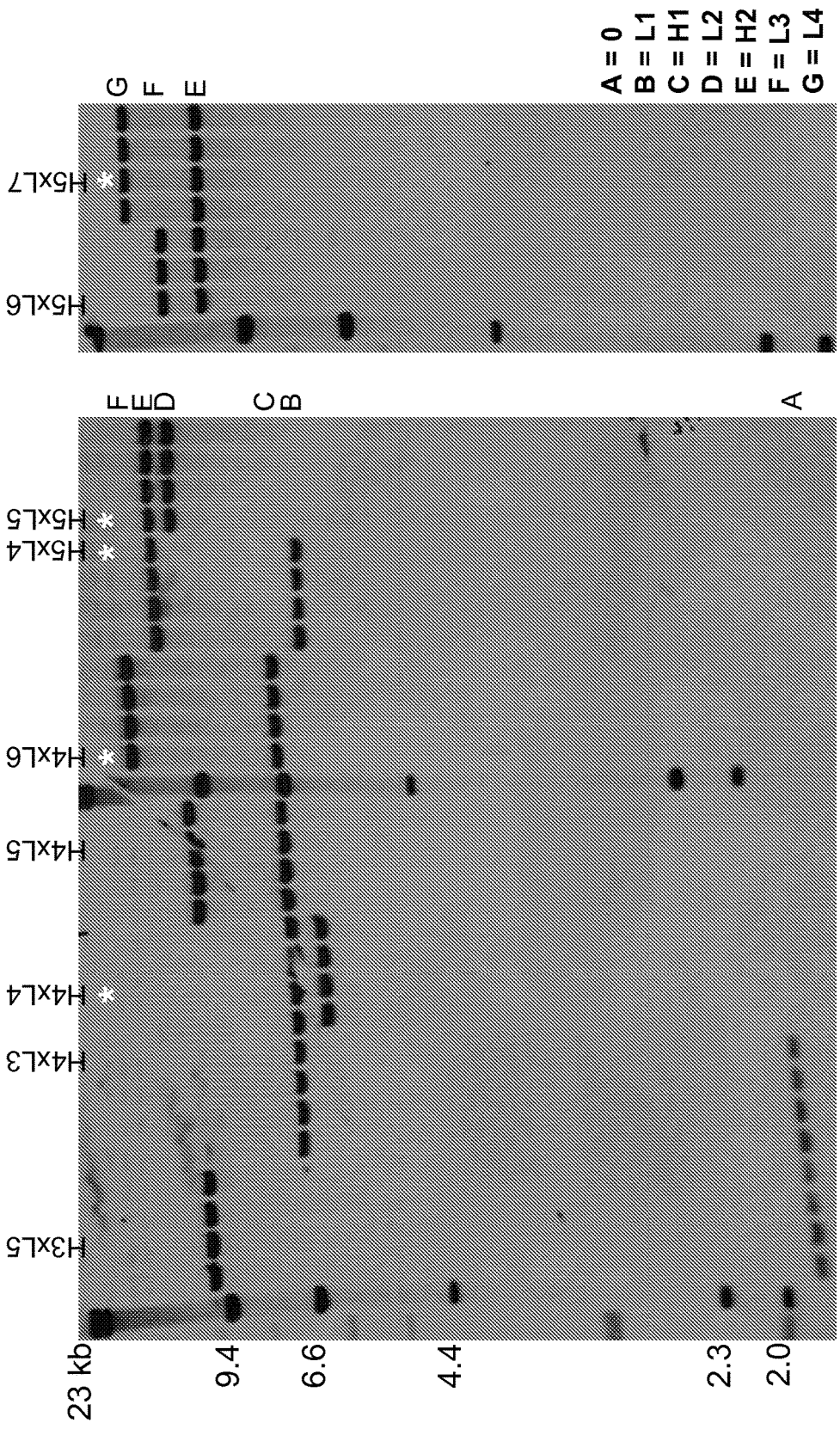

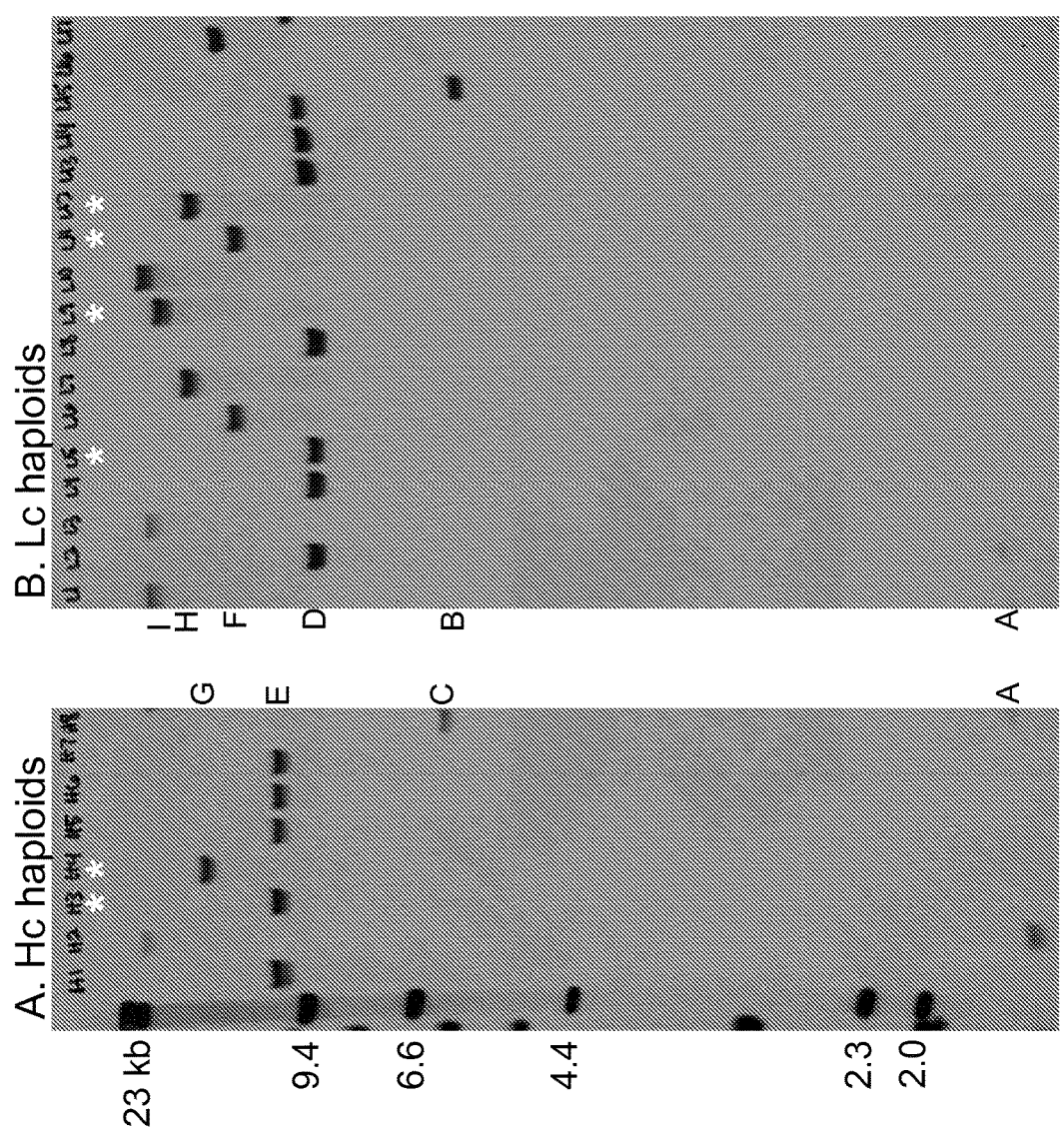
FIG. 28. Ab-B – Haploid Southern (pGAP locus)

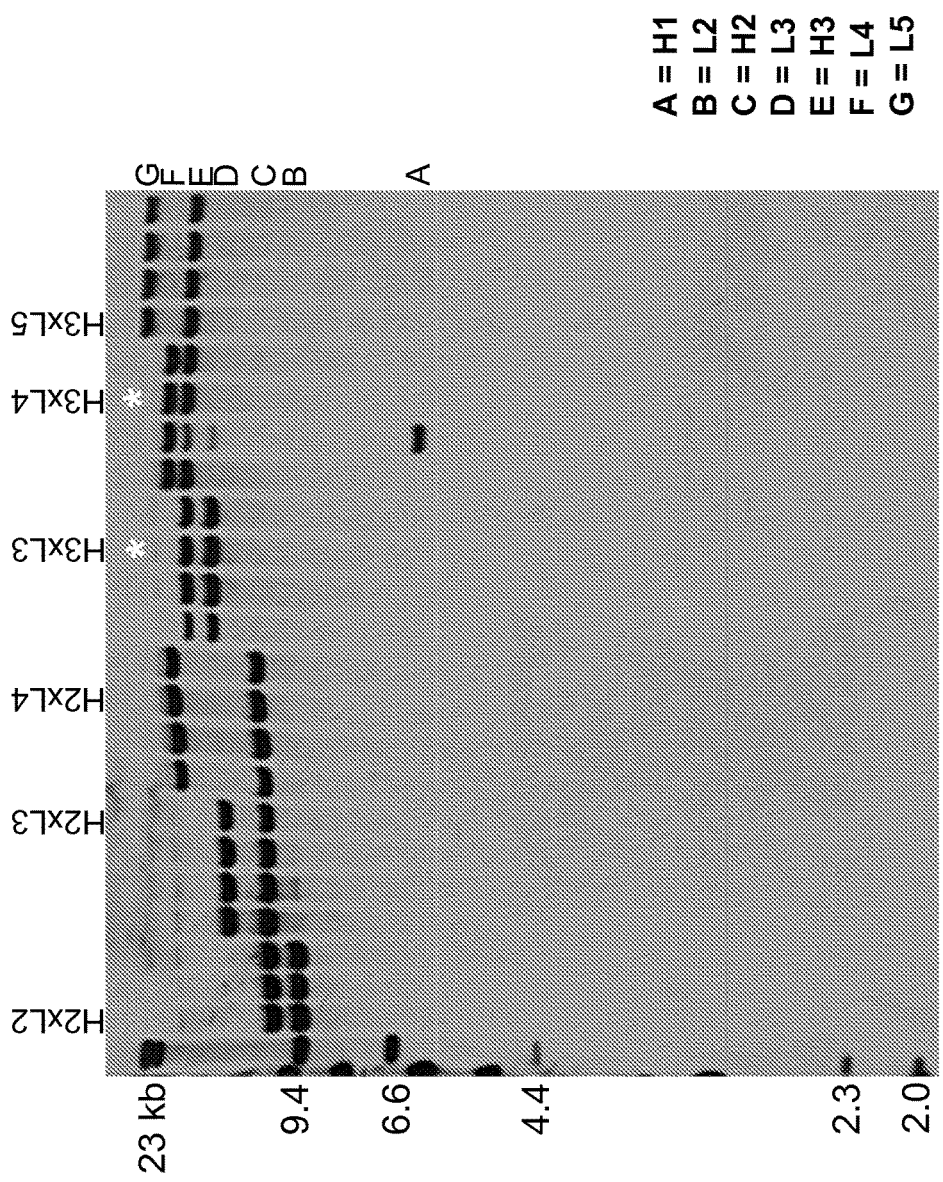
FIG. 29. Ab-B – Diploid Southern (pGAP locus)

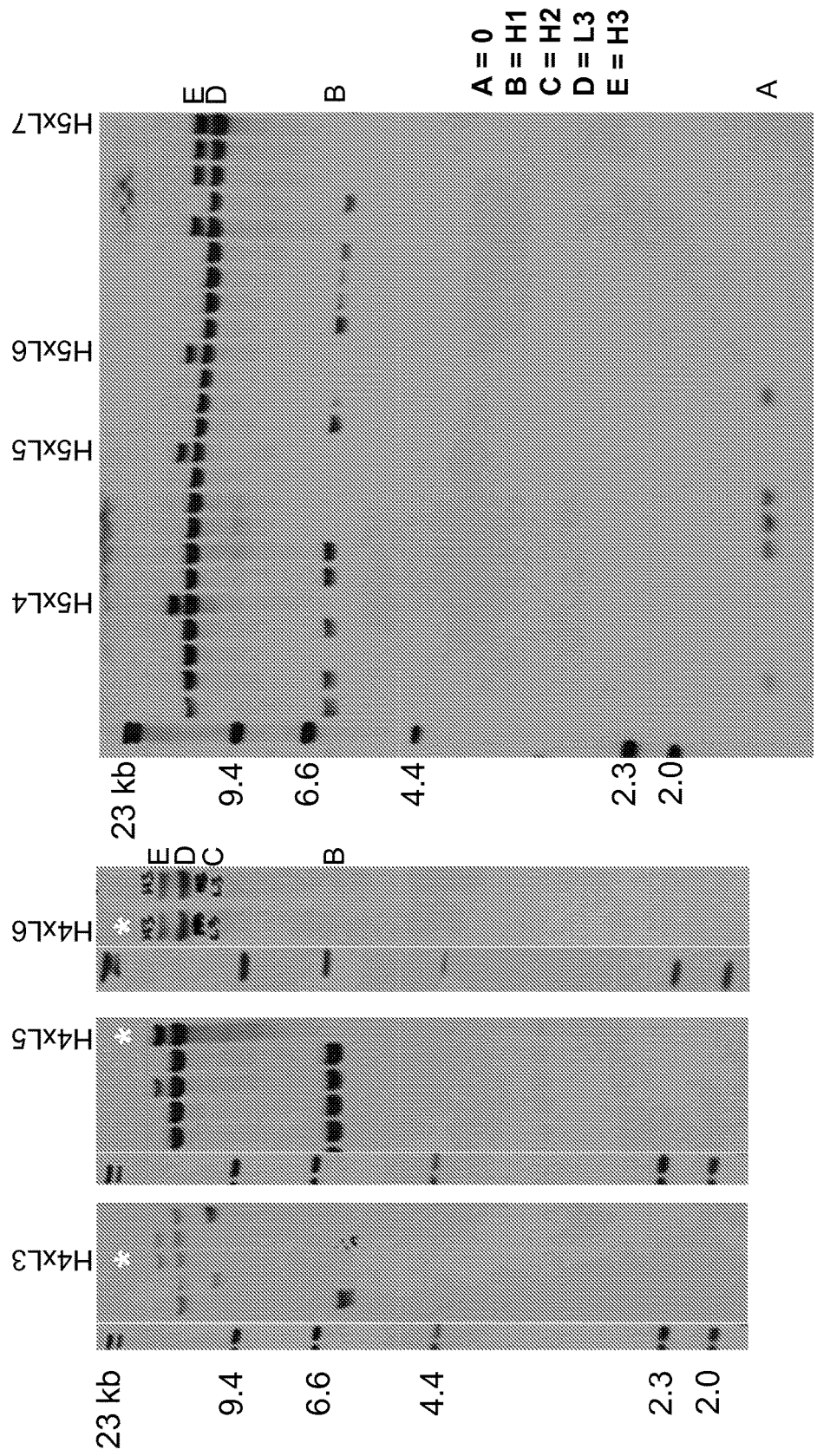
FIG. 30. Ab-B – Diploid Southern (pGAP locus)

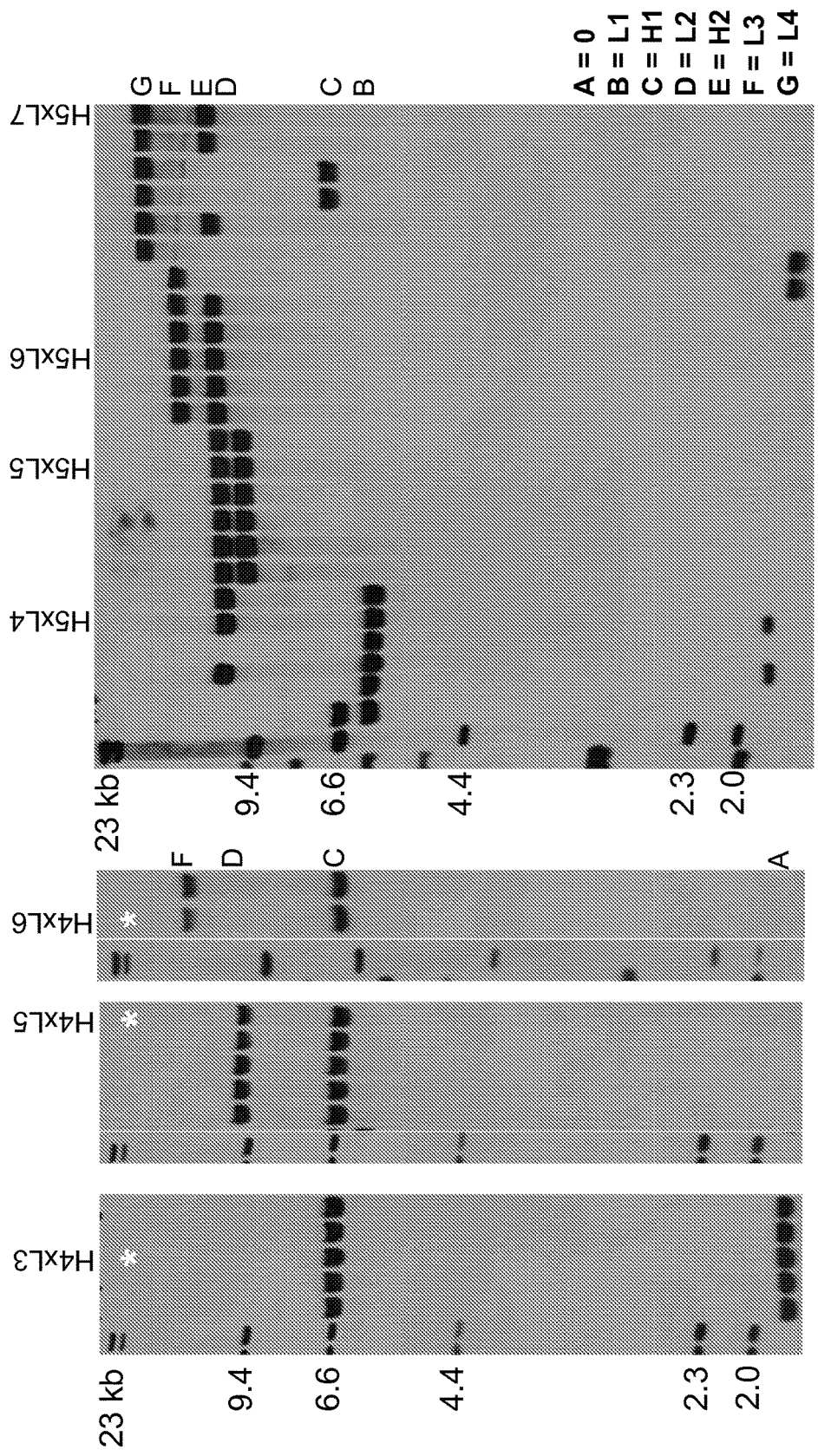
FIG. 31. Ab-B – Diploid Southern (HIS4 TT locus)

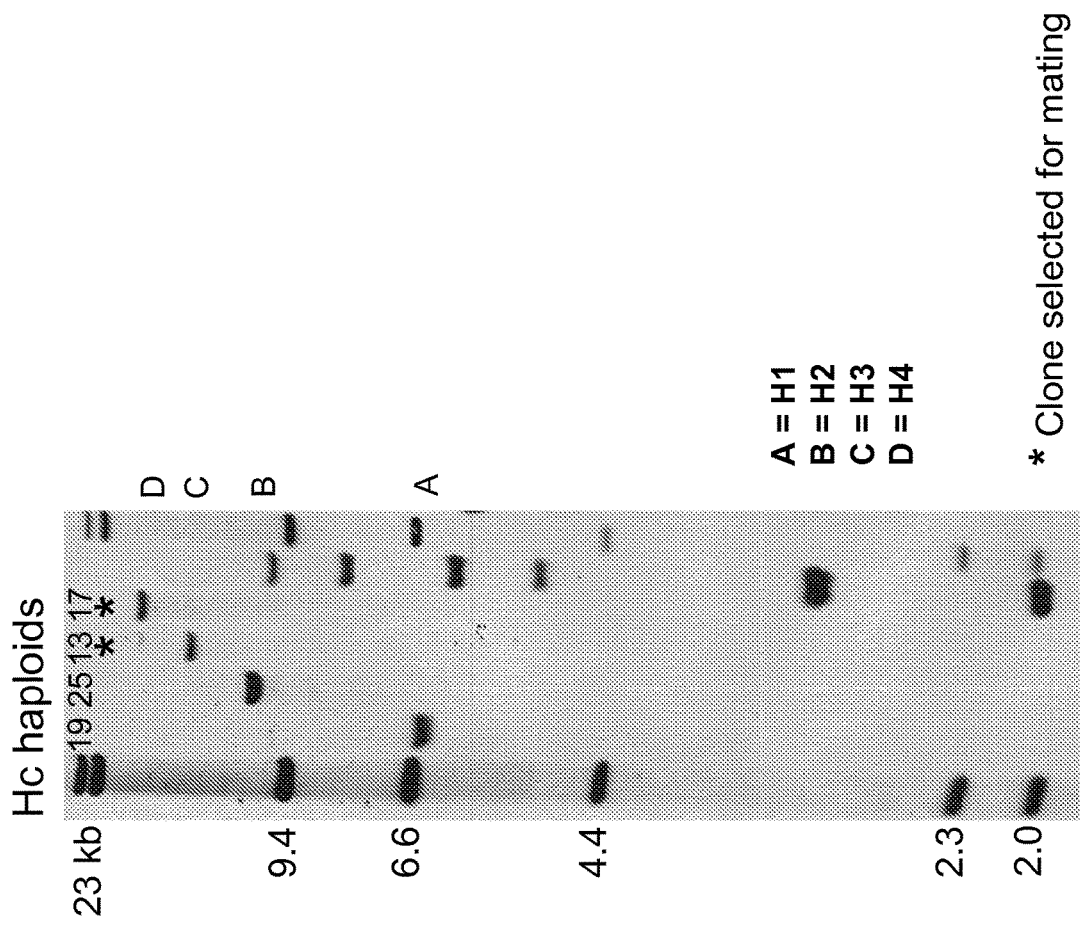
FIG 32. Ab-C – Haploid Southern (3'AOX TT locus)

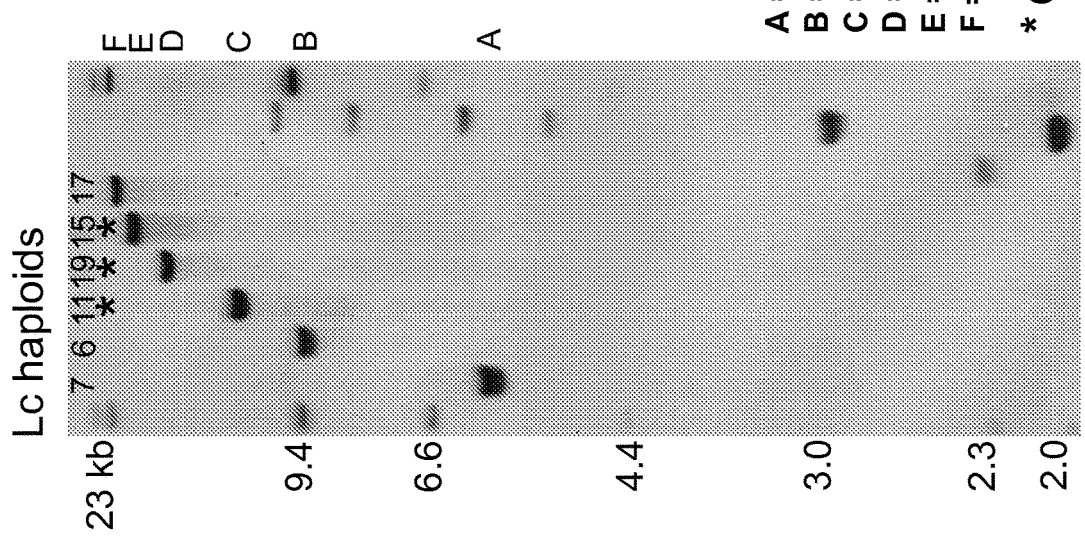
FIG 33. Ab-C – Haploid Southern (3'AOX TT locus)

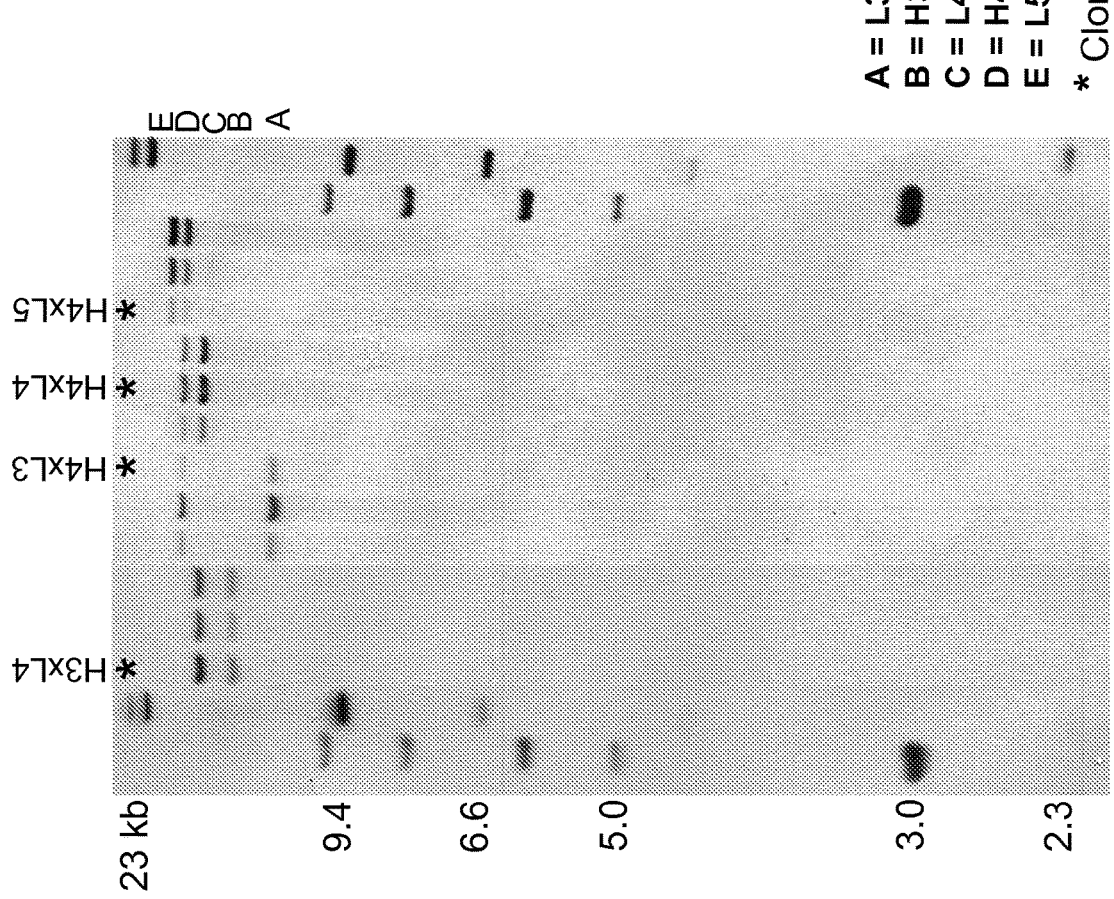
FIG. 34. Ab-C – Diploid Southern (3'AOX TT locus)

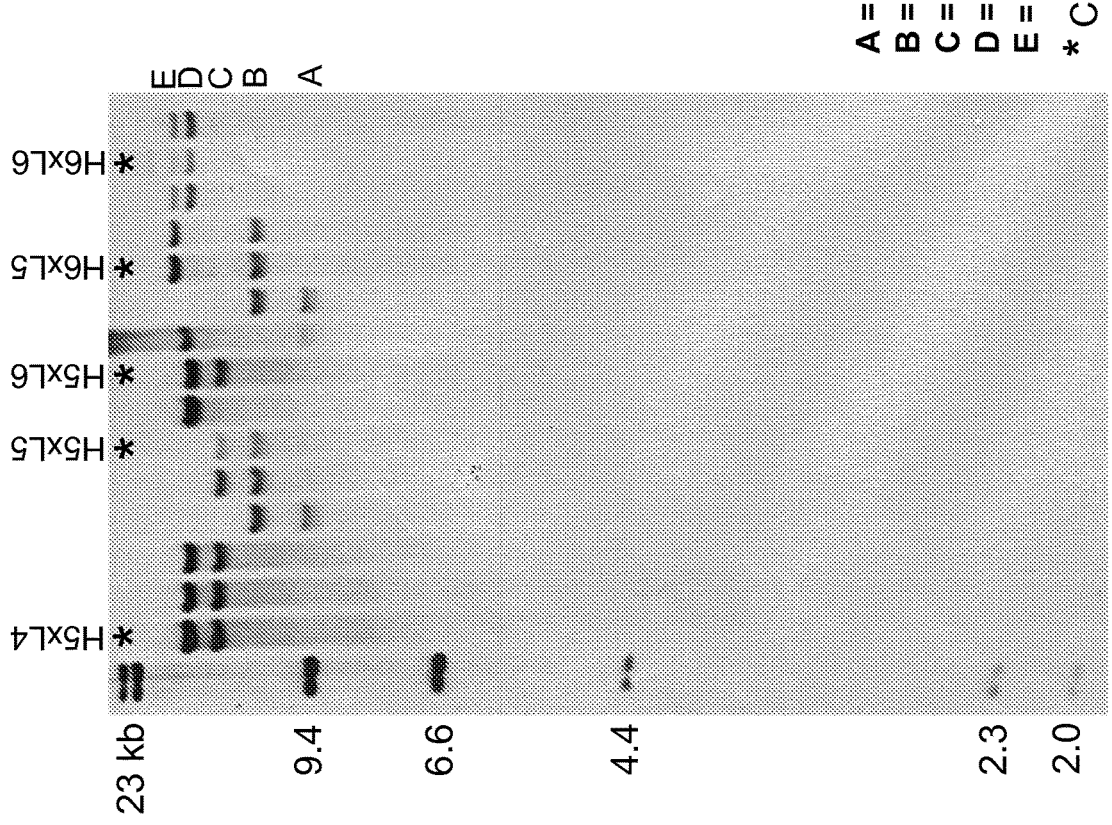

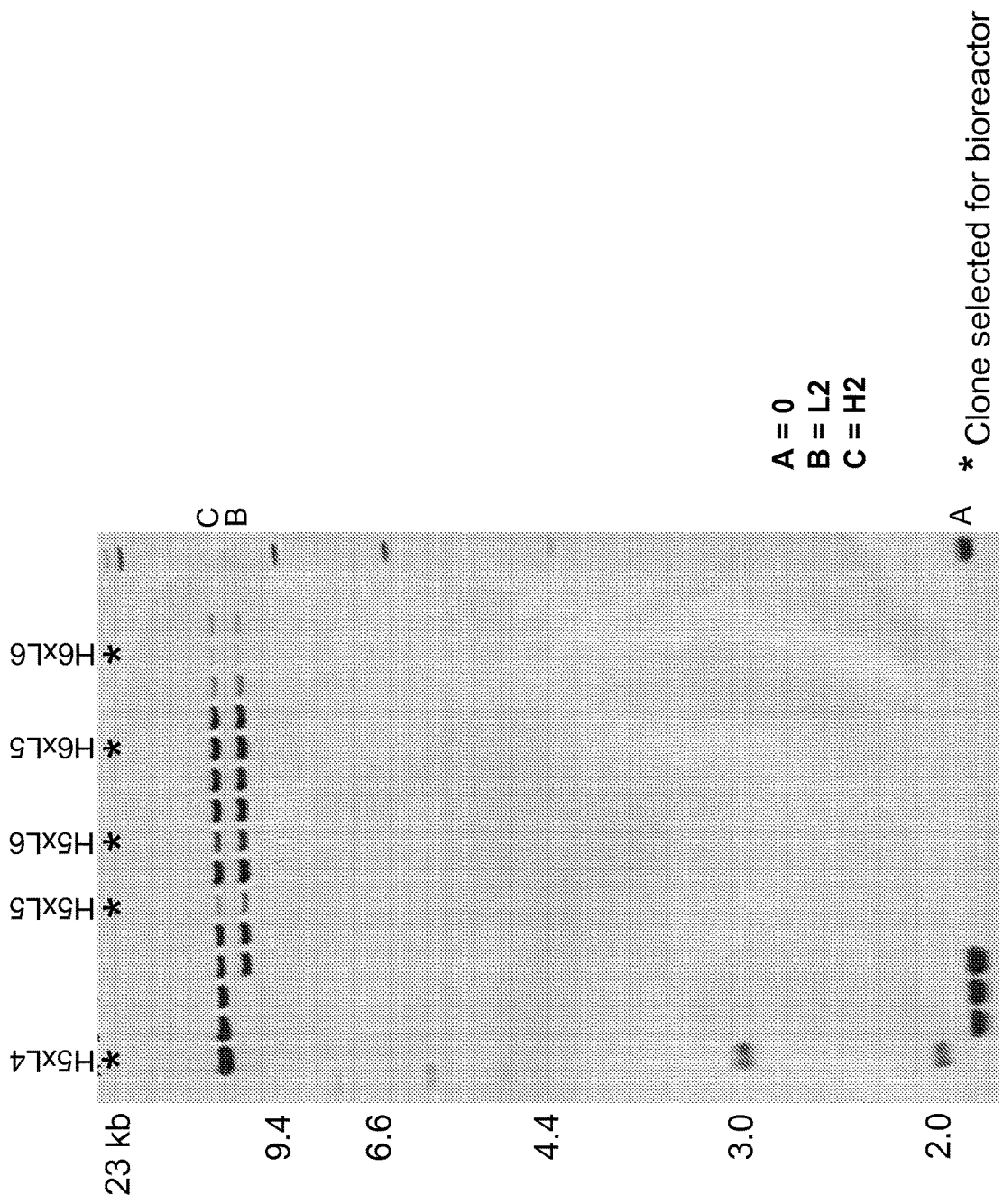
FIG. 36. Ab-C – Diploid Southern (HIS4 TT locus)

FIG. 37

| | \multicolumn{10}{c}{Heavy Chain Gene Copy Number} |
| | 1 | 2 | 3 | 4 | 5 | 6 | 7 | 8 | 9 | 10 |
|---|---|---|---|---|---|---|---|---|---|---|
| 1 | | H2xL1 | H3xL1 | H4xL1 | H5xL1 | H6xL1 | H7xL1 | H8xL1 | H9xL1 | H10xL1 |
| 2 | H1xL2 | H2xL2 | H3xL2 | H4xL2 | H5xL2 | H6xL2 | H7xL2 | H8xL2 | H9xL2 | H10xL2 |
| 3 | H1xL3 | H2xL3 | H3xL3 | H4xL3 | H5xL3 | H6xL3 | H7xL3 | H8xL3 | H9xL3 | H10xL3 |
| 4 | H1xL4 | H2xL4 | H3xL4 | H4xL4 | H5xL4 | H6xL4 | H7xL4 | H8xL4 | H9xL4 | H10xL4 |
| 5 | H1xL5 | H2xL5 | H3xL5 | H4xL5 | H5xL5 | H6xL5 | H7xL5 | H8xL5 | H9xL5 | H10xL5 |
| 6 | H1xL6 | H2xL6 | H3xL6 | H4xL6 | H5xL6 | H6xL6 | H7xL6 | H8xL6 | H9xL6 | H10xL6 |
| 7 | H1xL7 | H2xL7 | H3xL7 | H4xL7 | H5xL7 | H6xL7 | H7xL7 | H8xL7 | H9xL7 | H10xL7 |
| 8 | H1xL8 | H2xL8 | H3xL8 | H4xL8 | H5xL8 | H6xL8 | H7xL8 | H8xL8 | H9xL8 | H10xL8 |
| 9 | H1xL9 | H2xL9 | H3xL9 | H4xL9 | H5xL9 | H6xL9 | H7xL9 | H8xL9 | H9xL9 | H10xL9 |
| 10 | H1xL10 | H2xL10 | H3xL10 | H4xL10 | H5xL10 | H6xL10 | H7xL10 | H8xL10 | H9xL10 | H10xL10 |

Light Chain Gene Copy Number

FIG. 38

Ab-A Sequences

Ab-A Heavy chain (humanized) Full length protein sequence – yeast produced.

EVQLVESGGGLVQPGGSLRLSCAVSGLDLSSYYMQWVRQAPGKGLEWVGVIGINDNTYYASWAKGRFTISRDNSKTTVYL
QMNSLRAEDTAVYFCARGDIWGQGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDARVEPKSCDKTHTCPPCPAPELLGGPSVFLFPPKPKDTL
MISRTPEVTCVVVDVSHEDPEVKFNWYVDGVEVHNAKTKPREEQYASTYRVVSVLTVLHQDWLNGKEYKCKVSNKALPA
PIEKTISKAKGQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK  (SEQ ID NO: 1)

Ab-A Variable region heavy chain (humanized) protein sequence.

EVQLVESGGGLVQPGGSLRLSCAVSGLDLSSYYMQWVRQAPGKGLEWVGVIGINDNTYYASWAKGRFTISRDNSKTTVYL
QMNSLRAEDTAVYFCARGDIWGQGTLVTVSS  (SEQ ID NO: 2)

Ab-A Variable region heavy chain (humanized) CDR protein sequences.

CDR1: SYYMQ  (SEQ ID NO: 3)

CDR2: VIGINDNTYYASWAKG  (SEQ ID NO: 4)

CDR3: GDI

Ab-A Variable region heavy chain (humanized) CDR DNA sequences. CDR1: Bold; CDR2: Underlined; CDR3: Italics.

GAGGTGCAGCTTGTGGAGTCTGGGGGAGGCTTGGTCCAGCCTGGGGGGTCCCTGAGACTCTCCTGTGCAGTCTCTGGAC
TCGACCTCAGTAGCTACTACATGCAATGGGTCCGTCAGGCTCCAGGGAAGGGGCTGGAGTGGGTCGGAGTCATTGGTA
TCAATGATAACACATACTACGCGAGCTGGGCGAAAGGCCGATTCACCATCTCCAGAGACAATTCCAAGACCACGGTGT
ATCTTCAAATGAACAGCCTGAGAGCTGAGGACACTGCTGTGTATTTCTGTGCTAGA*GGGACATC*TGGGGCCAAGGGAC
CCTCGTCACCGTCTCGAGC  (SEQ ID NO: 5)

FIG. 38 (CONTINUED)

Ab-A Heavy chain (humanized) Full length DNA sequence – yeast produced.

GAGGTGCAGCTTGTGGAGTCTGGGGGAGGCTTGGTCCAGCCTGGGGGGTCCCTGAGACTCTCCTGTGCAGTCTCTGGAC
TCGACCTCAGTAGTACTACACATACGCAGTCAATGGTCCGTCAGGCTCCAGGGAAGGGGCTGGAGTGGGTCGAGTCATTGGTA
TCAATGATAACACATACTACGCAGCTGGGCAGCTGGGCGAAAGGCCATCTCCAGAGACACTCCAAGAACACGGGTGT
ATCTTCAAATGAACAGCCTGAGAGCTGAGGACACGGCTGTGTATTTCTGTGCTAGAGGGACATCTGGGGCCAAGGA
CCCTCGTCACCGTCTCGAGCGCCTCCACCAAGGGCCCATCGGTCTTCCCCCTGGCACCCTCCTCCAAGAGCACCTCTGG
GGGCACAGCGGCCCTGGGCTGCCTGGTCAAGGACTACTTCCCCGAACCGGTGACGGTGTCGTGGAACTCAGGCGCCCT
GACCAGCGGCGTGCACACCTTCCCGGCTGTCCTACAGTCCTCAGGACTCTACTCCCTCAGCAGCGTGGTGACCGTGCCC
TCCAGCAGCTTGGGCACCCAGACCTACATCTGCAACGTGAATCACAAGCCCAGCAACACCAAGGTGGACGCGGAGAGTT
GAGCCCAAATCTGTGACAAACTCACACATGCCCACCGTGCCCAGCACCTGAACTCCTGGGGGGACCGTCAGTCTTCC
TCTTCCCCCCAAAACCCAAGGACACCCTCATGATCTCCCGGACCCCTGAGGTCACATGCGTGGTGGTGGACGTGAGCCA
CGAAGACCCTGAGGTCAAGTTCAACTGGTACGTGGACGGCGTGGAGGTGCATAATGCCAAGACAAAGCCGCGGGAGG
AGCAGTACGCAGCAGCACCGTGTGCTCAGCGTCCTCGTGCTCCAGGAGGACTGGCTGAATGGCAAGGAGTACA
AGTGCAAGGTCTCCAACAAAGCCCTCCCAGCCCCCATCGAGAAAACCATCTCCAAGCCAAAGGGCAGCCCCGAGAAC
CACAGGTGTACACCCTGCCCCCATCCCGGGAGGAGATGACCAAGAACCAGGTCAGCCTGACCTGCCTGGTCAAAGGCT
TCTATCCCAGCGACATCGCCGTGGAGTGGGAGAGCAATGGGCAGCCGGAGAACAACTACAAGACCACGCCTCCCGTGC
TGGACTCCGACGGCTCCTTCTTCCTCTACAGCAAGCTCACCGTGGACAAGAGCAGGTGGCAGCAGGGGAACGTCTTCTC
ATGCTCCGTGATGCATGAGGCTCTGCACAACCACTACACGCAGAAGAGCCTCTCCCTGTCTCCGGGTAAATGA (SEQ ID NO: 6)

Ab-A Light chain (humanized) Full length protein sequence.

QVLTQSPSSLSASVGDRVTINCQASQSVYDNNYLAWYQQKPGKVPKQLIYSTSTLASGVPSRFSGSGSGTDFTLTISSLQPED
VATYYCLGSYDCSSGDCFVFGGGTKVEIKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC    (SEQ ID NO: 7)

Ab-A Variable region Light chain (humanized) protein sequence.

QVLTQSPSSLSASVGDRVTINCQASQSVYDNNYLAWYQQKPGKVPKQLIYSTSTLASGVPSRFSGSGSGTDFTLTISSLQPED
VATYYCLGSYDCFVFGGGTKVEIKR    (SEQ ID NO: 8)

FIG. 38 (CONTINUED)

Ab-A Variable region Light chain (humanized) protein CDR sequences.

CDR1: QASQSVYDNNYLA  (SEQ ID NO: 9)

CDR2: STSTLAS  (SEQ ID NO: 10)

CDR3: LGSYDCSSGDCFV  (SEQ ID NO: 11)

Ab-A Variable region Light chain (humanized) DNA sequence. CDR1: Bold; CDR2: Underlined; CDR3: Italics.

CAAGTGCTGACCCAGTCTCCATCCTCCCTGTCTGCATCTGTAGGAGACAGAGTCACCATCAATTGC**CAGGCCAGTCAG
AGTGTTTATGATAACAACTACCTAGCC**TGGTATCAGCAGAAACCAGGGAAAGTTCCTAAGCAACTGATCTATTCTAC
ATCCACTCTGGCATCTGGGGTCCCATCTCGTTTCAGTGGCAGTGGATCTGGGACAGATTTCACTCTCACCATCAGCAGC
CTGCAGCCTGAAGATGTTGCAACTTATTACTGT*CTAGGCAGTTATGATTGTAGTAGTGGTGATTGTTTTGTT*TCGGCGGAG
GAACCAAGGTGGAAATCAAACGT   (SEQ ID NO: 12)

Ab-A Light chain (humanized) Full length DNA sequence.

CAAGTGCTGACCCAGTCTCCATCCTCCCTGTCTGCATCTGTAGGAGACAGAGTCACCATCAATTGCCAGGCCAGTCAGA
GTGTTTATGATAACAACTACCTAGCCTGGTATCAGCAGAAACCAGGGAAAGTTCCTAAGCAACTGATCTATTCTACATC
CACTCTGGCATCTGGGGTCCCATCTCGTTTCAGTGGCAGTGGATCTGGGACAGATTTCACTCTCACCATCAGCAGCCTG
CAGCCTGAAGATGTTGCAACTTATTACTGTCTAGGCAGTTATGATTGTAGTAGTGGTGATTGTTTTGTTTCGGCGGAGG
AACCAAGGTGGAAATCAAACGTACGGTGGCTGCACCATCTGTCTTCATCTTCCCGCCATCTGATGAGCAGTTGAAATCT
GGAACTGCCTCTGTTGTGTGCCTGCTGAATAACTTCTATCCCAGAGAGGCCAAAGTACAGTGGAAGGTGGATAACGCCC
TCCAATCGGGTAACTCCCAGGAGAGTGTCACAGAGCAGGACAGCAAGGACAGCACCTACAGCCTCAGCAGCACCCTGA
CGCTGAGCAAAGCAGACTACGAGAAACACAAAGTCTACGCCTGCGAAGTCACCCATCAGGGCCTGAGCTCGCCCGTCA
CAAAGAGCTTCAACAGGGGAGAGTGTTAG   (SEQ ID NO: 13)

FIG. 39

Ab-B Sequences

Ab-B Heavy chain (humanized) Full length protein sequence – yeast produced.

EVQLVESGGGLVQPGGSLRLSCAVSGIDLSGYYMNWVRQAPGKGLEWVGVIGINGATYYASWAKGRFTISRDNSKTTVYL
QMNSLRAEDTAVYFCARGDIWGQGTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDARVEPKSCDKTHTCPPCPAPELLGGPSVFLFPPKPKDTL
MISRTPEVTCVVVDVSHEDPEVKFNWYVDGVEVHNAKTKPREEQYASTYRVVSVLTVLHQDWLNGKEYKCKVSNKALPA
PIEKTISKAKGQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK   (SEQ ID NO: 14)

Ab-B Variable region heavy chain (humanized) protein sequence.

EVQLVESGGGLVQPGGSLRLSCAVSGIDLSGYYMNWVRQAPGKGLEWVGVIGINGATYYASWAKGRFTISRDNSKTTVYL
QMNSLRAEDTAVYFCARGDIWGQGTLVTVSS   (SEQ ID NO: 15)

Ab-B Variable region heavy chain (humanized) protein CDR sequences.

CDR1: GYYMN   (SEQ ID NO: 16)
CDR2: IGINGATYYASWAKG   (SEQ ID NO: 17)
CDR3: GDI

Ab-B Variable region heavy chain (humanized) DNA sequence. CDR1: Bold; CDR2: Underlined; CDR3: Italics.

GAGGTGCAGTTGTGGAGTCTGGGGGAGGCTTGGTCCAGCCTGGGGGGTCCCTGAGACTCTCCTGTGCAGTCTGGAA
TCGACCTCAGTGGCTACTACTACATGAACTGGGTCCGTCAGGCTCCAGGGAAGGGGCTGGAGTGGGTGGGAGTCATTGGT
ATTAATGGTGCCACATACTACGCGAGCTGGGCGAAAGGCCGATTCACCATCTCCAGAGACAATTCCAAGACCACGGTG
TATCTTCAAATGAACAGCCTGAGAGCTGAGGACACTGCTGTGTATTTCTGTGC*TAGAGGGACAT*CTGGGGCCAAGGGA
CCCTCGTCACCGTCTCGAGC   (SEQ ID NO: 18)

FIG. 39 (CONTINUED)

Ab-B Heavy chain (humanized) Full length DNA sequence – yeast produced.

GAGGTGCAGCTTGTGGAGTCTGGGGGAGGCTTGGTCCAGCCTGGGGGTCCCTGAGACTCTCCTGTGCAGTCTCTGGAA
TCGACCTCAGTGGCTACTACTACATACGGAGCTGGGTCCGTCAGGCTCCAGGGAAGGGGCTGGAGTGGGTGAGTCATTGGTA
TAATGGTGCCACATACTACGGAGCTGGGTGGGCGAAAGGCCGATTCACCATCTCCAGAGACAATTCCAAGAACACGGTGT
ATCTTCAAATGAACAGCCTGAGAGCTGAGGACACTGCTGTGTATTTCTGTGTCTAGAGGGGACATCTGGGGCCAAGGGA
CCCTCGTCACCGTCTCGAGCGGCCTGCCTGGTCAAGGACTACTTCCCCGAACCGGTGACGGTGTCGTGGAACTCAGGCGCCCT
GACCAGCGGCGTGCACACCTTCCCGGCTGTCCTACAGTCCTCAGGACTCTACTCCCTCAGCAGCGTGGTGACCGTGCCC
TCCAGCAGCTTGGGCACCCAGACCTACATCTGCAACGTGAATCACAAGCCCAGCAACACCAAGGTGGACGCGAGAGTT
GAGCCCAAATCTTGTGACAAAACTCACACATGCCCACCGTGCCCAGCACCTGAACTCCTGGGGGGACCGTCAGTCTTCC
TCTTCCCCCCAAAACCCAAGGACACCCTCATGATCTCCCGGACCCCTGAGGTCACATGCGTGGTGGTGGACGTGAGCCA
CGAAGACCCTGAGGTCAAGTTCAACTGGTACGTGGACGGCGTGGAGGTGCATAATGCCAAGACAAAGCCGCGGGAGG
AGCAGTACGCCAGCACGTACCGTGTGGTCAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATCTCCAAAGCCAAAGGGCAGCCCCGAGAAC
CACAGGTGTACACCCTGCCCCCATCCCGTGAGATGACCAAGAACCAGGTCAGCCTGACCTGCCTGGTCAAAGGCT
TCTATCCCAGCGACATCGCCGTGGAGTGGGAGAGCAATGGGCAGCCGGAGAACAACTACAAGACCACGCCTCCCGTGC
TGGACTCCGACGGCTCCTTCTTCCTCTACAGCAAGCTCACCGTGGACAAGAGCAGGTGGCAGCAGGGGAACGTCTTCTC
ATGCTCCGTGATGCATGAGGCTCTGCACAACCACTACACGCAGAAGAGCCTCTCCCTGTCTCCGGGTAAATGA (SEQ
ID NO: 19)

Ab-B Light chain (humanized) Full length protein sequence.

QVLTQSPSSLSASVGDRVTINCQASQSVYHNTYLAWYQQKPGKVPKQLIYDASTLASGVPSRFSGSGSGTDFTLTISSLQPED
VATYYCLGSYDCTNGDCFVFGGGTKVEIKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC   (SEQ ID NO: 20)

Ab-B Variable region Light chain (humanized) protein sequence.

QVLTQSPSSLSASVGDRVTINCQASQSVYHNTYLAWYQQKPGKVPKQLIYDASTLASGVPSRFSGSGSGTDFTLTISSLQPED
VATYYCLGSYDCTNGDCFVFGGGTKVEIKR   (SEQ ID NO: 21)

FIG. 39 (CONTINUED)

Ab-B Variable region Light chain (humanized) protein CDR sequences.

CDR1: QASQSVYHNTYLA (SEQ ID NO: 22)

CDR2: DASTLAS (SEQ ID NO: 23)

CDR3: LGSYDCTNGDCFV (SEQ ID NO: 24)

Ab-B Variable region Light chain (humanized) DNA sequence. CDR1: Bold; CDR2: Underlined; CDR3: Italics.

CAAGTGCTGACCCAGTCTCCATCCTCCCTGTCTGCATCTGTAGGAGACAGAGTCACCATCAATTGC**CAGGCCAGTCAG
AGTGTTTATCATAACACCTACCTGGC**CTGGTATCAGCAGAAACCAGGGAAAGTTCCTAAGCAACTGATCTATGATGC
ATCCACTCTGGCATCTGGGGTCCCATCTCGTTTCAGTGGCAGTGGATCTGGGACAGATTTCACTCTCACCATCAGCAGC
CTGCAGCCTGAAGATGTTGCAACTTATTACTGT*CTCGGGCAGTTATGATTGTACTAATGGTGATTGTTTTGTT*TCGGCGGAG
GAACCAAGGTGGAAATCAAACGT   (SEQ ID NO: 25)

Ab-B Light chain (humanized) Full length DNA sequence.

CAAGTGCTGACCCAGTCTCCATCCTCCCTGTCTGCATCTGTAGGAGACAGAGTCACCATCAATTGCCAGGCCAGTCAGA
GTGTTTATCATAACACCTACCTGGCCTGGTATCAGCAGAAACCAGGGAAAGTTCCTAAGCAACTGATCTATGATGCATC
CACTCTGGCATCTGGGGTCCCATCTCGTTTCAGTGGCAGTGGATCTGGGACAGATTTCACTCTCACCATCAGCAGCCTG
CAGCCTGAAGATGTTGCAACTTATTACTGTCTCGGGCAGTTATGATTGTACTAATGGTGATTGTTTTGTTTCGGCGGAGG
AACCAAGGTGGAAATCAAACGTACGGTGGCTGCACCATCTGTCTTCATCTTCCCGCCATCTGATGAGCAGTTGAAATCT
GGAACTGCCTCTGTTGTGTGCCTGCTGAATAACTTCTATCCCAGAGGCCAAGTACAGTGGAAGGTGGATAACGCCC
TCCAATCGGGTAACTCCCAGGAGAGTGTCACAGAGCAGGACAGCAAGGACAGCACCTACAGCCTCAGCAGCACCCTGA
CGCTGAGCAAAGCAGACTACGAGAAACACAAAGTCTACGCCTGCGAAGTCACCCATCAGGGCCTGAGCTCGCCCGTCA
CAAAGAGCTTCAACAGGGGAGAGTGTTAG   (SEQ ID NO: 26)

FIG. 40

Ab-C Sequences

Ab-C Heavy Chain Full length DNA sequence

GAGGTGCAGCTGGTGGAGTCTGGGGGAGGCTTGGTCAGCCTGGGGGGTCCCTGAGACTCTCCTGTGCAGCCTCTGGAT
TCTCCCTCAGTAACTACTACGTGACCTGGGTCCGTCAGGCTCCAGGGAAGGGGCTGGAGTGGGTCGGCATCATCTATGG
TAGTGATGAAACCGCCTACTACCTCCGCTATAGGCCGATTCACCATCTCCAGAGACAATTCCAAGAACACCCTGTAT
CTTCAAATGAACAGCCTGAGAGCTGAGGACACTGCTGTGTATTACTGTGCTAGAGATGATAGTAGTGACTGGGATGCA
AAGTTCAACTTGTGGGGCCAAGGCACCCTGGTCACCGTCTCGAGCGGCCCTGGGTCCTGGTCAAGGACTACTTCCCCTGG
CACCCTCCTCCAAGAGCACCTCTGGGGGCACAGCGGCCCTGGGCTGCCTGGTCAAGGACTACTTCCCCGAACCGGTGAC
GGTGTCGTGGAACTCAGGCGCCCTGACCAGCGGCGTGCACACCTTCCCGGCTGTCCTACAGTCCTCAGGACTCTACTCC
CTCAGCAGCGTGGTGACCGTGCCCTCCAGCAGCTTGGGCACCCAGACCTACATCTGCAACGTGAATCACAAGCCCAGC
AACACCAAGGTGGACAAGAGAGTTGAGCCCAAATCTTGTGACAAAACTCACACATGCCCACCGTGCCCAGCACCTGAA
CTCCTGGGGGACCGTCAGTCTTCCTCTTCCCCCCAAAACCCAAGGACACCCTCATGATCTCCCGGACCCCTGAGGTCA
CATGCGTGGTGGTGGACGTGAGCCACGAAGACCCTGAGGTCAAGTTCAACTGGTACGTGGACGGCGTGGAGGTGCATA
ATGCCAAGACAAAGCCGCGGGAGGAGCAGTACAACAGCACGTACCGTGTGGTCAGCGTCCTCACCGTCCTGCACCAGG
ACTGGCTGAATGGCAAGGAGTACAAGTGCAAGGTCTCCAACAAAGCCCTCCCAGCCCCCATCGAGAAAACCATCTCCA
AAGCCAAAGGGCAGCCCCGAGAACCACAGGTGTACACCCTGCCCCCATCCCGGGAGGAGATGACCAAGAACCAGGTC
AGCCTGACCTGCCTGGTCAAAGGCTTCTATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCTCTACAGCAAGCTCACCGTGGACAAGAGCA
GGTGGCAGCAGGGGAACGTCTTCTCATGCTCCGTGATGCATGAGGCTCTGCACAACCACTACACGCAGAAGAGCCTCT
CCCTGTCTCCGGGTAAA (SEQ ID NO: 27)

Ab-C Heavy Chain Full length polypeptide sequence

EVQLVESGGGLVQPGGSLRLSCAASGFSLSNYYVTWVRQAPGKGLEWVGIIYGSDETAYATSAIGRFTISRDNSKNTLYLQM
NSLRAEDTAVYYCARDDSSDWDAKFNLWGQGTLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYASTYRVVSVLTVLHQDWLNGKEYKCKVS
NKALPAPIEKTISKAKGQPREPQVYTLPPSREEMTKNQVSLTCLVKGFYPSDIAVEWESNGQPENNYKTTPPVLDSDGSFFLY
SKLTVDKSRWQQGNVFSCSVMHEALHNHYTQKSLSLSPGK (SEQ ID NO: 28)

FIG. 40 (CONTINUED)

Ab-C Light Chain Full length DNA sequence

GCTATCCAGATGACCCAGTCTCCTTCCTCCCTGTCTGCATCTGTAGGAGACAGAGTCACCATCACTTGCCAGGCCAGTC
AGAGCATTAACAATGAGTTATCCTGGTATCAGCAGAAACCAGGGAAAGCCCCTAAGCTCCTGATCTATAGGGCATCCA
CTCTGGCATCTGGGGTCCCATCAAGGTTCAGCGGCAGTGGATCTGGGACAGACTTCACTCTCACCATCAGCAGCCTGCA
GCCTGATGATTTTGCAACTTATTACTGCCAACAGGGTTATAGTCTGAGGAACATTGATAATGCTTTCGGCGGAGGGACC
AAGGTGGAAATCAAACGTACGGTGGCTGCACCATCTGTCTTCATCTTCCCGCCATCTGATGAGCAGTTGAAATCTGGAA
CTGCCTCTGTTGTGTGCCTGCTGAATAACTTCTATCCCAGAGAGGCCAAAGTACAGTGGAAGGTGGATAACGCCCTCCA
ATCGGGTAACTCCCAGGAGAGTGTCACAGAGCAGGACAGCAAGGACAGCACCTACAGCCTCAGCAGCACCCTGACGCT
GAGCAAAGCAGACTACGAGAAACACAAAGTCTACGCCTGCGAAGTCACCCATCAGGGCCTGAGCTCGCCCGTCACAAA
GAGCTTCAACAGGGGAGAGTGT (SEQ ID NO: 29)

Ab-C Light Chain Full length polypeptide sequence

AIQMTQSPSSLSASVGDRVTITCQASQSINNELSWYQQKPGKAPKLLIYRASTLASGVPSRFSGSGSGTDFTLTISSLQPDDFAT
YYCQQGYSLRNIDNAFGGGTKVEIKRTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC (SEQ ID NO: 30)

MULTI-COPY STRATEGY FOR HIGH-TITER AND HIGH-PURITY PRODUCTION OF MULTI-SUBUNIT PROTEINS SUCH AS ANTIBODIES IN TRANSFORMED MICROBES SUCH AS *PICHIA PASTORIS*

CROSS REFERENCE TO RELATED APPLICATIONS

This application is a divisional of U.S. patent application Ser. No. 13/589,584, filed Aug. 20, 2012, which is a Continuation-in-part of U.S. patent application Ser. No. 13/466,795, filed May 8, 2012, which claims priority to U.S. Provisional Appl. No. 61/525,307, filed Aug. 19, 2011, the disclosures of each of which are hereby incorporated by reference in their entireties.

This application includes as part of its disclosure a biological sequence listing which is being concurrently submitted through EFS-Web. Said biological sequence listing is contained in a file named "43257o4603.txt" which was created Oct. 29, 2018, and has a size of 43,744 bytes, and is hereby incorporated by reference in its entirety.

FIELD

The present disclosure generally relates to methods for producing heterologous proteins in transformed cells. In particular, the present disclosure provides improved methods of producing multi-subunit proteins, including antibodies and other multi-subunit proteins such as hormones and receptors, which may or may not be secreted, with a higher yield and decreased production of undesired side-products. In exemplary embodiments, the transformed cells are a yeast, such as *Pichia pastoris* or *Saccharomyces cerevisiae*.

BACKGROUND

Conventional antibodies are tetrameric proteins composed of two identical light chains and two identical heavy chains. Pure human antibodies of a specific type can be difficult or impossible to purify from natural sources in sufficient amounts for many purposes. As a consequence, biotechnology and pharmaceutical companies have turned to recombinant DNA-based methods to prepare antibodies on a large scale. The production of functional antibodies generally involves not just the synthesis of the two polypeptides but also a number of post-translational events, including proteolytic processing of the N-terminal secretion signal sequence; proper folding and assembly of the polypeptides into tetramers; formation of disulfide bonds; and typically includes a specific N-linked glycosylation. All of these events take place in the eukaryotic cell secretory pathway, an organelle complex unique to eukaryotic cells.

Recombinant synthesis of such complex proteins has typically relied on cultures of higher eukaryotic cells to produce biologically active material, with cultured mammalian cells being very commonly used. However, mammalian tissue culture-based production systems incur significant added expense and complication relative to microbial fermentation methods. Additionally, products derived from mammalian cell culture may require additional safety testing to ensure freedom from mammalian pathogens (including viruses) that might be present in the cultured cells or animal-derived products used in culture, such as serum.

Prior work has help to establish the yeast *Pichia pastoris* as a cost-effective platform for producing functional antibodies that are potentially suitable for research, diagnostic, and therapeutic use. See co-owned U.S. Pat. Nos. 7,935,340 and 7,927,863, each of which is incorporated by reference herein in its entirety. Methods are also known in the literature for design and optimization of *P. pastoris* fermentations for expression of recombinant proteins, including optimization of the cell density, broth volume, substrate feed rate, and the length of each phase of the reaction. See Zhang et al., "Rational Design and Optimization of Fed-Batch and Continuous Fermentations" in Cregg, J. M., Ed., 2007, *Pichia Protocols* (2nd edition), Methods in Molecular Biology, vol. 389, Humana Press, Totowa, N.J., pgs. 43-63.

Though recombinant multi-subunit proteins can be produced from cultured cells, undesired side-products may also be produced. For example, the cultured cells may produce the desired multi-subunit protein along with free monomers, complexes having incorrect stoichiometry, or proteins having undesired or aberrant glycosylation. Purification of the desired multi-subunit protein can increase production cost, and the steps involved in purification may decrease total yield of active complexes. Moreover, even after purification, undesired side-products may be present in amounts that cause concern. For example, glycosylated side-products may be present in amounts that increase the risk of an immune reaction after administration, while aberrant complexes or aggregates may decrease specific activity and may also be potentially immunogenic.

SUMMARY

The present disclosure provides improved methods and compositions of matter that provide for the recombinant production of multi-subunit proteins such as antibodies, hormones and receptors and other multi-subunit complexes, with a higher yield. These multiunit polypeptides may comprise 2 or more subunits which may be the same or different (i.e., homo- or heteropolymeric polypeptides. In exemplary embodiments, the secreted or intracellular yield of such multi-subunit proteins may be increased by at least 50%, by at least 100%, or more (relative to conventional methods) using the methods disclosed herein.

The present also disclosure provides improved methods and compositions of matter that provide for the recombinant production of antibodies and other multi-subunit proteins, with decreased production of undesired side-products. In exemplary embodiments, the undesired side product may be a glycosylated protein, such as a glycosylated antibody heavy chain, whose relative abundance may be decreased by at least 10%, at least 20%, at least 30%, at least 40%, at least 50%, at least 60%, at least 70%, at least 80%, at least 90%, at least 95%, at least 96%, at least 97%, at least 98%, at least 99%, or down to undetectable levels compared to initial abundance levels (relative to conventional methods) using methods disclosed herein. Exemplary undesired side-products whose relative abundance may be so decreased may include one or more species having a different apparent molecular weight than the desired multi-subunit complex. For example, apparent molecular weight may be affected by differences in stoichiometry, folding, complex assembly, and/or glycosylation. For example, such undesired side products may be detected using size exclusion chromatography and/or gel electrophoresis, and may have a higher or lower apparent molecular weight than the desired multi-subunit complex. In exemplary embodiments, the undesired side-products may be detected under reducing conditions. In other exemplary embodiments, the undesired side-products may be detected under non-reducing conditions.

In exemplary embodiments, the present disclosure also provides improved methods and compositions of matter that provide for the recombinant production of antibodies and other multi-subunit complexes, with a higher yield. In exemplary embodiments, the yield may be increased by at least 10%, at least 20%, at least 30%, at least 40%, at least 50%, at least 100%, or more (relative to conventional methods) using the methods disclosed herein.

In exemplary embodiments, the host cell in which the multi-subunit proteins may be produced may be a yeast, for example in a *Pichia* species such as *P. pastoris* or another methylotrophic yeast, or in a *Saccharomyces* species such as *S. cerevisiae*, or another yeast such as a *Schizosaccharomyces* (e.g., *S. pombe*). Other examples of methylotrophic yeast which may be utilized in the present invention include *Pichia angusta* (also known in the art as *Hansenula polymorphs*), *Pichia* guillermordii, *Pichia methanolica, Pichia inositovera, Ogataea nitratoaversa*, and *Candida boidnii*.

In one aspect, the present disclosure provides improved methods of identifying a host cell that produces a desired antibody or other desired multi-subunit complex with a greater yield, which may comprise: (a) providing a panel of host cells, said panel comprising at least two host cells that each comprise genes that provide for expression of the subunits of said multi-subunit complex (e.g., the light chain and heavy chain of said desired antibody); (b) culturing each said host cell conditions that permit expression of the multi-subunit complex, wherein the genes in said at least two host cells provide for differing levels of expression of at least one subunit of said desired multi-subunit complex; (c) measuring the yield of the multi-subunit complex produced by each said host cell; and (d) identifying the host cell that produces a greater yield than another host cell in said panel of host cells as a host cell that produces a desired multi-subunit complex with a greater yield.

In another aspect, the present disclosure provides improved methods of identifying a host cell that produces a desired antibody or other desired multi-subunit complex with a greater purity, which may comprise: (a) providing a panel of host cells, said panel comprising at least two host cells that each comprise genes that provide for expression of the subunits of said multi-subunit complex (e.g., the light chain and heavy chain of said desired antibody); (b) culturing each said host cell conditions that permit expression of the multi-subunit complex, wherein the genes in said at least two host cells provide for differing levels of at least one subunit of said desired multi-subunit complex; (c) measuring the purity of said multi-subunit complex produced by each said host cell; and (d) identifying the host cell that produces a greater purity than another host cell in said panel of host cells as a host cell that produces a desired multi-subunit complex with a greater purity.

The host cell may be a eukaryotic cell, such as a yeast cell, such as a methylotrophic yeast, such as a yeast of the genus *Pichia*. Exemplary methylotrophic yeasts of the genus *Pichia* include *Pichia pastoris, Pichia angusta, Pichia guillermordii, Pichia methanolica*, and *Pichia inositovera*. The host cell may be produced by mating, e.g., by mating two haploid yeast cells that each contain one or more copies of at least one gene encoding a subunit of the multi-subunit complex. For example, multiple haploid cells may be produced containing known, differing numbers of copies of one or more subunits of said multi-subunit complex, such that mating between different combinations of haploid cells can rapidly produce a panel of diploid cells, each containing pre-selected numbers of copies of the genes encoding each subunit of the multi-subunit complex. Additionally, multiple diploid cells may be produced containing known, differing numbers of copies of one or more subunits of said multi-subunit complex, such that mating between different combinations of diploid cells can rapidly produce a panel of tetraploid cells, each containing pre-selected numbers of copies of the genes encoding each subunit of the multi-subunit complex.

In a preferred embodiment, the methylotrophic yeasts of the genus *Pichia* is *Pichia pastoris*. The host cell may be a diploid or tetraploid cell.

At least one of said genes encoding said subunits of the desired multi-subunit complex, such as said desired antibody light chain and/or heavy chain, may be expressed under control of an inducible or constitutive promoter, such as CUP1 (induced by the level of copper in the medium; see Koller et al., Yeast 2000; 16: 651-656.), tetracycline inducible promoters (see, e.g., Staib et al., Antimicrobial Agents And Chemotherapy, January 2008, p. 146-156), thiamine inducible promoters, AOX1, ICL1, glyceraldehyde-3-phosphate dehydrogenase (GAP), FLD1, ADH1, alcohol dehydrogenase II, GAL4, PHO3, PHO5, and Pyk promoters, chimeric promoters derived therefrom, yeast promoters, mammalian promoters, insect promoters, plant promoters, reptile promoters, amphibian promoters, viral promoters, and avian promoters.

At least one of said genes encoding said subunits of the desired multi-subunit complex, such as said desired antibody light chain and/or heavy chain, may be expressed under control of an inducible or constitutive promoter, such as CUP1, AOX1, ICL1, glyceraldehyde-3-phosphate dehydrogenase (GAP), FLD1, ADH1, alcohol dehydrogenase II, GAL4, PHO3, PHO5, and Pyk promoters, tetracycline inducible promoters, thiamine inducible promoters, chimeric promoters derived therefrom, yeast promoters, mammalian promoters, insect promoters, plant promoters, reptile promoters, amphibian promoters, viral promoters, and avian promoters.

The host cell may secrete said desired multi-subunit complex into the culture medium. Alternatively or in addition, said desired multi-subunit complex may be retained in said host cell and may be isolated therefrom.

Said host cell may be a diploid, tetraploid cell, or polyploid.

The method may further comprise purifying said multi-subunit complex from said host cells or from the culture medium.

Said multi-subunit complex may be purified from an intracellular component, cytoplasm, nucleoplasm, or a membrane of said host cells.

The desired multi-subunit complex may comprise an antibody, such as a monospecific or bispecific antibody. The antibody may be an antibody that specifically binds any antigen.

Said multi-subunit complex may comprise a human antibody or a humanized antibody or fragment thereof.

Said humanized antibody may be of mouse, rat, rabbit, goat, sheep, or cow origin.

Said humanized antibody may be of rabbit origin.

Said multi-subunit complex may comprise a monovalent, bivalent, or multivalent antibody.

Said antibody may be purified from said culture by protein A and/or protein G affinity.

At least one of the genes that provide for expression of a subunit of said multi-subunit complex in at least one of said eukaryotic cells in said panel may be optimized for expression in said eukaryotic cell.

The at least two host cells in said panel may comprise differing numbers of copies of a gene encoding the subunits of said multi-subunit complex, e.g., differing numbers of copies of a gene encoding a desired antibody heavy chain and/or said desired antibody light chain.

At least one host cell in said panel may comprise at least two copies of a gene encoding a subunit of said multi-subunit complex, e.g., at least two copies of a gene encoding a desired antibody heavy chain and/or said desired antibody light chain.

At least one host cell in said panel may comprise a gene encoding a subunit of said desired multi-subunit complex (such as a desired antibody heavy chain or a desired antibody light chain) whose expression may be driven by a different promoter than the promoter that drives the expression of the corresponding gene in a different host cell in said panel.

At least one host cell in said panel may comprise a polycistronic gene comprising more than one sequence encoding one or more subunits of said desired multi-subunit complex.

The desired multi-subunit complex may comprise a desired antibody, which may specifically bind to any antigen. Exemplary non-limiting examples include IL-6, TNF-alpha, CGRP, PCSK9, or NGF.

The desired multi-subunit complex may comprise an antibody of any type. Exemplary antibody types include antibodies of any mammalian species, e.g., human, mouse, rat, rabbit, goat, sheep, cow, etc. Preferably, the antibody is a human antibody or a humanized antibody that may be of rabbit origin. The desired antibody may be a monovalent, bivalent, or multivalent antibody.

At least one of said genes that provide for expression of a subunit of the desired multi-subunit complex, such as the light chain and/or heavy chain of a desired antibody, in at least one of said host cells in said panel may be optimized for expression in said host cell (e.g., by selecting preferred codons and/or altering the percentage AT through codon selection).

As shown in the working examples, in some embodiments, the yield and/or purity of the antibody is further optimized by the use of host cells for expression that have more copies of the heavy chain relative to the light chain, more copies of the light chain relative to the heavy chain, or equal numbers of copies of the light and heavy chains.

The purity of said desired multi-subunit complex, such as a desired antibody, may be assessed by measuring the fraction of the desired multi-subunit complex produced by said host cell that is non-glycosylated, is contained in complexes having the expected apparent hydrodynamic radius and/or apparent molecular weight (e.g., measured by size exclusion chromatography), has the expected electrophoretic mobility (e.g., detected by gel electrophoresis, such as SDS-PAGE, and optionally Western blotting), and/or by measuring the specific activity of the multi-subunit complex (e.g., specific binding a target of a desired antibody).

The desired multi-subunit complex may be an antibody, and yield of said antibody may be assessed by determining the amount of desired antibody produced by said host cell discounting any product-associated variants that are glycosylated, contained in antibody complexes other than complexes having the expected apparent molecular weight or hydrodynamic radius, and/or that fail to specifically bind to the target of said desired antibody.

In another aspect, the present disclosure provides a method of recombinantly producing a desired multi-subunit complex, such as a desired antibody, comprising: (a) providing a host cell comprising a gene encoding the light and heavy chains of said desired antibody, wherein said host cell is identified by any of the methods described herein as a host cell that produces a desired antibody with a greater yield and/or purity; and (b) culturing said host cell under conditions that permit expression of said light and heavy chain genes. The method may further comprise purification of said desired antibody.

In another aspect, the present disclosure provides a method of recombinantly producing a desired multi-subunit complex, such as a desired antibody, comprising: (a) providing a host cell comprising multiple copies of the genes encoding the light and heavy chains of said desired antibody, which host cell produces a desired antibody with a greater yield and/or purity relative to an isogenic host cell containing only a single copy of said genes encoding the light and heavy chains of said desired antibody; and (b) culturing said host cell under conditions that permit expression of said light and heavy chain genes. The method may further comprise purification of said desired antibody.

Said methods may further comprise culturing using methods and/or conditions as described in co-owned U.S. application Ser. No. 13/466,795, entitled "HIGH-PURITY PRODUCTION OF MULTI-SUBUNIT PROTEINS SUCH AS ANTIBODIES IN TRANSFORMED MICROBES SUCH AS *PICHIA PASTORIS*" and filed May 8, 2012, which is hereby incorporated by reference in its entirety. For example, said culturing may include addition of an ethanol bolus to the culture, e.g., to a final concentration of about 1% w/w.

For example, an aspect of the disclosure provides a method of producing a multi-subunit complex, comprising: (a) providing a culture comprising a eukaryotic cells comprising multiple copies of the genes that provide for the expression of the subunits of said multi-subunit complex; (b) adding a bolus of ethanol to said culture; and (c) culturing said culture to produce said multi-subunit complex.

The ethanol bolus may enhance the formation of stable disulfide bonds relative to the same method effected in the absence of the bolus of ethanol.

Said multi-subunit complex may contain one or more polypeptides comprising at least one disulfide bond.

Said multi-subunit complex may comprise an antibody.

The method may decrease the relative abundance of one or more product-associated variants relative to the same method effected in the absence of the bolus of ethanol.

The method may decrease the relative abundance of product-associated variants having a higher or lower apparent molecular weight than said desired multi-subunit complex as detected by size exclusion chromatography or gel electrophoresis relative to the same method effected in the absence of the bolus of ethanol.

The method may decrease the relative abundance of complexes having aberrant stoichiometry relative to the same method effected in the absence of the bolus of ethanol.

The method may decrease the relative abundance of complexes having aberrant disulfide bonds relative to the same method effected in the absence of the bolus of ethanol.

The method may decrease the relative abundance of complexes having reduced cysteines relative to the same method effected in the absence of the bolus of ethanol.

The method may decrease the relative abundance of complexes having aberrant glycosylation relative to the same method effected in the absence of the bolus of ethanol.

The method may modulate the formation or stability of inter-heavy chain disulfide bonds.

The method may modulate the formation or stability of disulfide bonds linking the light and heavy chains.

The method may decrease the relative abundance of one or more product-associated variants relative to the same method effected in the absence of the bolus of ethanol.

Said product-associated variants may comprise one or more of the H1L1, H2L1, and H4L4 product-associate variants.

The method increase the purity of said antibody relative to said method effected in the absence of said bolus of ethanol.

Step (b) may be effected prior to step (c).

Step (b) may be effected subsequent to step (c).

Step (b) may be effected concurrently with step (c).

Step (b) may result in a concentration of ethanol in said culture of between about 0.01% and about 4% (w/v).

Step (b) may result in a concentration of ethanol in said culture of between about 0.01% and about 4%, between about 0.02% and about 3.75%, between about 0.04% and about 3.5%, between about 0.08% and about 3.25%, between about 0.1% and about 3%, between about 0.2% and about 2.75%, between about 0.3% and about 2.5%, between about 0.4% and about 2.25%, between about 0.5% and about 2%, between about 0.6% and about 1.75%, between about 0.7% and about 1.5%, or between about 0.8% and about 1.25%.

Step (b) may result in a concentration of ethanol in said culture that may be at least about 0.01%, 0.02%, 0.03%, 0.04%, 0.05%, 0.06%, 0.07%, 0.08%, 0.09%, 0.10%, 0.2%, 0.3%, 0.4%, 0.6%, 0.6%, 0.7%, 0.8% or 0.9% (w/v).

Step (b) may result in a concentration of ethanol in said culture that may be at most about 4%, 3.5%, 3%, 2.5%, 2%, 1.8%, 1.6%, 1.5%, 1.4%, 1.3%, 1.2%, 1.1%, 1.0%, 0.9%, 0.8%, 0.7%, 0.6%, 0.5%, 0.4%, 0.35%, 0.3%, 0.25%, 0.2%, or 0.15% (w/v).

Step (b) may comprise adding ethanol to said culture, adding a carrier comprising ethanol to said culture, adding said cells to a medium or carrier comprising ethanol, or replacing part of the culture medium.

Said bolus of ethanol may be added to the culture medium over a period of time between 1 and 20 minutes.

Step (c) may comprise providing oxygen to said cells.

Said providing oxygen may comprise agitating said culture.

Said providing oxygen may comprise contacting said culture with a gas mixture comprising oxygen.

Step (c) may comprise adding a feed comprising a carbon source to said culture.

Said feed may comprise at least one fermentable carbon source.

Said feed may comprise one or more of glucose, ethanol, citrate, sorbitol, xylose, trehalose, arabinose, galactose, fructose, melibiose, lactose, maltose, rhamnose, ribose, mannose, mannitol, and raffinose.

The method may further comprise maintaining the concentration of ethanol between an upper set point and a lower set point during step (c).

Said lower set point may be about 0.01%, 0.02%, 0.03%, 0.04%, 0.05%, 0.06%, 0.07%, 0.08%, 0.09%, 0.10%, 0.2%, 0.3%, 0.4%, 0.6%, 0.6%, 0.7%, 0.8% or 0.9% (w/v).

Said upper set point may be about 4%, 3.5%, 3%, 2.5%, 2%, 1.8%, 1.6%, 1.5%, 1.4%, 1.3%, 1.2%, 1.1%, 1.0%, 0.9%, 0.8%, 0.7%, 0.6%, 0.5%, 0.4%, 0.35%, 0.3%, 0.25%, 0.2%, or 0.15% (w/v).

Said upper set point may be at most about 1.5%, 1.4%, 1.3, 1.2%, or 1.1% (w/v).

The method may further comprise maintaining the concentration of ethanol at a set point during step (c).

Said set point may be about 0.1%, 0.2%, 0.3%, 0.4%, 0.5%, 0.6%, 0.7%, 0.8%, 0.9%, 01.%, 01.1%, 01.2%, 01.3%, 01.4%, or 01.5% (w/v).

Step (c) may comprise maintaining the concentration of ethanol in said culture between about 0.01% and about 4%, between about 0.02% and about 3.75%, between about 0.04% and about 3.5%, between about 0.08% and about 3.25%, between about 0.1% and about 3%, between about 0.2% and about 2.75%, between about 0.3% and about 2.5%, between about 0.4% and about 2.25%, between about 0.5% and about 2%, between about 0.6% and about 1.75%, between about 0.7% and about 1.5%, or between about 0.8% and about 1.25%.

The concentration of ethanol in said culture may be maintained by controlling production of ethanol by said cells or by addition of ethanol to said culture.

The step of controlling production of ethanol may comprise controlling one or more of the concentration of glucose, availability of oxygen, intensity of agitation, gas pressure, flow rate of supplied air or other gas mixture, viscosity of the culture, culture density, concentration of oxygen in the supplied air or other gas mixture, and temperature.

The time between step (a) and step (b) may be less than about 72 hours, less than about 48 hours, less than about 24 hours, less than about 12 hours, less than about 9 hours, less than about 6 hours, less than about 5 hours, less than about 4 hours, less than about 3 hours, less than about 90 minutes, less than about 30 minutes, less than about 5 minutes, or less than about 1 minute.

The time between step (b) and step (c) may be less than about 10 hours, less than about 9 hours, less than about 8 hours, less than about 7 hours, less than about 6 hours, less than about 5 hours, less than about 4 hours, less than about 3 hours, less than about 2 hours, less than about 90 minutes, less than about 80 minutes, less than about 70 minutes, less than about 60 minutes, less than about 50 minutes, less than about 40 minutes, less than about 30 minutes, less than about 20 minutes, less than about 10 minutes, less than about 5 minutes, or less than about 1 minute.

The culture of step (a) may be produced by adding a carbon source to said culture, and culturing said culture until the carbon source may be depleted.

Said carbon source may comprise one or more of: glycerol, glucose, ethanol, citrate, sorbitol, xylose, trehalose, arabinose, galactose, fructose, melibiose, lactose, maltose, rhamnose, ribose, mannose, mannitol, and raffinose.

The depletion of the carbon source may be determined by detecting a decrease in the metabolic activity of said eukaryotic cells.

Said decrease in the metabolic activity of said eukaryotic cells may be identified by detecting a decrease in the consumption of oxygen by said eukaryotic cells, by detecting an increase in pH in the culture, by detecting stabilization of the wet cell mass, or by detecting an increase in the concentration of ammonia in the culture.

Said decrease in the consumption of oxygen by said eukaryotic cells may be identified by detecting an increase in the concentration of dissolved oxygen in said culture.

Said eukaryotic cells may comprise yeast cells.

Said yeast cells may comprise methylotrophic yeast.

Said methylotrophic yeast may be of the genus *Pichia*.

Said methylotrophic yeast of the genus *Pichia* may be *Pichia pastoris*.

Said methylotrophic yeast of the genus *Pichia* may be selected from the group consisting of: *Pichia angusta, Pichia guillermordii, Pichia methanolica*, and *Pichia inositovera*.

The genes that provide for expression of said multi-subunit complex may be integrated into one or more genomic loci.

At least one of said genomic loci may be selected from the group consisting of the pGAP locus, 3' AOX TT locus; PpURA5; OCH1; AOX1; HIS4; GAP; pGAP; 3' AOX TT; ARG; and the HIS4 TT locus.

At least one of the genes encoding said subunits of the multi-subunit complex may be expressed under control of an inducible or constitutive promoter.

Said inducible promoter may be selected from the group consisting of the AOX1, CUP1, tetracycline inducible, thiamine inducible, and FLD1 promoters.

At least one of the genes encoding said subunits of the multi-subunit complex may be expressed under control of a promoter selected from the group consisting of: the CUP1, AOX1, ICL1, glyceraldehyde-3-phosphate dehydrogenase (GAP), FLD1, ADH1, alcohol dehydrogenase II, GAL4, PHO3, PHO5, and Pyk promoters, tetracycline inducible promoters, thiamine inducible promoters, chimeric promoters derived therefrom, yeast promoters, mammalian promoters, insect promoters, plant promoters, reptile promoters, amphibian promoters, viral promoters, and avian promoters.

Said eukaryotic cell may be a diploid, tetraploid cell, or polyploid.

The method may further comprise purifying said multi-subunit complex from said eukaryotic cells or from the culture medium.

Said multi-subunit complex may be purified from an intracellular component, cytoplasm, nucleoplasm, or a membrane of said eukaryotic cells.

Said eukaryotic cells secrete said multi-subunit complex into the culture medium.

Said multi-subunit complex may be purified from said culture medium.

Said multi-subunit complex may comprise a monospecific or bispecific antibody.

Said multi-subunit complex may comprise a human antibody or a humanized antibody or fragment thereof.

Said humanized antibody may be of mouse, rat, rabbit, goat, sheep, or cow origin.

Said humanized antibody may be of rabbit origin.

Said multi-subunit complex may comprise a monovalent, bivalent, or multivalent antibody.

Said antibody may be purified from said culture by protein A and/or protein G affinity.

At least one of the genes that provide for expression of a subunit of said multi-subunit complex in at least one of said eukaryotic cells in said panel may be optimized for expression in said eukaryotic cell.

Said multi-subunit complex may comprise an antibody and the purity of said antibody may be assessed by measuring the fraction of the antibody produced by said eukaryotic cell that may be contained in antibody complexes having the expected apparent hydrodynamic radius, may be contained in antibody complexes having the expected molecular weight, and/or specifically binds a target of said antibody.

Said multi-subunit complex may comprise an antibody and the yield of said antibody may be assessed by determining the amount of antibody produced by said eukaryotic cell discounting any product-associated variants that may be abnormally glycosylated, contained in antibody complexes other than complexes having the expected apparent hydrodynamic radius, contained in antibody complexes having the expected molecular weight, and/or that fail to specifically bind to the target of said antibody.

The molecular weight of said antibody complexes may be determined by non-reducing SDS-PAGE.

Said multi-subunit complex may comprise an antibody, said method may further comprise purifying said antibody.

Said culture cell may produce a supernatant antibody titer of at least 100 mg/L, at least 150 mg/L, at least 200 mg/L, at least 250 mg/L, at least 300 mg/L, between 100 and 300 mg/L, between 100 and 500 mg/L, between 100 and 1000 mg/L, at least 1000 mg/L, at least 1250 mg/liter, at least 1500 mg/liter, at least about 1750 mg/liter, at least about 2000 mg/liter, at least about 10000 mg/liter, or more.

One or more subunits of said multi-subunit complex may be expressed from more than one gene copy.

Said multi-subunit complex may comprise an antibody which may be expressed from between 1-10 copies of a gene encoding the light chain of said antibody and from 1-10 copies of a gene encoding the heavy chain of said antibody.

The genes that provide for expression of said multi-subunit complex may be integrated into genome of said cells.

The genes that provide for expression of said multi-subunit complex may be contained on an extrachromosomal element, plasmid, or artificial chromosome.

Said cells may comprise more copies of the gene that provide for the expression of the light chain of said antibody than copies of the gene that provide for expression of the heavy chain of said antibody.

The respective number of copies of the gene encoding the heavy chain of said antibody and the number of copies of the gene encoding the light chain of said antibody in said cells may be: 2 and 2, 2 and 3, 3 and 3, 3 and 4, 3 and 5, 4 and 3, 4 and 4, 4 and 5, 4 and 6, 5 and 4, 5 and 5, 5 and 6, or 5 and 7.

The respective number of copies of the gene encoding the heavy chain of said antibody and the number of copies of the gene encoding the light chain of said antibody in said cells may be: 2 and 1, 3 and 1, 4 and 1, 5 and 1, 6 and 1, 7 and 1, 8 and 1, 9 and 1, 10 and 1, 1 and 2, 2 and 2, 3 and 2, 4 and 2, 5 and 2, 6 and 2, 7 and 2, 8 and 2, 9 and 2, 10 and 2, 1 and 3, 2 and 3, 3 and 3, 4 and 3, 5 and 3, 6 and 3, 7 and 3, 8 and 3, 9 and 3, 10 and 3, 1 and 4, 2 and 4, 3 and 4, 4 and 4, 5 and 4, 6 and 4, 7 and 4, 8 and 4, 9 and 4, 10 and 4, 1 and 5, 2 and 5, 3 and 5, 4 and 5, 5 and 5, 6 and 5, 7 and 5, 8 and 5, 9 and 5, 10 and 5, 1 and 6, 2 and 6, 3 and 6, 4 and 6, 5 and 6, 6 and 6, 7 and 6, 8 and 6, 9 and 6, 10 and 6, 1 and 7, 2 and 7, 3 and 7, 4 and 7, 5 and 7, 6 and 7, 7 and 7, 8 and 7, 9 and 7, 10 and 7, 1 and 8, 2 and 8, 3 and 8, 4 and 8, 5 and 8, 6 and 8, 7 and 8, 8 and 8, 9 and 8, 10 and 8, 1 and 9, 2 and 9, 3 and 9, 4 and 9, 5 and 9, 6 and 9, 7 and 9, 9 and 9, 9 and 9, 10 and 9, 1 and 10, 2 and 10, 3 and 10, 4 and 10, 5 and 10, 6 and 10, 7 and 10, 8 and 10, 9 and 10, 10 and 10.

The culture of step (c) may be grown in a production medium.

Said production medium may be a minimal medium.

Said minimal medium lacks selective agents.

Said minimal medium lacks pre-formed amino acids or other complex biomolecules.

The production medium may be a complex medium.

The complex medium may comprise one or more of yeast extract, soy peptones, and other plant peptones.

The culture of step (c) may be grown to a high cell density.

Said high cell density may be at least 50 g/L.
Said high cell density may be at least 100 g/L.
Said high cell density may be at least 300 g/L.
Said high cell density may be at least 400 g/L.
Said high cell density may be at least 500 g/L.
Said high cell density may be at least 750 g/L.

The yeast cells may be cultured for at least 20 doublings and maintain high levels of expression of said multi-subunit complex after said at least 20 doublings.

The cells of step (c) may be cultured for at least 50 doublings and maintain high levels of expression of said multi-subunit complex after said at least 50 doublings.

The cells of step (c) may be cultured for at least 100 doublings and maintain high levels of expression of said multi-subunit complex after said at least 100 doublings.

At least one subunit of said multi-subunit complex may comprise a secretion signal.

Said multi-subunit complex may comprise an antibody.

The subject methods may produce a supernatant antibody titer of at least 100 mg/L, at least 150 mg/L, at least 200 mg/L, at least 250 mg/L, at least 300 mg/L, between 100 and 300 mg/L, between 100 and 500 mg/L, between 100 and 1000 mg/L or in excess of 1000 mg/L e.g., as high as 1200 mg/L, as high as 10,000 mg/L, or higher.

In another aspect, the present disclosure provides a host cell identified by any of the foregoing methods as a host cell that produces a desired multi-subunit complex, such as a desired antibody, with a greater yield and/or purity. The host cell may be a diploid or tetraploid cell of the genus Pichia, such as a Pichia pastoris cell. In another aspect, the present disclosure provides a diploid or tetraploid yeast culture derived from the aforementioned host cell. The genes that provide for expression of the subunits of said desired multi-subunit complex, such as the light chain and heavy chain of a desired antibody, may be integrated into genome of said host cell. The genes that provide for expression of the subunits of said desired multi-subunit complex, such as the light chain and heavy chain of a desired antibody, may be contained on an extrachromosomal element, plasmid, or artificial chromosome. Where the desired multi-subunit complex is an antibody, the host cell may comprise more copies of the gene that provide for the expression of the light chain than copies of the gene that provide for expression of the heavy chain. In exemplary embodiments, the host cell may comprise from 1-10 copies of a gene encoding the light chain and from 1-10 copies of a gene encoding the heavy chain. The respective number of copies of the gene encoding the heavy chain and the number of copies of the gene encoding the light chain in said host cell may be: 2 and 2, 2 and 3, 3 and 3, 3 and 4, 3 and 5, 4 and 3, 4 and 4, 4 and 5, 4 and 6, 5 and 4, 5 and 5, 5 and 6, or 5 and 7, respectively. Additional exemplary combinations of heavy and light chain gene copy numbers are enumerated in FIG. 37, which enumerates combinations having up to ten copies of the heavy and/or light chain gene, including strains having the identifiers H2×L1, H3×L1, H4×L1, H5×L1, H6×L1, H7×L1, H8×L1, H9×L1, H10×L1, H1×L2, H2×L2, H3×L2, H4×L2, H5×L2, H6×L2, H7×L2, H8×L2, H9×L2, H10×L2, H1×L3, H2×L3, H3×L3, H4×L3, H5×L3, H6×L3, H7×L3, H8×L3, H9×L3, H10×L3, H1×L4, H2×L4, H3×L4, H4×L4, H5×L4, H6×L4, H7×L4, H8×L4, H9×L4, H10×L4, H1×L5, H2×L5, H3×L5, H4×L5, H5×L5, H6×L5, H7×L5, H8×L5, H9×L5, H10×L5, H1×L6, H2×L6, H3×L6, H4×L6, H5×L6, H6×L6, H7×L6, H8×L6, H9×L6, H10×L6, H1×L7, H2×L7, H3×L7, H4×L7, H5×L7, H6×L7, H7×L7, H8×L7, H9×L7, H10×L7, H1×L8, H2×L8, H3×L8, H4×L8, H5×L8, H6×L8, H7×L8, H8×L8, H9×L8, H10×L8, H1×L9, H2×L9, H3×L9, H4×L9, H5×L9, H6×L9, H7×L9, H8×L9, H9×L9, H10×L9, H1×L10, H2×L10, H3×L10, H4×L10, H5×L10, H6×L10, H7×L10, H8×L10, H9×L10, H10×L10. For example, the specified number of heavy and light chain gene copies may be tandemly integrated into a single locus, or into multiple loci (any or all of which may contain more than one copy). Optionally, each genomic locus may contain no more than three or four tandemly integrated gene copies, thereby promoting copy number stability during propagation and/or antibody production.

Culturing most typically involves proving cells with an energy source, oxygen, and nutrients. Methods are also known in the literature for design and optimization of P. pastoris fermentations for expression of recombinant proteins, including optimization of the cell density, broth volume, substrate feed rate, and the length of each phase of the reaction. See Zhang et al., "Rational Design and Optimization of Fed-Batch and Continuous Fermentations" in Cregg, J. M., Ed., 2007, Pichia Protocols (2nd edition), Methods in Molecular Biology, vol. 389, Humana Press, Totowa, N.J., pgs. 43-63. The culture may be provided with a gas mixture comprising oxygen, such as air with or without oxygen supplementation. The yeast culture may be cultured in a culture medium which may be a minimal medium, may lack selective agents, and/or may lack pre-formed amino acids or other complex biomolecules. The culture medium may also be a complex medium (e.g., containing yeast extract and/or plant peptone(s)). The medium may include a nitrogen source (e.g., methylamine chloride, NH4SO4, yeast extract, soy peptone, other plant peptones, etc.). Exemplary minimal media include minimal dextrose medium (MD) (1.34% yeast nitrogen base (YNB) (w/o amino acids), $4\times10^{-5}$% biotin, and 2% glucose.), buffered minimal glycerol complex medium (BMGY) (1% yeast extract, 2% peptone, 1% glycerol, 1.34% YNB (w/o amino acids), 4×10-5% biotin and 100 mM potassium phosphate (pH 6.0)). Media may include one or more salts (such as sodium chloride, calcium, magnesium, and phosphate), buffers (such as potassium phosphate, Tris, or HEPES), nucleosides (such as adenosine and thymidine), antibiotics (e.g., added to inhibit growth of contaminants and/or for maintenance of a selectable marker), trace elements, and glucose or another energy source. Any supplements and substitutions may also be included at appropriate concentrations that would be known to those skilled in the art.

The culture may be grown to a high cell density, such as at least 50 g/L, at least 100 g/L, at least 300 g/L, at least 400 g/L, at least 500 g/L, or at least 700 g/L. These culture densities are illustrative rather than limiting, and suitable culture densities may be readily determined by those of ordinary skill in the art.

The yeast cells may be cultured for at least 20 doublings and maintain high levels of expression of said antibody after said at least 20 doublings.

The yeast cells may be cultured for at least 50 doublings and maintain high levels of expression of said antibody after said at least 50 doublings.

The yeast cells may be cultured for at least 100 doublings and maintain high levels of expression of said antibody after said at least 100 doublings.

In another aspect, the present disclosure provides a culture medium containing a stable diploid Pichia yeast culture produced according to any of the foregoing methods, wherein the culture medium may comprise expression levels of said desired antibody which may be at least about 50 mg/liter, 100 mg/liter, 500 mg/liter, 750 mg/liter, 1000 mg/liter, 1250 mg/liter, 1500 mg/liter, 1750 mg/liter, 2000 mg/liter, or more. These yield values are illustrative rather than limiting. Optionally, yield may be optimized, for example using the methods and general approach described in Zhang et al. (2007), supra. For example, yield may be optimized by varying temperature, pH, media composition (e.g., carbon source, carbon source concentration, mixture of two or more carbon sources, nitrogen source and concentration, concentration of salts and nutrients including $KH_2PO_4$, $K_2HPO_4$, $MgSO_4$, potassium sulfate, sodium citrate, potassium sulfate, sodium citrate, trace metals such as cobalt chloride, cupric sulfate, sodium iodide, manganese sulfate, sodium molybdate, boric acid, zinc chloride, ferrous sulfate, vitamins such as biotin, inositol, thiamine, peptone, yeast extract, casamino acids, urea, ammonium phosphate or other ammonium ions, L-arginine-hydrochloride), time, culture density, oxygenation, and other factors that influence yield. For example, yield, expression, and/or purity of the desired multi-subunit complex may in some instances be improved by maintaining the temperature at a desired set point, e.g., a set point between about 15° C. and about 30° C., such as between about 17° C. and about 25° C.). Without intent to be limited by theory, it is hypothesized that controlling the temperature may assist intracellular trafficking through the folding and post-translational processing pathways, and/or may decrease the activity of cellular proteases. Likewise, yield, expression, and/or purity of the desired multi-subunit complex may in some instances be improved by maintaining the pH of the culture medium at a desired set point, e.g., a set point between pH 3 to pH 8, such as between pH 4 and pH 7.

In another aspect, the present disclosure provides a culture medium containing a stable diploid *Pichia pastoris* yeast culture derived from a cell produced according to any of the foregoing methods that expresses said desired antibody into a culture medium wherein the cell density of said diploid cells in said culture may be at least about 50 g/L, 100 g/L, 300 g/L, 400 g/L, 500 g/L, 700 g/L or more. These culture densities are illustrative rather than limiting, and suitable culture densities may be readily determined by those of ordinary skill in the art.

At least one subunit of said antibody or other multi-subunit protein may comprise a secretion signal, such as the S. chicken lysozyme (CLY) signal peptide; CLY-L8; *S. cerevisiae* invertase (SUC2) signal peptide; MF-alpha (Prepro); MF-alpha (Pre)-apv; MF-alpha (Pre)-apv-SLEKR; MF-alpha (Prepro)-(EA)3; αF signal peptide; KILM1 signal peptide; repressible acid phosphatase (PHO1) signal peptide; *A. niger* GOX signal peptide; *Schwanniomyces occidentalis* glucoamylase gene (GAM1) signal peptide; human serum albumin (HSA) signal peptide without pro-sequence; human serum albumin (HSA) signal peptide with pro-sequence; ISN signal peptide; IFN signal peptide; HGH signal peptide; phytohaemagglutinin (PHA); Silkworm lysozyme; Human lysozyme (LYZ1); activin receptor type-1; activin type II receptor; *P. pastoris* immunoglobulin binding protein (PpBiP); human antibody 3D6 light chain leader; and any combination thereof.

The host cell may be produced by mating two haploid yeast cells that each contain one or more copies of a gene encoding one or more subunits of said antibody or other multi-subunit protein.

BRIEF DESCRIPTION OF THE DRAWINGS

FIG. 1 provides an overview of an exemplary methodology for obtaining haploid strains containing a specifically targeted number of copies of genes encoding a desired antibody light chain and/or heavy chain, and of mating haploid strains to obtain a panel of diploid strains that express the desired antibody from a specifically targeted number of copies of the light and heavy chain genes.

FIG. 2 graphically illustrates relative whole antibody yield in comparison to the H3×L3 strain from selected diploid strains containing increasing numbers of copies of genes encoding the light and heavy chains of Ab-A. Setting the H3×L3 yield at 100%, the relative whole broth antibody titer generally increased with increasing antibody total copy number, in the order H3×L4, H3×L3, H4×L4, H4×L6, H5×L4, H5×L5, and H5×L7.

FIG. 3 graphically illustrates relative whole broth antibody yield in comparison to the H3×L3 strain from strains containing increasing numbers of copies of genes encoding the light and heavy chains of Ab-B. Setting the H3×L3 antibody yield at 100%, the relative whole broth antibody titer generally increased with increasing antibody copy number, in the order H3×L3, H3×L4, H4×L3, H4×L5, and H4×L6.

FIG. 4 graphically illustrates relative whole broth antibody yield in comparison to the H3×L3 strain from strains containing increasing numbers of copies of genes encoding the light and heavy chains of Ab-C. Setting the H3×L3 antibody yield at 100%, the relative whole broth antibody titer generally increased with increasing antibody copy number, in the order Ab-C-H3×L4, Ab-C-H4×L3, Ab-C-H4×L4, Ab-C-H4×L5, Ab-C-H5×L5, Ab-C-H5×L4, Ab-C-H5×L6, and Ab-C-H6×L5.

FIG. 8 shows a stained SDS-PAGE gel of Ab-A produced from H4×L4 and H4×L6 strains. An observed "low-mobility product-associated variant" (arrow) was less abundant in the preparation from the strain with the higher light chain copy number.

FIG. 9 shows a stained SDS-PAGE gel of Protein-A purified Ab-B produced from strains H4×L5 and H4×L6. As with Ab-A, an observed "low-mobility product-associated variant" (arrow) was less abundant in the preparation from the strain with the higher light chain copy number.

FIG. 10 shows a stained SDS-PAGE gel of Protein-A purified Ab-C produced from strains H3×L3 and H5×L5. As with Ab-A and Ab-B, an observed "low-mobility product-associated variant" (arrow) was less abundant in the preparation from the strain with the higher antibody chain copy number.

FIG. 11 shows identification of the low-mobility product-associated variant as a glycosylated protein related to human Fc (demonstrated by its selective enrichment by a lectin column and specific recognition by an anti-Fc antibody). An antibody preparation ("Load") was bound to a lectin resin and eluted ("Lectin Eluate"). SDS-PAGE (FIG. 11A) demonstrated selective enrichment of the low-mobility product-associated variant by the lectin column. Western blotting with an anti-HuFc antibody (FIG. 11A) detected the low-mobility product-associated variant, indicating that it contained at least a partial human Fc sequence. This product-associated variant is referred to herein as the "glyco-heavy variant." Additionally, the amount of this product-associated variant was visibly reduced in the antibody preparation from strain H4×L5 relative to strain H4×L3.

FIG. 22 illustrates the relationship between antibody copy number integrated at a single locus and the expected fragment sizes detectable by Southern blot.

FIGS. 23 and 24 show Southern blots used to detect the number of copies of an antibody heavy chain gene and light chain gene, respectively, in multiple isolates transformed with genes encoding Ab-A chains.

FIGS. 25-27 show Southern blots used to confirm the number of copies of the genes encoding the Ab-A heavy and light chains present at the pGAP (FIGS. 25-26) and HIS4 TT (FIG. 27) loci in a panel of diploid strains produced by mating transformed haploid strains.

FIG. 28A-B shows Southern blots used to detect the number of copies of the antibody heavy chain gene and light chain genes, respectively, in multiple isolates transformed with genes encoding Ab-B chains.

FIGS. 29-31 show Southern blots that confirmed the number of copies of the genes encoding the Ab-B heavy and light chains present at the pGAP (FIGS. 29-30) and HIS4 TT (FIG. 31) loci in a panel of diploid strains produced by mating transformed haploid strains.

FIGS. 32-33 show Southern blots used to detect the number of copies of the antibody heavy chain and light chain genes, respectively, in multiple isolates transformed with genes encoding the Ab-C chains.

FIGS. 34-36 show Southern blots that confirmed the number of copies of the genes encoding the Ab-C heavy and light chains present at the 3' AOX TT (FIGS. 34-35) and HIS4 TT (FIG. 36) loci in a panel of diploid strains produced by mating transformed haploid strains.

FIG. 37 illustrates exemplary, non-limiting combinations of light and heavy chain gene copy numbers that may be used in accordance with embodiments of the present disclosure.

FIG. 38 shows the sequence of polynucleotides encoding the Ab-A light and heavy chains and the polypeptides they encode, as well as CDR sequences contained therein.

FIG. 39 shows the sequence of polynucleotides encoding the Ab-B light and heavy chains and the polypeptides they encode, as well as CDR sequences contained therein.

FIG. 40 shows the sequence of polynucleotides encoding the Ab-C light and heavy chains and the polypeptides they encode.

DETAILED DESCRIPTION

Figure 5:
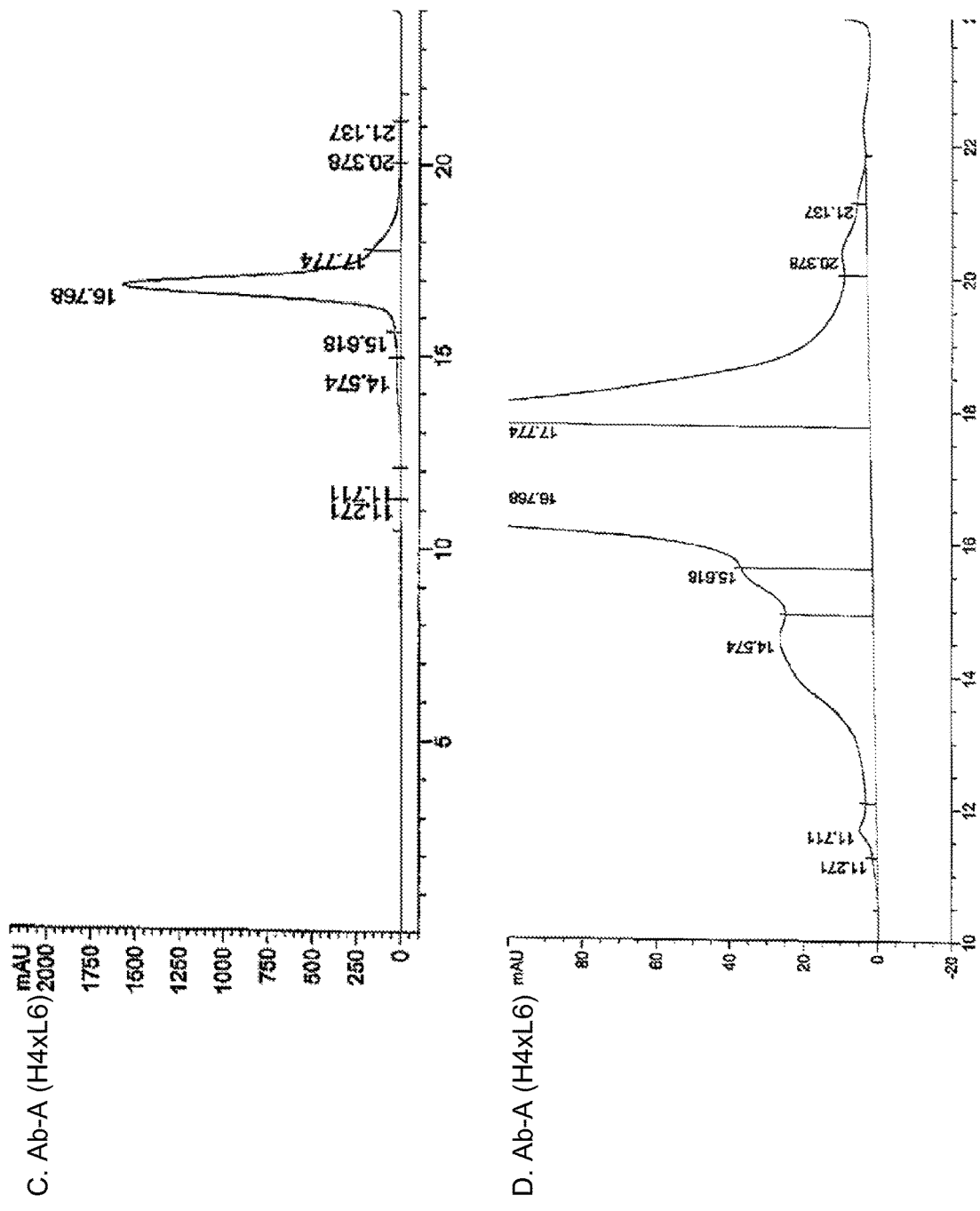
FIG. 5A-E shows the purity of protein-A capture eluate of Ab-A produced from H4×L4 and H4×L6 strains determined by HPLC. The level of the product-associated variant (measured by the percentage of total integrated area) migrating at 15.5 min, was decreased by more than five-fold (from 8.81 in H4×L4 down to 1.58% in H4×L6).

The present disclosure provides methods of generating and identifying host cells able to produce an increased yield of a desired heterologous multi-subunit complex and/or produce a desired heterologous multi-subunit complex having improved purity. In a preferred embodiment, the heterologous multi-subunit complex is an antibody or antibody fragment, such as a humanized antibody, comprised of two heavy chain subunits and two light chain subunits. Preferred host cells include yeasts, and particularly preferred yeasts include methylotrophic yeast strains, e.g., Pichia pastoris, Hansenula polymorphs (Pichia angusta), Pichia guillermordii, Pichia methanolica, Pichia inositovera, and others (see, e.g., U.S. Pat. Nos. 4,812,405, 4,818,700, 4,929,555, 5,736,383, 5,955,349, 5,888,768, and 6,258,559 each of which is incorporated by reference in its entirety). The host cell may be produced by methods known in the art. For example, a panel of diploid or tetraploid yeast cells containing differing combinations of gene copy numbers may be generated by mating cells containing varying numbers of copies of the individual subunit genes (which numbers of copies preferably are known in advance of mating).

Applicants have unexpectedly discovered that cultures can maintain a high stable copy number of the genes encoding the desired multi-subunit complex. The working examples demonstrate cells which maintain up to six or seven copies of antibody heavy and light chain-encoding genes. These cells can stably express the desired antibody even over a prolonged culture duration. Additionally, the cells can maintain high yield and expression of the desired multi-subunit complex even after a prolonged culture duration.

In a preferred embodiment, the host cell may comprise more than one copy of one or more of the genes encoding the heterologous protein subunits. For example, multiple copies of a subunit gene may be integrated in tandem into one or more chromosomal loci. Tandemly integrated gene copies are preferably retained in a stable number of copies during culture for the production of the multi-subunit complex. For example, in the examples described below, gene copy numbers were generally stable for P. pastoris strains containing three to four tandemly integrated copies of light and heavy chain antibody genes.

One or more of the genes encoding the heterologous protein subunits are preferably integrated into one or more chromosomal loci of a host cell. Any suitable chromosomal locus may be utilized for integration, including intergenic sequences, promoters sequences, coding sequences, termination sequences, regulatory sequences, etc. Exemplary chromosomal loci that may be used in *P. pastoris* include PpURA5; OCH1; AOX1; HIS4; and GAP. The encoding genes may also be integrated into one or more random chromosomal loci rather than being targeted. In preferred embodiments, the chromosomal loci are selected from the group consisting of the pGAP locus, the 3'AOX TT locus and the HIS4 TT locus. In additional exemplary embodiments, the genes encoding the heterologous protein subunits may be contained in one or more extrachromosomal elements, for example one or more plasmids or artificial chromosomes.

In exemplary embodiments, the multi-subunit protein may comprise two, three, four, five, six, or more non-identical subunits. Additionally, each subunit may be present one or more times in each multi-subunit protein. For example, the multi-subunit protein may be a multi-specific antibody such as a bi-specific antibody comprising two non-identical light chains and two non-identical heavy chains. A panel of diploid or tetraploid yeast cells containing differing combinations of gene copy numbers may be quickly generated by mating cells containing varying copy numbers of the individual subunit genes. Antibody production from each strain in the panel may then be assessed to identify a strain for further use based on a characteristic such as yield of the desired multi-subunit protein or purity of the desired multi-subunit protein relative to undesired side-products.

The subunits may be expressed from monocistronic genes, polycistronic genes, or any combination thereof. Each polycistronic gene may comprise multiple copies of the same subunit, or may comprise one or more copies of each different subunit.

Exemplary methods that may be used for manipulation of *Pichia pastoris* (including methods of culturing, transforming, and mating) are disclosed in Published applications including U.S. 20080003643, U.S. 20070298500, and U.S. 20060270045, and in Higgins, D. R., and Cregg, J. M., Eds. 1998. *Pichia* Protocols. Methods in Molecular Biology. Humana Press, Totowa, N.J., and Cregg, J. M., Ed., 2007, *Pichia* Protocols (2nd edition), Methods in Molecular Biology. Humana Press, Totowa, N.J., each of which is incorporated by reference in its entirety.

An exemplary expression cassette that may be utilized is composed of the glyceraldehyde dehydrogenase gene (GAP gene) promoter, fused to sequences encoding a secretion signal, followed by the sequence of the gene to be expressed, followed by sequences encoding a *P. pastoris* transcriptional termination signal from the *P. pastoris* alcohol oxidase I gene (AOX1). The Zeocin resistance marker gene may provide a means of enrichment for strains that contain multiple integrated copies of an expression vector in a strain by selecting for transformants that are resistant to higher levels of Zeocin. Similarly, G418 or Kanamycin resistance marker genes may be used to provide a means of enrichment for strains that contain multiple integrated copies of an expression vector in a strain by selecting for transformants that are resistant to higher levels of Geneticin or Kanamycin.

Host strains that may be utilized include auxotrophic *P. pastoris* or other *Pichia* strains, for example, strains having mutations in met1, lys3, ura3 and ade1 or other auxotrophy-associated genes. Preferred mutations are incapable of giving rise to revertants at any appreciable frequency and are preferably partial or even more preferably full deletion mutants. Preferably, prototrophic diploid or tetraploid strains are produced by mating a complementing sets of auxotrophic strains.

Transformation of haploid *P. pastoris* strains and genetic manipulation of the *P. pastoris* sexual cycle may be performed as described in *Pichia* Protocols (1998, 2007), supra.

Prior to transformation, each expression vector may be linearized by restriction enzyme cleavage within a region homologous to the target genomic locus (e.g., the GAP promoter sequence) to direct the integration of the vectors into the target locus in the host cell. Samples of each vector may then be individually transformed into cultures of the desired strains by electroporation or other methods, and successful transformants may be selected by means of a selectable marker, e.g., antibiotic resistance or complementation of an auxotrophy. Isolates may be picked, streaked for single colonies under selective conditions and then examined to confirm the number of copies of the gene encoding the subunit of the multi-subunit complex (e.g., a desired antibody) by Southern Blot or PCR assay on genomic DNA extracted from each strain. Optionally, expression of the expected subunit gene product may be confirmed, e.g., by FACS, Western Blot, colony lift and immunoblot, and other means known in the art. Optionally, haploid isolates are transformed additional times to introduce additional heterologous genes, e.g., additional copies of the same subunit integrated at a different locus, and/or copies of a different subunit. The haploid strains are then mated to generate diploid strains (or strains of higher ploidy) able to synthesize the multi-protein complex. Presence of each expected subunit gene may be confirmed by Southern blotting, PCR, and other detection means known in the art. Where the desired multi-protein complex is an antibody, its expression may also be confirmed by a colony lift/immunoblot method (Wung et al. Biotechniques 21 808-812 (1996) and/or by FACS.

This transformation protocol is optionally repeated to target a heterologous gene into a second locus, which may be the same gene or a different gene than was targeted into the first locus. When the construct to be integrated into the second locus encodes a protein that is the same as or highly similar to the sequence encoded by the first locus, its sequence may be varied to decrease the likelihood of undesired integration into the first locus. For example, the sequence to be integrated into the second locus may have differences in the promoter sequence, termination sequence, codon usage, and/or other tolerable sequence differences relative to the sequence integrated into the first locus.

To mate *P. pastoris* haploid strains, each strain to be crossed can be patched together onto mating plates. For example, multiple matings can be conveniently performed at the same time by streaking each strain to be mated across a plate suitable for its growth, and the mating partners may be streaked across a second plate (preferably the plates are rich media such as YPD). Typically, after one or two days incubation at 30° C., cells from the two plates can be replica plated in a crisscross fashion onto a mating plate, resulting in a cross-hatched pattern with each pair of strains being co-plated and having the opportunity to mate at the intersection of a pair of the original streak lines. The mating plate can then be incubated (e.g., at 30° C.) to stimulate the initiation of mating between strains. After about two days, the cells on the mating plates can be streaked, patched, or replica plated onto media selective for the desired diploid strains (e.g., where the mated strains have complementary autotrophies, drop-out or minimal medium plates may be used). These plates can be incubated (e.g., at 30° C.) for a suitable duration (e.g., about three days) to allow for the selective growth of the desired diploid strains. Colonies that arise can be picked and streaked for single colonies to isolate and purify each diploid strain.

Expression vectors for use in the methods of the invention may further include yeast specific sequences, including a selectable auxotrophic or drug marker for identifying transformed yeast strains. A drug marker may further be used to amplify copy number of the vector in a yeast host cell, e.g., by culturing a population of cells in an elevated concentration of the drug, thereby selecting transformants that express elevated levels of the resistance gene.

In an exemplary embodiment, one or more of the genes encoding the heterologous protein subunits are coupled to an inducible promoter. Suitable exemplary promoters include the alcohol oxidase 1 gene promoter, formaldehyde dehydrogenase genes (FLD; see U.S. Pub. No. 2007/0298500), and other inducible promoters known in the art. The alcohol oxidase 1 gene promoter, is tightly repressed during growth of the yeast on most common carbon sources, such as glucose, glycerol, or ethanol, but is highly induced during growth on methanol (Tschopp et al., 1987; U.S. Pat. No. 4,855,231 to Stroman, D. W., et al). For production of foreign proteins, strains may be initially grown on a repressing carbon source to generate biomass and then shifted to methanol as the sole (or main) carbon and energy source to induce expression of the foreign gene. One advantage of this regulatory system is that *P. pastoris* strains transformed with foreign genes whose expression products are toxic to the cells can be maintained by growing under repressing conditions.

In another exemplary embodiment, one or more of the heterologous genes may be coupled to a regulated promoter, whose expression level can be upregulated under appropriate conditions. Exemplary regulated promoters include the CUP1 promoter (induced by the level of copper in the medium), tetracycline inducible promoters, thiamine inducible promoters, the AOX1 promoter, and the FLD1 promoter.

Though much of the present disclosure describes production of antibodies, the methods described herein are readily adapted to other multi-subunit complexes as well. Without intent to be limited by theory, it is believed that the yield and purity of multi-subunit complexes can be greatly influenced by the concentration and stoichiometry of the subunits, which are in turn influenced by the level of expression of the genes responsible for production of each subunit. The methods disclosed herein may readily be utilized to improve the yield and/or purity of any recombinant multi-subunit complex comprising two or more different subunits. Additionally, the present methods are not limited to production of multi-protein complexes but may also be readily adapted for use with ribonucleoprotein (RNP) complexes including telomerase, hnRNPs, Ribosomes, snRNPs, signal recognition particles, prokaryotic and eukaryotic RNase P complexes, and any other complexes that contain multiple distinct protein and/or RNA subunits. The host cell that expresses the multi-subunit complex may be produced by methods known in the art. For example, a panel of diploid or tetraploid yeast cells containing differing combinations of gene copy numbers may be generated by mating cells containing varying numbers of copies of the individual subunit genes (which numbers of copies preferably are known in advance of mating).

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Bolus addition: In the present disclosure, "bolus addition" generally refers to rapid change in concentration of a substance (such as ethanol) in contact with cultured cells (for example, in a culture medium). For example, the substance may be added to the cultured cells in a single addition, a succession of more than one addition, and/or infused over a period of time (e.g., over about 1, 2, 3, 4, 5, 6, 7, 8, 9, 10, 15, 20, 25, 30, 40, 50, 60, 90, or 120 minutes). The substance may also be added by replacing the culture medium in part or in full, for example by concentrating the cells (using centrifugation, filtration, settling, or other methods), removing part or all of the medium, and adding the substance, or by adding the cells to a medium containing the substance. The substance may be admixed with a carrier (e.g., culture media, water, saline, etc.). For example, a bolus addition of ethanol may comprise the addition of pure or concentrated ethanol (e.g., 100%, 95%, 70%, 50%, 60%, 40%, 30%, 20%, etc.) to the culture medium in an amount sufficient to produce the desired concentration. As another example, the cells may be added to a medium containing ethanol, e.g., by adding an inoculum containing the cells to a medium containing ethanol.

Bolus concentration: In the present disclosure, "bolus concentration" generally refers to the concentration that results from a bolus addition of a substance (e.g., ethanol).

Mating competent yeast species: In the present invention this is intended to broadly encompass any diploid or tetraploid yeast which can be grown in culture. Such species of yeast may exist in a haploid, diploid, or other polyploid form. The cells of a given ploidy may, under appropriate conditions, proliferate for an indefinite number of generations in that form. Diploid cells can also sporulate to form haploid cells. Sequential mating can result in tetraploid strains through further mating or fusion of diploid strains. The present invention contemplates the use of haploid yeast, as well as diploid or other polyploid yeast cells produced, for example, by mating or fusion (e.g., spheroplast fusion).

In one embodiment of the invention, the mating competent yeast is a member of the Saccharomycetaceae family, which includes the genera *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Tetrapisispora; Torulaspora; Williopsis*; and *Zygosaccharomyces*. Other types of yeast potentially useful in the invention include *Yarrowia; Rhodosporidium; Candida; Hansenula; Filobasium; Sporidiobolus; Bullera; Leucosporidium* and *Filobasidella*.

In a preferred embodiment of the invention, the mating competent yeast is a member of the genus *Pichia* or is another methylotroph. In a further preferred embodiment of the invention, the mating competent yeast of the genus

*Pichia* is one of the following species: *Pichia pastoris, Pichia methanolica*, and *Hansenula* polymorphs (*Pichia angusta*). In a particularly preferred embodiment of the invention, the mating competent yeast of the genus *Pichia* is the species *Pichia pastoris*.

Haploid Yeast Cell: A cell having a single copy of each gene of its normal genomic (chromosomal) complement.

Polyploid Yeast Cell: A cell having more than one copy of its normal genomic (chromosomal) complement.

Diploid Yeast Cell: A cell having two copies (alleles) of essentially every gene of its normal genomic complement, typically formed by the process of fusion (mating) of two haploid cells.

Tetraploid Yeast Cell: A cell having four copies (alleles) of essentially every gene of its normal genomic complement, typically formed by the process of fusion (mating) of two diploid cells. Tetraploids may carry two, three, four, or more different expression cassettes. Such tetraploids might be obtained in *S. cerevisiae* by selective mating homozygotic heterothallic a/a and alpha/alpha diploids and in *Pichia* by sequential mating of haploids to obtain auxotrophic diploids. For example, a [met his] haploid can be mated with [ade his] haploid to obtain diploid [his]; and a [met arg] haploid can be mated with [ade arg] haploid to obtain diploid [arg]; then the diploid [his] can be mated with the diploid [arg] to obtain a tetraploid prototroph. It will be understood by those of skill in the art that reference to the benefits and uses of diploid cells may also apply to tetraploid cells.

Yeast Mating: The process by which two yeast cells fuse to form a single yeast cell. The fused cells may be haploid cells or cells of higher ploidy (e.g., mating two diploid cells to produce a tetraploid cell).

Meiosis: The process by which a diploid yeast cell undergoes reductive division to form four haploid spore products. Each spore may then germinate and form a haploid vegetatively growing cell line.

Selectable Marker: A selectable marker is a gene or gene fragment that confers a growth phenotype (physical growth characteristic) on a cell receiving that gene as, for example through a transformation event. The selectable marker allows that cell to survive and grow in a selective growth medium under conditions in which cells that do not receive that selectable marker gene cannot grow. Selectable marker genes generally fall into several types, including positive selectable marker genes such as a gene that confers on a cell resistance to an antibiotic or other drug, temperature when two temperature sensitive ("ts") mutants are crossed or a is mutant is transformed; negative selectable marker genes such as a biosynthetic gene that confers on a cell the ability to grow in a medium without a specific nutrient needed by all cells that do not have that biosynthetic gene, or a mutagenized biosynthetic gene that confers on a cell inability to grow by cells that do not have the wild type gene; and the like. Suitable markers include but are not limited to: ZEO; NEO (G418); LYS3; MET1; MET3a; ADE1; ADE3; URA3; and the like.

Integrated: A genetic element (typically a heterologous genetic element) that are covalently joined into a chromosome of an organism.

Tandemly integrated: Two or more copies of a genetic element that are integrated in adjacent locations in a chromosome. The two or more copies do not necessarily have the same orientation; e.g., for transcribed genes, some copies may be transcribed from the Watson strand and others from the Crick strand.

Host cell: In the context of the present disclosure, the term host cell refers to a cell (e.g., a eukaryotic cell, such as a *Pichia* cell) which contains a heterologous gene. For example, the heterologous gene may provide for the expression of a subunit of a desired multi-subunit complex, a gene involved in protein folding (e.g., a chaperone), expression, or secretion, and/or another desired gene. The heterologous gene may be integrated into the genome of the eukaryotic cell or contained in extrachromosomal element such as a plasmid or artificial chromosome.

Expression Vector: These DNA vectors contain elements that facilitate manipulation for the expression of a foreign protein within the target host cell. Conveniently, manipulation of sequences and production of DNA for transformation is first performed in a bacterial host, e.g. *E. coli*, and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. Exemplary vectors and methods for transformation of yeast are described, for example, in Burke, D., Dawson, D., & Stearns, T. (2000). Methods in yeast genetics: a Cold Spring Harbor Laboratory course manual. Plainview, N.Y.: Cold Spring Harbor Laboratory Press, which is incorporated by reference herein in its entirety.

Expression vectors for use in the methods of the invention may further include yeast specific sequences, including a selectable auxotrophic or drug marker for identifying transformed yeast strains. A drug marker may further be used to select for amplification of copy number of the vector in a yeast host cell.

The polypeptide coding sequence of interest is typically operably linked to transcriptional and translational regulatory sequences that provide for expression of the polypeptide in yeast cells. These vector components may include, but are not limited to, one or more of the following: an enhancer element, a promoter, and a transcription termination sequence. Sequences for the secretion of the polypeptide may also be included, e.g. a signal sequence, and the like. A yeast origin of replication is optional, as expression vectors are often integrated into the yeast genome.

Though optional, in one embodiment of the invention, one or more subunit of the multi-subunit complex is operably linked, or fused, to a secretion sequence that provides for secretion of the expressed polypeptide into the culture media, which can facilitate harvesting and purification of the heterologous multi-subunit complex. Even more preferably, the secretion sequences provide for optimized secretion of the polypeptide from the host cells (e.g., yeast diploid cells), such as through selecting preferred codons and/or altering the percentage AT through codon selection. It is known in the art that secretion efficiency and/or stability can be affected by the choice of secretion sequence and the optimal secretion sequence can vary between different proteins (see, e.g., Koganesawa et al., Protein Eng. 2001 September; 14(9):705-10, which is incorporated by reference herein in its entirety). Many potentially suitable secretion signals are known in the art and can readily be tested for their effect upon yield and/or purity of a particular heterologous multi-subunit complex. Any secretion sequences may potentially be used, including those present in secreted proteins of yeasts and other species, as well as engineered secretion sequences. Exemplary secretion sequences that may be utilized include: chicken lysozyme (CLY) signal peptide (MRSLLILVLCFLPLAALG (SEQ ID NO:31)), CLY-L8 (MRLLLLLLLLPLAALG (SEQ ID NO:32)), S. cerevisiae invertase (SUC2) signal peptide (MLLQAFLFL-LAGFAAKISA (SEQ ID NO:33)), MF-alpha (Prepro) (MRFPSIFTAVLFAASSALA-APVNTTTE-EGVSLEKR (SEQ ID NO:34)), MF-alpha (Pre)-apv (MRFPSIFTAVL-FAASSALA-APV (SEQ ID NO:35)), MF-alpha (Pre)-apv-SLEKR (MRFPSIFTAVLFAASSALA-APVSLEKR (SEQ ID NO:36)), MF-alpha (Prepro)-(EA)3 (MRFPSIFTAVL-FAASSALA-APVNTTTE-EGVSLEKR-EAEAEA (SEQ ID NO:37)), αF signal peptide (MRFPSIFTAVLFAAS-SALA-APVNTTTE-DETAQIPAEAVIGYSDLEGDFDVA-VLPFSNSTNNGLLFINTTIASIAAKE-EGVSLEKR (SEQ ID NO:38)), KILM1 signal peptide (MTKPTQVLVRSVSILFFITLLHLVVALNDVAG-PAETAPVSLLPR (SEQ ID NO:39)), repressible acid phosphatase (PHO1) signal peptide (MFSPILSLEIILA-LATLQSVFA (SEQ ID NO:40)), A. niger GOX signal peptide (MQTLLVSSLVVSLAAALPHYIR (SEQ ID NO:41)), Schwanniomyces occidentalis glucoamylase gene (GAM1) signal peptide (MIFLKLIKSIVIGLGLVSAIQA (SEQ ID NO:42)), human serum albumin (HSA) signal peptide with pro-sequence (MKWVTFISLLFLFSSAY-SRGVFRR (SEQ ID NO:43)), human serum albumin (HSA) signal peptide without pro-sequence (MKWVTFISLLFLF-SSAYS (SEQ ID NO:44)), ISN signal peptide (MALWMRLLPLLALLALWGPDPAAA (SEQ ID NO:45)), IFN signal peptide (MKYTSYILAFQL-CIVLGSLGCDLP (SEQ ID NO:46)), HGH signal peptide (MAADSQTPWLLTFSLLCLLWPQEPGA (SEQ ID NO:47)), phytohaemagglutinin (PHA) (MKKNRMMM-MIWSVGVVWMLLLVGGSYG (SEQ ID NO:48)), Silkworm lysozyme (MQKLIIFALVVLCVGSEA (SEQ ID NO:49)), Human lysozyme (LYZ1) (MKAL-IVLGLVLLSVTVQG (SEQ ID NO:50)), activin receptor type-1 (MVDGVMILPVLIMIALPSPS (SEQ ID NO:51)), activin type II receptor (MGAAAKLAFAVFLISCSSG (SEQ ID NO:52)), P. pastoris immunoglobulin binding protein (PpBiP) (MLSLKPSWLTLAALMYAMLLVVVP-FAKPVRA (SEQ ID NO:53)), and human antibody 3D6 light chain leader (MDMRVPAQLLGLLLLWLPGAKC (SEQ ID NO:54)). See Hashimoto et al., Protein Engineering vol. 11 no. 2 pp. 75-77, 1998; Oka et al., Biosci Biotechnol Biochem. 1999 November; 63(11):1977-83; Gellissen et al., FEMS Yeast Research 5 (2005) 1079-1096; Ma et al., Hepatology. 2005 December; 42(6):1355-63; Raemaekers et al., Eur J Biochem. 1999 Oct. 1; 265(1):394-403; Koganesawa et al., Protein Eng. (2001) 14 (9): 705-710; Daly et al., Protein Expr Purif. 2006 April; 46(2):456-67; Damasceno et al., Appl Microbiol Biotechnol (2007) 74:381-389; and Felgenhauer et al., Nucleic Acids Res. 1990 Aug. 25; 18(16):4927, each of which is incorporated by reference herein in its entirety). The multi-subunit complex may also be secreted into the culture media without being operably linked or fused to a secretion signal. For example, it has been demonstrated that some heterologous polypeptides are secreted into the culture media when expressed in P. pastoris even without being linked or fused to a secretion signal. Additionally, the multi-subunit complex may be purified from host cells (which, for example, may be preferable if the complex is poorly secreted) using methods known in the art.

Media or cells comprising a desired multi-subunit complex may be recovered from the culture. Optionally, the secreted proteins may be purified. For example, cells comprising a desired multi-subunit complex may be lysed using mechanical, chemical, enzymatic, and/or osmotic methods (e.g., freezing with liquid nitrogen, using a homogenizer, spheroplasting, sonication, agitation in the presence of glass beads, using detergents, etc.). The desired multi-subunit complex may be concentrated, filtered, dialyzed, etc., using methods known in the art. The desired multi-subunit complex may be purified based on, for example, its molecular mass (e.g., size exclusion chromatography), isoelectric point (e.g., isoelectric focusing), electrophoretic mobility (e.g., gel electrophoresis), hydrophobic interaction chromatography (e.g., HPLC), charge (e.g., ion exchange chromatography), affinity (e.g., in the case of an antibody, binding to protein A, protein G, and/or an epitope to which the desired antibody binds), and/or glycosylation state (e.g., detected by lectin binding affinity). Multiple purification steps may be performed to obtain the desired level of purity. In an exemplary embodiment, the desired multi-subunit complex may be comprise an immunoglobulin constant domain and may be purified using protein A or protein G affinity, size exclusion chromatography, and lack of binding to lectin (to remove glycosylated forms). Optionally the A protease inhibitor, such as phenyl methyl sulfonyl fluoride (PMSF) may be added to inhibit proteolytic degradation during purification.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous Linking may be accomplished by ligation at convenient restriction sites or alternatively via a PCR/recombination method familiar to those skilled in the art (Gateway® Technology; Invitrogen, Carlsbad Calif.). If such sites do not exist, the synthetic oligonucleotide adapters or linkers may be used in accordance with conventional practice. Desired nucleic acids (including nucleic acids comprising operably linked sequences) may also be produced by chemical synthesis.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (that increase levels of transcription in response to absence of a repressor). Inducible promoters may initiate increased levels of transcription from DNA under their control in response to some change in culture conditions, e.g., the presence or absence of a nutrient or a change in temperature.

The yeast promoter fragment may also serve as the site for homologous recombination and integration of the expression vector into the same site in the yeast genome; alternatively a selectable marker is used as the site for homologous recombination. Pichia transformation is described in Cregg et al. (1985) Mol. Cell. Biol. 5:3376-3385, which is incorporated by reference herein in its entirety.

Examples of suitable promoters from Pichia include the CUP1 (induced by the level of copper in the medium), tetracycline inducible promoters, thiamine inducible promoters, AOX1 promoter (Cregg et al. (1989) Mol. Cell. Biol. 9:1316-1323); ICL1 promoter (Menendez et al. (2003) Yeast 20(13):1097-108); glyceraldehyde-3-phosphate dehydrogenase promoter (GAP) (Waterham et al. (1997) Gene 186(1): 37-44); and FLD1 promoter (Shen et al. (1998) Gene 216(1):93-102). The GAP promoter is a strong constitutive promoter and the CUP1, AOX and FLD1 promoters are inducible. Each foregoing reference is incorporated by reference herein in its entirety.

Other yeast promoters include ADH1, alcohol dehydrogenase II, GAL4, PHO3, PHO5, Pyk, and chimeric promoters derived therefrom. Additionally, non-yeast promoters may be used in the invention such as mammalian, insect, plant, reptile, amphibian, viral, and avian promoters. Most typically the promoter will comprise a mammalian promoter (potentially endogenous to the expressed genes) or will comprise a yeast or viral promoter that provides for efficient transcription in yeast systems.

The polypeptides of interest may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and processed through one of the standard pathways available within the host cell. The S. cerevisiae alpha factor pre-pro signal has proven effective in the secretion of a variety of recombinant proteins from P. pastoris. Other yeast signal sequences include the alpha mating factor signal sequence, the invertase signal sequence, and signal sequences derived from other secreted yeast polypeptides. Additionally, these signal peptide sequences may be engineered to provide for enhanced secretion in diploid yeast expression systems. Other secretion signals of interest also include mammalian signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g., K28 pre-protoxin sequence, PHA-E, FACE, human MCP-1, human serum albumin signal sequences, human Ig heavy chain, human Ig light chain, and the like. For example, see Hashimoto et. al. Protein Eng 11(2) 75 (1998); and Kobayashi et. al. Therapeutic Apheresis 2(4) 257 (1998), each of which is incorporated by reference herein in its entirety.

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing one or more of the above-listed components employs standard ligation techniques or PCR/recombination methods. Isolated plasmids or DNA fragments are cleaved, tailored, and re-ligated in the form desired to generate the plasmids required or via recombination methods. For analysis to confirm correct sequences in plasmids constructed, the ligation mixtures are used to transform host cells, and successful transformants selected by antibiotic resistance (e.g. ampicillin or Zeocin) where appropriate. Plasmids from the transformants are prepared, analyzed by restriction endonuclease digestion and/or sequenced.

As an alternative to restriction and ligation of fragments, recombination methods based on att sites and recombination enzymes may be used to insert DNA sequences into a vector. Such methods are described, for example, by Landy (1989) Ann. Rev. Biochem. 58:913-949; and are known to those of skill in the art. Such methods utilize intermolecular DNA recombination that is mediated by a mixture of lambda and E. coli-encoded recombination proteins. Recombination occurs between specific attachment (att) sites on the interacting DNA molecules. For a description of att sites see Weisberg and Landy (1983) Site-Specific Recombination in Phage Lambda, in Lambda II, Weisberg, ed. (Cold Spring Harbor, N.Y.: Cold Spring Harbor Press), pp. 211-250. The DNA segments flanking the recombination sites are switched, such that after recombination, the att sites are hybrid sequences comprised of sequences donated by each parental vector. The recombination can occur between DNAs of any topology. Each foregoing reference is incorporated by reference herein in its entirety.

Att sites may be introduced into a sequence of interest by ligating the sequence of interest into an appropriate vector; generating a PCR product containing att B sites through the use of specific primers; generating a cDNA library cloned into an appropriate vector containing att sites; and the like.

Monocistronic and polycistronic genes. A monocistronic gene encodes an RNA that contains the genetic information to translate only a single protein. A polycistronic gene encodes an mRNA that contains the genetic information to translate more than one protein. The proteins encoded in a polycistronic gene may have the same or different sequences or a combination thereof. Dicistronic or bicistronic refers to a polycistronic gene that encodes two proteins. Polycistronic genes optionally include one or more internal ribosome entry site (IRES) elements to facilitate cap-independent initiation of translation, which may be situated at a location that can drive translation of the downstream protein coding region independently of the 5'-cap structure bound to the 5' end of the mRNA molecule. Any known IRES sequence (e.g., viral, eukaryotic, or artificial in origin) may be used. For example, the cricket paralysis virus IRES sequence in the intergenic region (IGR) may be used, as described in Thompson et al. (2001) PNAS 98:12972-12977. Optionally, IRES function may be potentiated by genetic alteration, e.g., by causing constitutive expression of eIF2 kinase GCN2 or disrupting two initiator tRNA(met) genes disrupted (id.).

Folding, as used herein, refers to the three-dimensional structure of polypeptides and proteins, where interactions between amino acid residues act to stabilize the structure. While non-covalent interactions are important in determining structure, usually the proteins of interest will have intra- and/or intermolecular covalent disulfide bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The expression host may be further modified by the introduction of sequences encoding one or more enzymes that enhance folding and disulfide bond formation, i.e. foldases, chaperoning, etc. Such sequences may be constitutively or inducibly expressed in the yeast host cell, using vectors, markers, etc. as known in the art. Preferably the sequences, including transcriptional regulatory elements sufficient for the desired pattern of expression, are stably integrated in the yeast genome through a targeted methodology.

For example, the eukaryotic PDI is not only an efficient catalyst of protein cysteine oxidation and disulfide bond isomerization, but also exhibits chaperone activity. Co-expression of PDI can facilitate the production of active proteins having multiple disulfide bonds. Also of interest is the expression of BIP (immunoglobulin heavy chain binding protein); cyclophilin; and the like. In one embodiment of the invention, the multi-subunit complex may be expressed from a yeast strain produced by mating, wherein each of the haploid parental strains expresses a distinct folding enzyme, e.g. one strain may express BIP, and the other strain may express PDI or combinations thereof.

The terms "desired protein" or "target protein" are used interchangeably and refer generally to a heterologous multi-subunit protein such as a humanized antibody or a binding portion thereof described herein.

The term "antibody" includes any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." A preferred source for producing antibodies useful as starting material according to the invention is rabbits. Numerous antibody coding sequences have been described; and others may be raised by methods well-known in the art. Examples thereof include chimeric antibodies, human antibodies and other non-human mammalian antibodies, humanized antibodies, single chain antibodies such as scFvs, camelbodies, nanobodies, IgNAR (single-chain antibodies derived from sharks), small-modular immuno-pharmaceuticals (SMIPs), and antibody fragments such as Fabs, Fab', F(ab')$_2$ and the like. See Streltsov V A, et al., Structure of a shark IgNAR antibody variable domain and modeling of an early-developmental isotype, Protein Sci. 2005 November; 14(11):2901-9. Epub 2005 Sep. 30; Greenberg A S, et al., A new antigen receptor gene family that undergoes rearrangement and extensive somatic diversification in sharks, Nature. 1995 Mar. 9; 374(6518):168-73; Nuttall S D, et al., Isolation of the new antigen receptor from wobbegong sharks, and use as a scaffold for the display of protein loop libraries, Mol Immunol. 2001 August; 38(4):313-26; Hamers-Casterman C, et al., Naturally occurring antibodies devoid of light chains, Nature. 1993 Jun. 3; 363(6428):446-8; Gill D S, et al., Biopharmaceutical drug discovery using novel protein scaffolds, Curr Opin Biotechnol. 2006 December; 17(6):653-8. Epub 2006 Oct. 19. Each foregoing reference is incorporated by reference herein in its entirety.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the variable light and heavy chain regions ($V_L$ and $V_H$), obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety). It is further contemplated that the human constant regions of chimeric antibodies of the invention may be selected from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant regions.

Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference. Methods of humanizing antibodies have been described previously in issued U.S. Pat. No. 7,935,340, the disclosure of which is incorporated herein by reference in its entirety. In some instances, a determination of whether additional rabbit framework residues are required to maintain activity is necessary. In some instances the humanized antibodies still requires some critical rabbit framework residues to be retained to minimize loss of affinity or activity. In these cases, it is necessary to change single or multiple framework amino acids from human germline sequences back to the original rabbit amino acids in order to have desired activity. These changes are determined experimentally to identify which rabbit residues are necessary to preserve affinity and activity.

In addition to entire immunoglobulins (or their recombinant counterparts), immunoglobulin fragments comprising the epitope binding site (e.g., Fab', F(ab')$_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. In another embodiment of the invention, SMIPs (small molecule immunopharmaceuticals), camelbodies, nanobodies, and IgNAR are encompassed by immunoglobulin fragments.

Immunoglobulins and fragments thereof may be modified post-translationally, e.g. to add effector moieties such as chemical linkers, detectable moieties, such as fluorescent dyes, enzymes, toxins, substrates, bioluminescent materials, radioactive materials, chemiluminescent moieties and the like, or specific binding moieties, such as streptavidin, avidin, or biotin, and the like may be utilized in the methods and compositions of the present invention. Examples of additional effector molecules are provided infra.

Product-associated variant: a product other than the desired product (e.g., the desired multi-subunit complex) which is present in a preparation of the desired product and related to the desired product. Exemplary product-associated variants include truncated or elongated peptides, products having different glycosylation than the desired glycosylation (e.g., if an aglycosylated product is desired then any glycosylated product would be considered to be a product-associated variant), complexes having abnormal stoichiometry, improper assembly, abnormal disulfide linkages, abnormal or incomplete folding, aggregation, protease cleavage, or other abnormalities. Exemplary product-associated variants may exhibit alterations in one or more of molecular mass (e.g., detected by size exclusion chromatography), isoelectric point (e.g., detected by isoelectric focusing), electrophoretic mobility (e.g., detected by gel electrophoresis), phosphorylation state (e.g., detected by mass spectrometry), charge to mass ratio (e.g., detected by mass spectrometry), mass or identity of proteolytic fragments (e.g., detected by mass spectrometry or gel electrophoresis), hydrophobicity (e.g., detected by HPLC), charge (e.g., detected by ion exchange chromatography), affinity (e.g., in the case of an antibody, detected by binding to protein A, protein G, and/or an epitope to which the desired antibody binds), and glycosylation state (e.g., detected by lectin binding affinity). Where the desired protein is an antibody, the term product-associate variant may include a glyco-heavy variant and/or half antibody species (described below).

Exemplary product-associated variants include variant forms that contain aberrant disulfide bonds. For example, most IgG1 antibody molecules are stabilized by a total of 16 intra-chain and inter-chain disulfide bridges, which stabilize the folding of the IgG domains in both heavy and light chains, while the inter-chain disulfide bridges stabilize the association between heavy and light chains. Other antibody types likewise contain characteristic stabilizing intra-chain and inter-chain disulfide bonds. Further, some antibodies (including Ab-A and Ab-B disclosed herein) contain additional disulfide bonds referred to as non-canonical disulfide bonds. Thus, aberrant inter-chain disulfide bonds may result in abnormal complex stoichiometry, due to the absence of a stabilizing covalent linkage, and/or disulfide linkages to additional subunits. Additionally, aberrant disulfide bonds (whether inter-chain or intra-chain) may decrease structural stability of the antibody, which may result in decreased activity, decreased stability, increased propensity to form aggregates, and/or increased immunogenicity. Product-associated variants containing aberrant disulfide bonds may be detected in a variety of ways, including non-reduced denaturing SDS-PAGE, capillary electrophoresis, cIEX, mass spectrometry (optionally with chemical modification to produce a mass shift in free cysteines), size exclusion chromatography, HPLC, changes in light scattering, and any other suitable methods known in the art. See, e.g., The Protein Protocols Handbook 2002, Part V, 581-583, DOI: 10.1385/1-59259-169-8:581.

Half antibody, half-antibody species, or H1L1 refer to a protein complex that includes a single heavy and single light antibody chain, but lacks a covalent linkage to a second heavy and light antibody chain. Two half antibodies may remain non-covalently associated under some conditions (which may give behavior similar to a full antibody, e.g., apparent molecular weight determined by size exclusion chromatography). Similarly, H2L1 refers to a protein complex that includes two heavy antibody chains and single light antibody chain, but lacks a covalent linkage to a second light antibody chain; these complexes may also non-covalently associate with another light antibody chain (and likewise give similar behavior to a full antibody). Like full antibodies, half antibody species and H2L1 species can dissociate under reducing conditions into individual heavy and light chains. Half antibody species and H2L1 species can be detected on a non-reduced SDS-PAGE gel as a species migrating at a lower apparent molecular weight than the full antibody, e.g., H1L1 migrates at approximately half the apparent molecular weight of the full antibody (e.g., about 75 kDa).

Glyco-heavy variant refers to a glycosylated product-associated variant sometimes present in antibody preparations and which contains at least a partial Fc sequence. The glyco-heavy variant is characterized by decreased electrophoretic mobility observable by SDS-PAGE (relative to a normal heavy chain), lectin binding affinity, binding to an anti-Fc antibody, and apparent higher molecular weight of antibody complexes containing the glyco-heavy variant as determined by size exclusion chromatography. See U.S. Provisional Application Ser. No. 61/525,307, filed Aug. 31, 2011 which is incorporated by reference herein in its entirety.

The term "polyploid yeast that stably expresses or expresses a desired secreted heterologous polypeptide for prolonged time" refers to a yeast culture that secretes said polypeptide for at least several days to a week, more preferably at least a month, still more preferably at least 1-6 months, and even more preferably for more than a year at threshold expression levels, typically at least 50-500 mg/liter (after about 90 hours in culture) and preferably substantially greater.

The term "polyploidal yeast culture that secretes desired amounts of recombinant polypeptide" refers to cultures that stably or for prolonged periods secrete at least at least 50-500 mg/liter, and most preferably 500-1000 mg/liter or more.

A polynucleotide sequence "corresponds" to a polypeptide sequence if translation of the polynucleotide sequence in accordance with the genetic code yields the polypeptide sequence (i.e., the polynucleotide sequence "encodes" the polypeptide sequence), one polynucleotide sequence "corresponds" to another polynucleotide sequence if the two sequences encode the same polypeptide sequence.

A "heterologous" region or domain of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A "coding sequence" is an in-frame sequence of codons that (in view of the genetic code) correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide. A polyadenylation signal and transcription termination sequence will usually be located 3' to the coding sequence. A "promoter sequence" is a DNA regulatory region capable of binding RNA polymerase in a cell and initiating transcription of a downstream (3' direction) coding sequence. Promoter sequences typically contain additional sites for binding of regulatory molecules (e.g., transcription factors) which affect the transcription of the coding sequence. A coding sequence is "under the control" of the promoter sequence or "operatively linked" to the promoter when RNA polymerase binds the promoter sequence in a cell and transcribes the coding sequence into mRNA, which is then in turn translated into the protein encoded by the coding sequence.

Vectors are used to introduce a foreign substance, such as DNA, RNA or protein, into an organism or host cell. Typical vectors include recombinant viruses (for polynucleotides) and liposomes (for polypeptides). A "DNA vector" is a replicon, such as plasmid, phage or cosmid, to which another polynucleotide segment may be attached so as to bring about the replication of the attached segment. An "expression vector" is a DNA vector which contains regulatory sequences which will direct polypeptide synthesis by an appropriate host cell. This usually means a promoter to bind RNA polymerase and initiate transcription of mRNA, as well as ribosome binding sites and initiation signals to direct translation of the mRNA into a polypeptide(s). Incorporation of a polynucleotide sequence into an expression vector at the proper site and in correct reading frame, followed by transformation of an appropriate host cell by the vector, enables the production of a polypeptide encoded by said polynucleotide sequence.

"Amplification" of polynucleotide sequences is the in vitro production of multiple copies of a particular nucleic acid sequence. The amplified sequence is usually in the form of DNA. A variety of techniques for carrying out such amplification are described in the following review articles, each of which is incorporated by reference herein in its entirety: Van Brunt 1990, Bio/Technol., 8(4):291-294; and Gill and Ghaemi, Nucleosides Nucleotides Nucleic Acids. 2008 March; 27(3):224-43. Polymerase chain reaction or PCR is a prototype of nucleic acid amplification, and use of PCR herein should be considered exemplary of other suitable amplification techniques.

The general structure of antibodies in most vertebrates (including mammals) is now well understood (Edelman, G. M., Ann. N.Y. Acad. Sci., 190: 5 (1971)). Conventional antibodies consist of two identical light polypeptide chains of molecular weight approximately 23,000 daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the $F_C$ region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (IgG, IgM, IgA, IgD, and IgE corresponding to gamma, mu, alpha, delta, and epsilon heavy chain constant regions). The constant region or class determines subsequent effector function of the antibody, including activation of complement (Kabat, E. A., Structural Concepts in Immunology and Immunochemistry, 2nd Ed., p. 413-436, Holt, Rinehart, Winston (1976)), and other cellular responses (Andrews, D. W., et al., Clinical Immunobiology, pp 1-18, W. B. Sanders (1980); Kohl, S., et al., Immunology, 48: 187 (1983)); while the variable region determines the antigen with which it will react. Light chains are classified as either kappa or lambda. Each heavy chain class can be paired with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

The expression "variable region" or "VR" refers to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The expressions "complementarity determining region," "hypervariable region," or "CDR" refer to one or more of the hyper-variable or complementarity determining regions (CDRs) found in the variable regions of light or heavy chains of an antibody (See Kabat, E. A. et al., Sequences of Proteins of Immunological Interest, National Institutes of Health, Bethesda, Md., (1987)). These expressions include the hypervariable regions as defined by Kabat et al. ("Sequences of Proteins of Immunological Interest," Kabat E., et al., US Dept. of Health and Human Services, 1983) or the hypervariable loops in 3-dimensional structures of antibodies (Chothia and Lesk, J Mol. Biol. 196 901-917 (1987)). The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction (Kashmiri, S., Methods, 36:25-34 (2005)).

The expressions "framework region" or "FR" refer to one or more of the framework regions within the variable regions of the light and heavy chains of an antibody (See Kabat, E. A. et al., Sequences of Proteins of Immunological Interest, National Institutes of Health, Bethesda, Md., (1987)). These expressions include those amino acid sequence regions interposed between the CDRs within the variable regions of the light and heavy chains of an antibody.

The expression "stable copy number" refers to a host cell that substantially maintains the number of copies of a gene (such as an antibody chain gene) over a prolonged period of time (such as at least a day, at least a week, or at least a month, or more) or over a prolonged number of generations of propagation (e.g., at least 30, 40, 50, 75, 100, 200, 500, or 1000 generations, or more). For example, at a given time point or number of generations, at least 50%, and preferably at least 70%, 75%, 85%, 90%, 95%, or more of cells in the culture may maintain the same number of copies of the gene as in the starting cell. In a preferred embodiment, the host cell contains a stable copy number of each subunit of the desired multi-subunit complex (e.g., antibody).

The expression "stably expresses" refers to a host cell that maintains similar levels of expression of a gene or protein (such as an antibody) over a prolonged period of time (such as at least a day, at least a week, or at least a month, or more) or over a prolonged number of generations of propagation (e.g., at least 30, 40, 50, 75, 100, 200, 500, or 1000 generations, or more). For example, at a given time point or number of generations, the rate of production or yield of the gene or protein may be at least 50%, and preferably at least 70%, 75%, 85%, 90%, 95%, or more of the initial rate of production. In a preferred embodiment, the host cell stably expresses the desired multi-subunit complex (e.g., antibody).

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Increased Antibody Yield by Varying Heavy and Light Chain Gene Copy Number

This example demonstrates that yield of recombinant antibodies produced in *P. pastoris* can be greatly increased by varying the number of copies of the heavy and light chain genes. In particular, this example demonstrates that the present methods permit targeted matings that yield such strains. A panel of diploid *P. pastoris* strains each expressing humanized antibodies from a differing number of copies of the heavy and light chain genes was generated and tested to identify combinations of gene copy numbers that produced a greater antibody yield. FIG. 1 provides an overview of the methods used to efficiently generate the panel of diploid strains (detailed methods are provided in Example 4 below). In brief, haploid strains were transformed with genes encoding either the heavy or light chain genes under the control of a promoter fused to a secretion signal. To direct integration into a specific genetic locus within the *P. pastoris* genome, the plasmid was linearized within the homologous sequence of the targeted locus. In this example, the constructs were integrated into the pGAP, 3'AOX TT and HIS4 TT loci, though other loci could also be used. Transformants containing multiple tandemly integrated copies of the antibody chain gene were identified by Southern blot, and haploid strains containing defined numbers of copies of the light or heavy chain genes were selected for further use. Optionally, additional copies of the same antibody chain gene were integrated into a second locus in the haploid strain. Mating of these haploid strains efficiently produced diploid strains containing defined numbers of light and heavy chain genes in varying combinations. After mating, gene copy numbers in the diploid strains were verified by Southern blotting.

Using these methods, diploid *P. pastoris* strains were produced containing heavy and light chain genes encoding three humanized antibodies, Ab-A and Ab-B, and Ab-C. The antibody polypeptide and polynucleotide sequences are shown in FIG. 38 (Ab-A), FIG. 39 (Ab-B, and FIG. 40 (Ab-C)). Ab-A, Ab-B and Ab-C are humanized antibodies that were derived from three different rabbit antibodies. Ab-C is specific for a different antigen than Ab-A and Ab-B.

The diploid strains are summarized in Tables 1, 2, and 3 below. The prefix of each strain identifier indicates the antibody produced, and the numbers following H and L refer to the number of integrated copies of the heavy and light chain genes, respectively. For example, the strain designator Ab-A-H3×L4 identifies a strain that expresses Ab-A and contains three copies of the heavy chain gene and four copies of the light chain gene. Columns labeled pGAP, 3'AOX TT and HIS4 TT indicate the number of gene copies integrated at each respective locus. Each locus is listed twice to reflect integration into homologous chromosomes (one originating from each parental haploid strain).

Selected diploid strains were cultured in a bioreactor under conditions that generated antibody production and secretion as described in Example 5. Each antibody chain was under control of the GAP promoter, whose expression was upregulated by switching from a glycerol carbon source to a glucose carbon source under conditions that converted some of the glucose to ethanol (low oxygen availability). An in-frame fusion of each antibody chain gene to a secretion sequence caused secretion of the expressed antibodies into the culture media. Culture media was harvested at approximately 90 hours of growth (T90) and antibody yield was determined by high performance liquid chromatography (HPLC) as described in Example 6.

Relative antibody yields from selected Ab-A-expressing strains at T90 are shown in the rightmost column of Table 1, below, and illustrated graphically in FIG. 2. The H3×L3 strain was used as a reference and its expression yield was set to 100%. Whole broth antibody titer generally increased with antibody copy number, in the order Ab-A-H3×L4, Ab-A-H3×L3, Ab-A-H4×L4, Ab-A-H4×L6, Ab-A-H5×L4, Ab-A-H5×L5, and Ab-A-H5×L7. Yield from all three Ab-A-H5 strains exceeded that from both Ab-A-H4 strains, which exceeded that from the two Ab-A-H3 strains. For a given heavy chain copy number, total yield also increased with increasing light chain copy number, with the exception that the yield from H3×L4 was about 13% lower than the yield from H3×L3.

Similar yield results were obtained from strains expressing Ab-B, which are shown in the rightmost column of Table 2, below, and illustrated graphically in FIG. 3. The H3×L3 strain was used as a reference and its expression yield was set to 100%. As with Ab-A, yield of Ab-B generally increased with antibody copy number, in the order Ab-B-H3×L3, Ab-B-H3×L4, Ab-B-H4×L3, Ab-B-H4×L5, and Ab-B-H4×L6. Yield from all three Ab-B-H4 strains exceeded that from both Ab-B-H3 strains.

Increasing antibody copy number likewise generally increased the yield of antibody Ab-C, as shown in the rightmost column of Table 3 below and illustrated graphically in FIG. 4. Antibody yields generally increased with antibody copy number in the order Ab-C-H3×L4, Ab-C-H4× L3, Ab-C-H4×L4, Ab-C-H4×L5, Ab-C-H5×L5, Ab-C-H5× L4, Ab-C-H5×L6, and Ab-C-H6×L5. Yield increases were relatively modest between strains having 5 heavy chain copies or more. Additionally, the Ab-C-H6×L6 strain exhibited a substantial decrease in yield relative to the Ab-C-H6× L5 and Ab-C-H5×L6 strains, such that the yield from this strain was comparable to the Ab-C-H4×L4 strain.

TABLE 1

Summary of diploid P. pastoris strains expressing Ab-A. Defined numbers of copies of genes encoding the heavy chain (Hc) and light chain (Lc) of Ab-A were integrated into the identified chromosomal loci. Column headings that identify same genomic locus refer to homologous chromosomes Selected strains were cultured and assayed to determine yield of antibody secreted into the culture media (rightmost column). These results are graphically illustrated in FIG. 2.

| Diploid Strain | Hc copies (pGAP locus) | Hc copies (HIS4 TT locus) | Lc copies (pGAP locus) | Lc copies (HIS4 TT locus) | Whole Broth Antibody Yield (% lowest copy number) |
|---|---|---|---|---|---|
| Ab-A-H2xL2 | 2 | 0 | 2 | 0 | NT |
| Ab-A-H2xL3 | 2 | 0 | 3 | 0 | NT |
| Ab-A-H3xL3 | 3 | 0 | 3 | 0 | 100% |
| Ab-A-H3xL4 | 3 | 0 | 4 | 0 | 87% |
| Ab-A-H3xL5 | 3 | 0 | 3 | 2 | NT |
| Ab-A-H4xL3 | 3 | 1 | 3 | 0 | NT |
| Ab-A-H4xL4 | 3 | 1 | 3 | 1 | 145% |
| Ab-A-H4xL5 | 3 | 1 | 3 | 2 | NT |
| Ab-A-H4xL6 | 3 | 1 | 3 | 3 | 180% |
| Ab-A-H5xL4 | 3 | 2 | 3 | 1 | 206% |
| Ab-A-H5xL5 | 3 | 2 | 3 | 2 | 211% |
| Ab-A-H5xL6 | 3 | 2 | 3 | 3 | NT |
| Ab-A-H5xL7 | 3 | 2 | 3 | 4 | 224% |

NT: Not tested in bioreactors

TABLE 2

Summary of diploid P. pastoris strains expressing Ab-B. Defined numbers of copies of genes encoding the heavy chain (Hc) and light chain (Lc) of Ab-B were integrated into the identified chromosomal loci. Column headings that identify same genomic locus refer to homologous chromosomes Selected strains were cultured and assayed to determine yield of antibody secreted into the culture media (rightmost column). These results are graphically illustrated in FIG. 3.

| Diploid Strain | Hc copies (pGAP) | Hc copies (HIS4 TT) | Lc copies (pGAP) | Lc copies (HIS4 TT) | Whole Broth Antibody Yield (% lowest copy number) |
|---|---|---|---|---|---|
| Ab-B-H2xL2 | 2 | 0 | 2 | 0 | NT |
| Ab-B-H2xL3 | 2 | 0 | 3 | 0 | NT |
| Ab-B-H2xL4 | 2 | 0 | 4 | 0 | NT |
| Ab-B-H3xL3 | 3 | 0 | 3 | 0 | 100% |
| Ab-B-H3xL4 | 3 | 0 | 4 | 0 | 104% |
| Ab-B-H3xL5 | 3 | 0 | 5 | 0 | NT |
| Ab-B-H4xL3 | 3 | 1 | 3 | 0 | 143% |
| Ab-B-H4xL4 | 3 | 1 | 3 | 1 | NT |
| Ab-B-H4xL5 | 3 | 1 | 3 | 2 | 178% |
| Ab-B-H4xL6 | 3 | 1 | 3 | 3 | 184% |
| Ab-B-H5xL4 | 3 | 2 | 3 | 1 | NT |
| Ab-B-H5xL5 | 3 | 2 | 3 | 2 | NT |
| Ab-B-H5xL6 | 3 | 2 | 3 | 3 | NT |
| Ab-B-H5xL7 | 3 | 2 | 3 | 4 | NT |

NT: Not tested

TABLE 3

Summary of diploid P. pastoris strains expressing Ab-C. Defined numbers of copies of genes encoding the heavy chain (Hc) and light chain (Lc) of Ab-C were integrated into the identified chromosomal loci. Column headings that identify same genomic locus refer to homologous chromosomes Selected strains were cultured and assayed to determine yield of antibody secreted into the culture media (rightmost column). These results are graphically illustrated in FIG. 4.

| Diploid Strain | Hc copies (3'AOX TT) | Hc copies (HIS4 TT) | Lc copies (3'AOX TT) | Lc copies (HIS4 TT) | Whole Broth Antibody Yield (% H3xL3) |
|---|---|---|---|---|---|
| Ab-C-H3xL4 | 3 | 0 | 4 | 0 | 120 |
| Ab-C-H4xL3 | 4 | 0 | 3 | 0 | 140 |
| Ab-C-H4xL4 | 4 | 0 | 4 | 0 | 168 |
| Ab-C-H4xL5 | 4 | 0 | 5 | 0 | 204 |
| Ab-C-H5xL4 | 3 | 2 | 4 | 0 | 240 |
| Ab-C-H5xL5 | 3 | 2 | 3 | 2 | 234 |
| Ab-C-H5xL6 | 3 | 2 | 4 | 2 | 245 |
| Ab-C-H6xL5 | 4 | 2 | 3 | 2 | 252 |
| Ab-C-H6xL6 | 4 | 2 | 4 | 2 | 163 |

These results demonstrated that yield of three different antibodies can be greatly increased by altering the number of copies of the heavy and light chain genes. Moreover, the results demonstrate that a panel of strains containing varying (defined) numbers of copies of heavy and light chain genes can be generated by mating haploid strains containing defined numbers of copies of the heavy chain genes with haploid strains containing defined numbers of copies of the light chain genes. Among the strains shown, yield could be more than doubled (e.g., compare FIG. 2, strains H3×L4 and H5×L7). Though strains containing lower numbers of gene copies were not included in this example, it is expected that the magnitude of improvement is even greater relative such strains. Moreover, further improvement might be attainable by further increasing the number of gene copies beyond those exemplified, though yield may decrease for copy numbers exceeding an optimum value.

Example 2

Increased Antibody Purity by Varying Heavy and Light Chain Gene Copy Number

This example demonstrates that the purity of recombinant antibodies generated in *P. pastoris* was greatly increased by varying the number of copies of the light and heavy chain genes. Strains containing varying (defined) numbers of copies of heavy and light chain genes were generated by mating haploid strains containing defined numbers of copies of the heavy chain genes with haploid strains containing defined numbers of copies of the light chain genes. Between the strains compared, overall production of undesired side-products was decreased by approximately 20%. Additionally, production of the single most abundant side-product was demonstrated to be decreased by up to about 82% between the strains compared.

Antibody purity was determined by protein-A purification of secreted antibody from the culture media, followed by HPLC using the methods described in Example 6. The samples were maintained in native conditions expected to preserve assembled antibody complexes, permitting detection of abnormalities affecting the assembled complexes (such as incorrect stoichiometry, improper assembly, aggregation, protease cleavage, and other aberrations). Overall purity was determined by measuring the proportion of total signal observed in the peak corresponding to the expected antibody (about 16.7 minutes retention time). Exemplary HPLC traces are shown for Ab-A preparations from strains Ab-A-H4×L4 (FIG. 5A and enlarged view in FIG. 5B) and Ab-A-H4×L6 (FIG. 5C and enlarged view in FIG. 5D). Total detected signal is quantified for four regions of each trace, corresponding to the elution prior to the major peaks (0 to 14.6 minutes retention time), the main product variant peak (15.5 minutes retention time), the expected antibody peak (16.7 minutes retention time), and elution after the expected antibody peak (18 to 22 minutes) (FIG. 5E). The purity of the antibody preparation from Ab-A-H4×L4 was about 83.7%, and the purity of the antibody preparation from strain Ab-A-H4×L6 was about 87.0%. By this measure, the overall level of impurities was reduced by about 20% (from 16.3% to 13%) by increasing the number of copies of the light chain gene. The abundance of the main product variant peak (15.5 minutes retention time) was dramatically decreased from 8.81% to 1.58% (82% decreased) by increasing the number of copies of the light chain gene.

Figure 6:
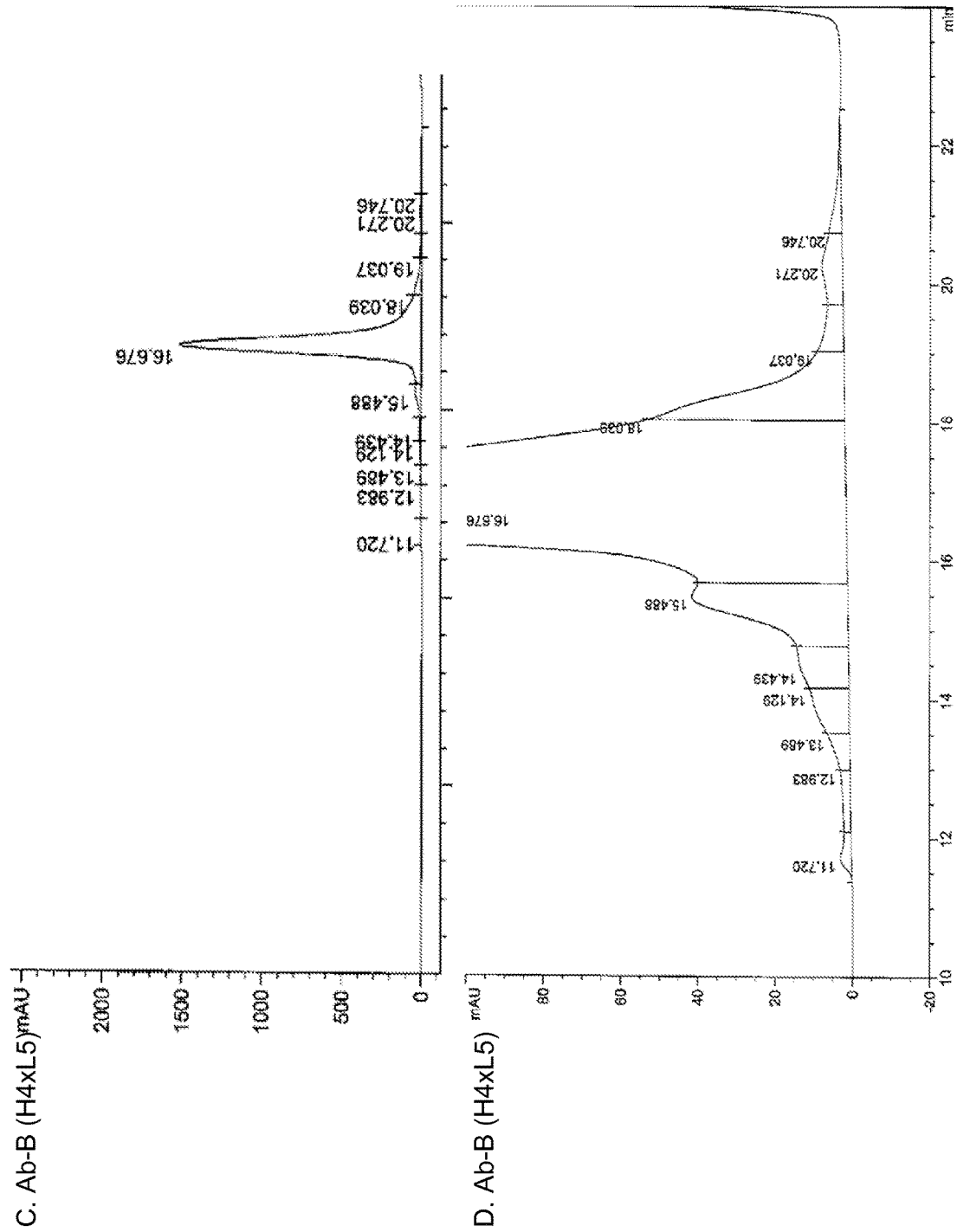
FIG. 6A-E shows the purity of protein-A capture eluate of Ab-B produced from H4×L3 and H4×L5 strains determined by HPLC. The level of the product-associated variant (measured by the percentage of total integrated area) migrating at 15.5 min, was decreased by about 59% (from 6.26% in H4×L3 down to 2.54% in H4×L5).

Similar results were obtained by HPLC analysis of Ab-B preparations. Exemplary HPLC traces are shown for the antibody preparation from strains Ab-B-H4×L3 (FIG. 6A and enlarged view in FIG. 6B) and Ab-B-H4×L5 (FIG. 6C and enlarged view in FIG. 6D). The purity of the antibody preparation from Ab-B-H4×L3 was about 90.05%, and the purity of the antibody preparation from strain Ab-B-H4×L5 was about 92.18%. By this measure, the level of impurities was reduced by about 21% (from about 10% to about 7.8%) by increasing the number of copies of the light chain gene. As with Ab-A, at the main product variant had a peak with a retention time of about 15.5 minutes. The abundance of this predominant variant was decreased by about 59% (from 6.26% to 2.54%) by increasing the number of copies of the light chain gene (FIG. 6E).

Figure 7:
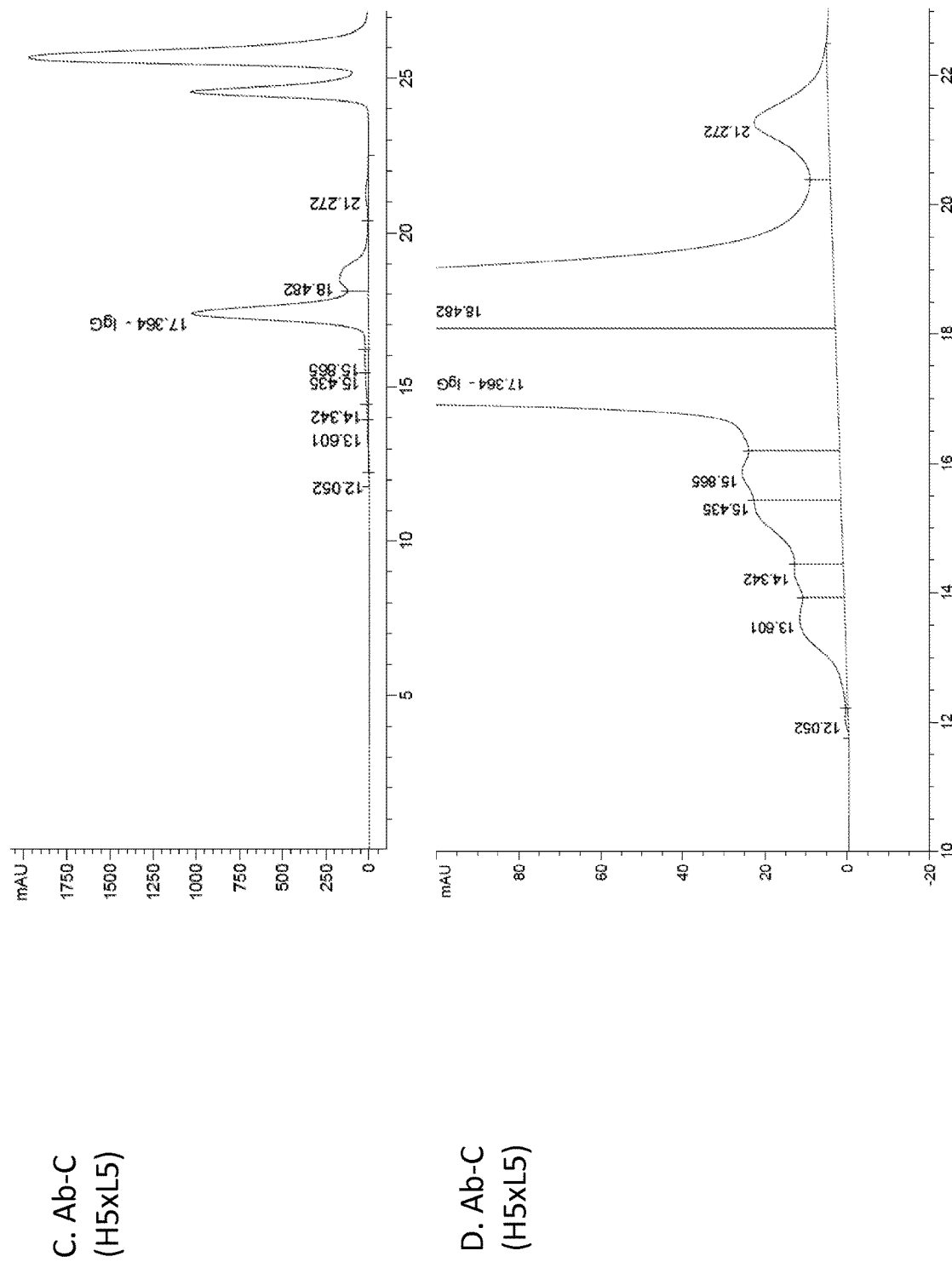
FIG. 7A-E shows the purity of protein-A capture eluate of Ab-C produced from Hex L3 and H5×L5 strains determined by HPLC. The level of the product-associated variant (measured by the percentage of total integrated area) migrating at 15.2 to 16.1 min, was decreased by about 39% (from 6.55% in H3×L3 down to 4.00% in H5×L5).

Purity of the Ab-C preparations were also analyzed by HPLC. Exemplary HPLC traces are shown for the antibody preparation from strains Ab-C-H3×L3 (FIG. 7A and enlarged view in FIG. 7B) and Ab-C-H5×L5 (FIG. 7C and enlarged view in FIG. 7D). The main product variant had a peak with a retention time of 15.2 to 16.1 minutes. The abundance of this predominant variant was decreased by about 39% (from 6.55% to 4.00%) by increasing the number of copies of the light and heavy chain genes (FIG. 7E).

Product variants in Ab-A (FIG. 8), Ab-B (FIG. 9), and Ab-C (FIG. 10) preparations were also visualized on protein gels. Because the samples were subjected to denaturing and reducing conditions, this method can detect abnormalities affecting the constitution of individual antibody chains but would not be expected to detect other types of abnormalities (such as complexes having improper stoichiometry, aggregation, protease cleavage, improper disulfide linkages, or other assembly errors). The antibodies were purified by Protein-A affinity chromatography as described in Example 7, then resolved by SDS-PAGE and stained with Coomassie Blue staining. As expected, the major bands corresponded to the predicted molecular weight of the heavy and light chains (confirmed in FIG. 8 by the lane labeled "Reference" which was loaded with a pure reference antibody). A single predominant product-associated variant was readily observable in each sample (FIGS. 8, 9, and 10, arrow labeled "Low-mobility product-associated variant"). The low-mobility product-associated variant had decreased electrophoretic mobility relative to the heavy chain. The amount of this product-associated variant was visibly reduced in the antibody preparation from the strains containing higher numbers of copies of the light chain, specifically in the Ab-A preparation from the Ab-A-H4×L6 strain compared to the Ab-A-H4×L4 strain (FIG. 8), in the Ab-B preparation from the Ab-B-H4×L6 strain compared to the Ab-B-H4×L5 strain (FIG. 9), and in the Ab-C preparation from the Ab-C-H5×L5 strain compared to the Ab-C-H3×L3 strain.

Thus, for three different antibodies, two complementary methods of detecting impurities (HPLC and SDS-PAGE) both demonstrated that increased copy number of the antibody light chain resulted in improved antibody purity. Further experiments (described in Example 3 below) demonstrated a glycosylated heavy chain variant ("glyco-heavy variant") was a constituent of the predominant product-associated variant detected by both methods.

Example 3

Decreased Production of Glycosylated Heavy Chain Variant by Varying Heavy and Light Chain Gene Copy Number This example characterizes the most abundant product-associated variant that was observed in preparations of recombinant antibodies in the preceding example. Specifically, the product-associated variant was shown to be a glycosylated polypeptide containing at least part of human Fc ("glyco-heavy variant"). Production of the glyco-heavy variant was shown to be decreased in strains having an increased number of copies of the light chain gene. Because glycoproteins are potentially more immunogenic than aglycosylated forms, manipulation of the host cell to decrease their production may be particularly beneficial for some intended uses.

The low-mobility product-associated variant described in the preceding example was demonstrated to be a glycoprotein by its specific binding to a lectin-containing resin. Glycoproteins were purified from two Ab-B preparations (from H4×L5 and H4×L3 strains) and analyzed by SDS-PAGE and Western blotting using the methods described in Example 8. FIG. 11A shows analysis of the loaded material (left panel, "Load") and lectin column eluate (right panel, "Lectin Eluate) by SDS-PAGE with Coomassie Blue staining. Three predominant bands were detected in the lectin column eluate: the low-mobility product-associated variant (arrows), and the light and heavy chain polypeptides. Compared to the loaded material (FIG. 11A, left panel), the low-mobility product-associated variant (arrow) was greatly enriched in the lectin column eluate (FIG. 11A, right panel). These results indicated that the low-mobility product-associated variant was a glycoprotein. Additionally, the co-purification of light- and heavy-chain polypeptides strongly suggests that the low-mobility product-associated variant was physically associated with these polypeptides. FIG. 11B shows further characterization of the loaded material (left panel, "Load") and lectin column eluate (right panel, "Lectin Eluate") by Western blotting with an anti-HuFc antibody conjugated to horseradish peroxidase (GoatAntiHuFC-HRP at 1:10,000). This antibody specifically bound the Fc sequence contained in the human heavy chain polypeptide as expected (FIG. 11B, lower band). The low-mobility product-associated variant was specifically detected (FIG. 11B, arrow), indicating that it contained at least part of Fc sequence of the heavy chain. Moreover, Western signal from the low-mobility product-associated variant was greatly enriched in the lectin column eluate, confirming that the lectin-enriched band and Fc-containing band were the same. Therefore, we concluded that the low-mobility product-associated variant was a glycoprotein containing at least the Fc portion of the heavy chain, possibly associated with a complex containing light- and heavy-chains, which is referred to herein as the "glyco-heavy variant."

Relative abundance of the glyco-heavy variant was also shown to be decreased in the preparation from strain Ab-B-H4×L5 relative to Ab-B-H4×L3. Protein-A purified antibody prepared from each strain was compared on a Coomassie stained gel (FIG. 11A, left panel) and the abundance of the glyco-heavy variant was visibly decreased in the H4×L5 preparation. Consistent with these results, the abundance of the glyco-heavy variant in the H4×L5 preparation was also visibly decreased relative to the (H4×L3 preparation) in the lectin column eluate (FIG. 11A, right panel). The same results were observed when the glyco-heavy variant was detected with an anti-HuFc antibody (FIG. 11B). These results indicate that the production of the glyco-heavy variant can be modulated by varying the number of copies of antibody chain genes.

Lectin-purified Ab-B preparations were then analyzed by HPLC using the methods described in Example 8 below. Prior to lectin purification, the main peak corresponded to the expected antibody (about 16.7 minutes retention time) for the preparations from both H4×L3 (FIG. 12A and enlarged view in FIG. 12B) and H4×L5 (FIG. 13A and enlarged view in FIG. 13B) strains. In both preparations, the most abundant product-associated variant observed had a retention time of about 15.5 minutes. After lectin purification, that product-associated variant was greatly enriched and became predominant in the preparations from both H4×L3 (FIG. 12C and enlarged view in FIG. 12D) and H4×L5 (FIG. 13C and enlarged view in FIG. 13D) strains. Because it was greatly enriched in the lectin column eluate, we concluded that the glyco-heavy form observed using reduced protein gels was a constituent of the product-associated variant having a retention time of 15.5 minutes.

Figure 12:
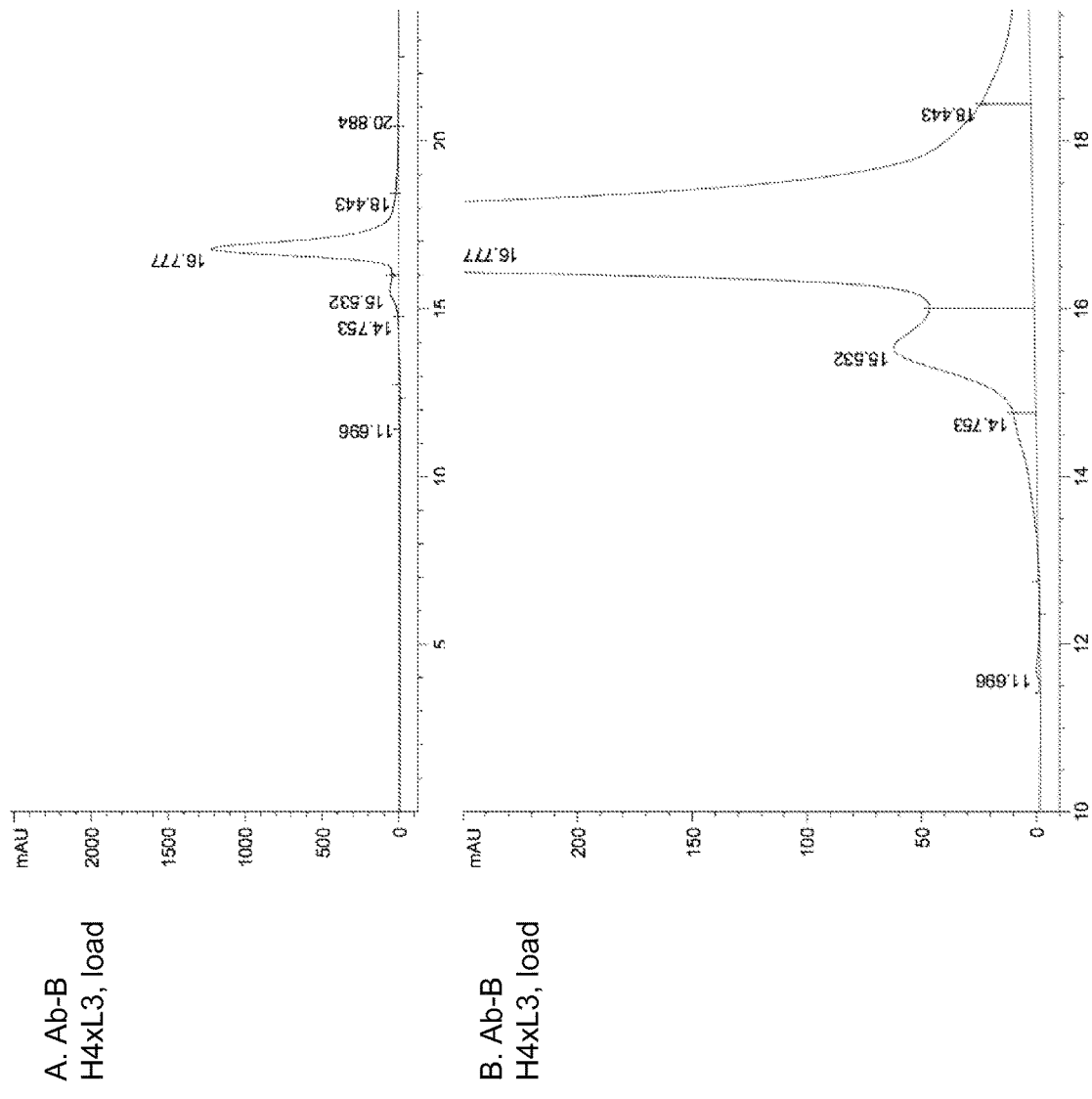
FIGS. 12A-D and 13A-D demonstrate that a product-associated variant observed by HPLC (having a retention time of approximately 15.5 minutes) was selectively enriched in the lectin column eluate, indicating that the glyco-heavy variant was a constituent of this product-associated variant. Antibody Ab-B was prepared from H4×L3 and H4×L5 strains.
Figure 12:
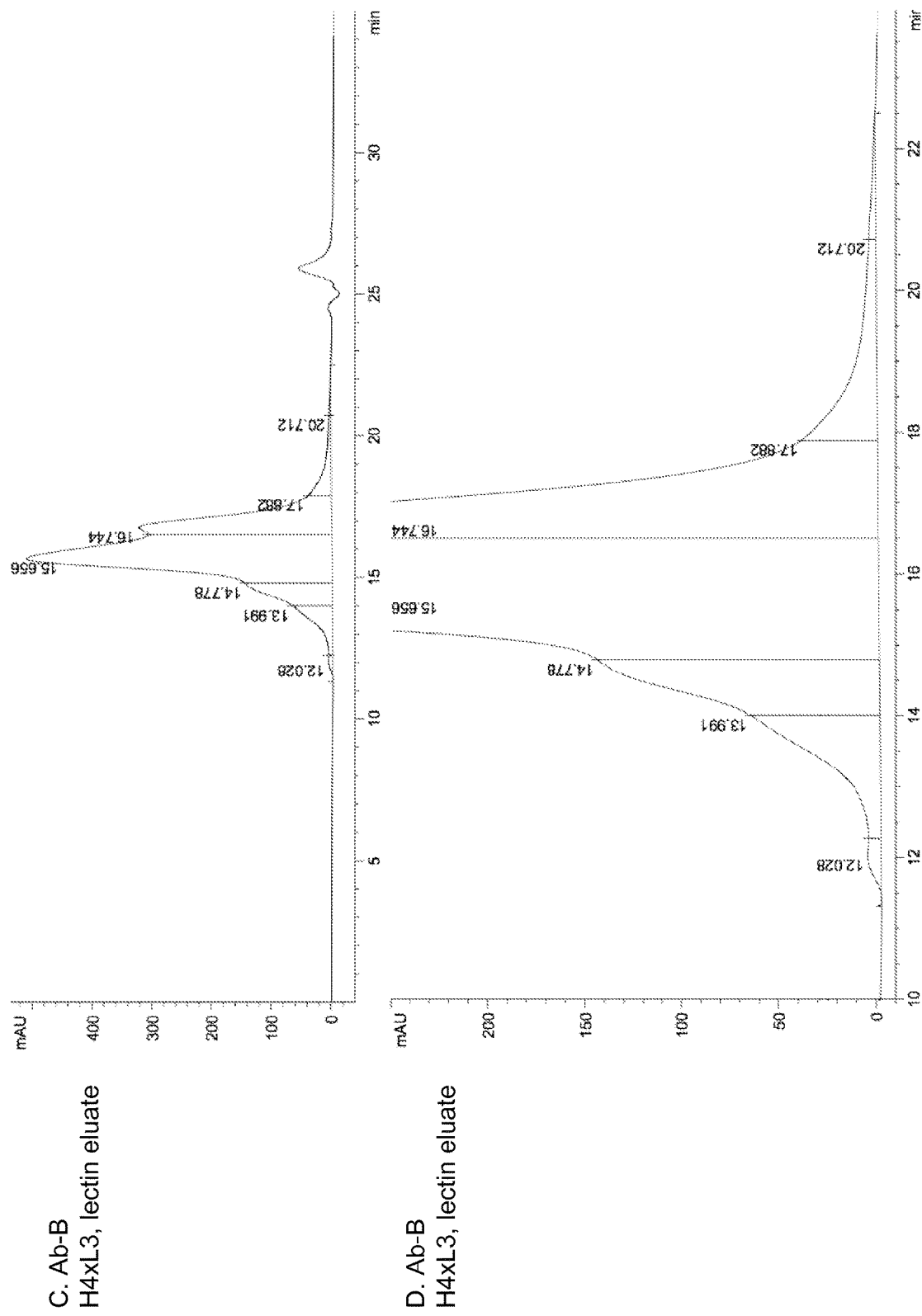
Figure 13:
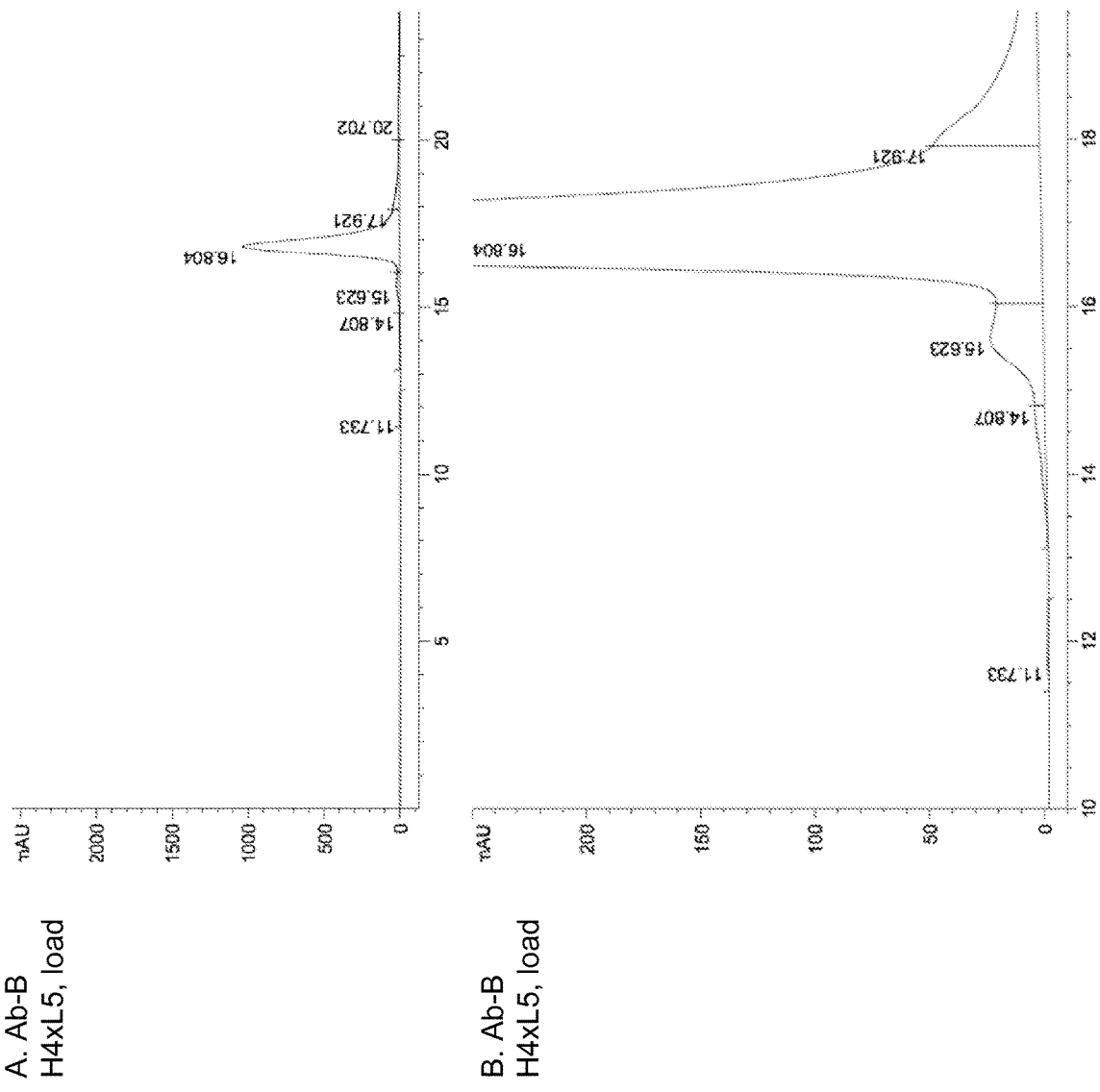
Figure 13:
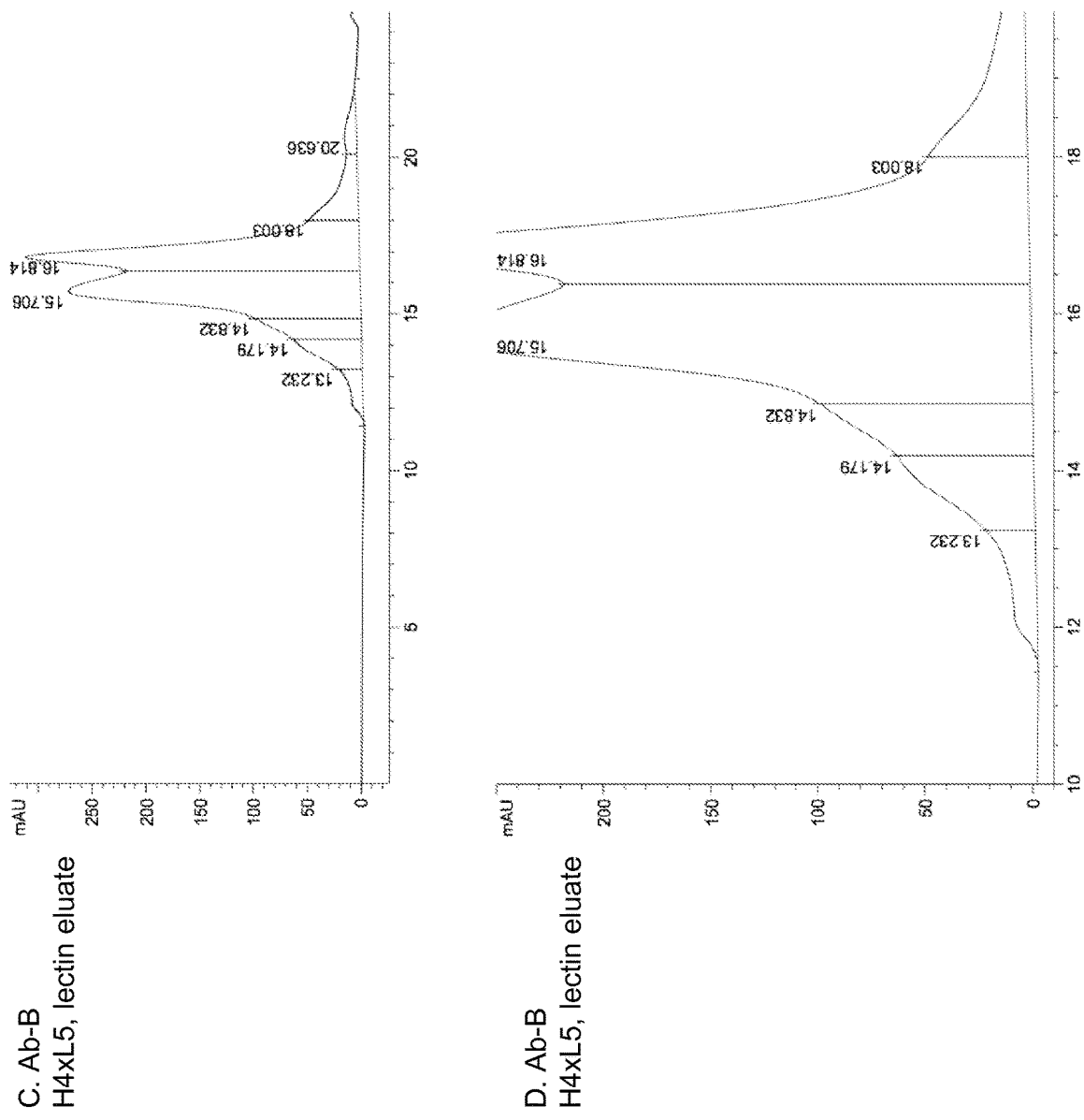
Figure 14:
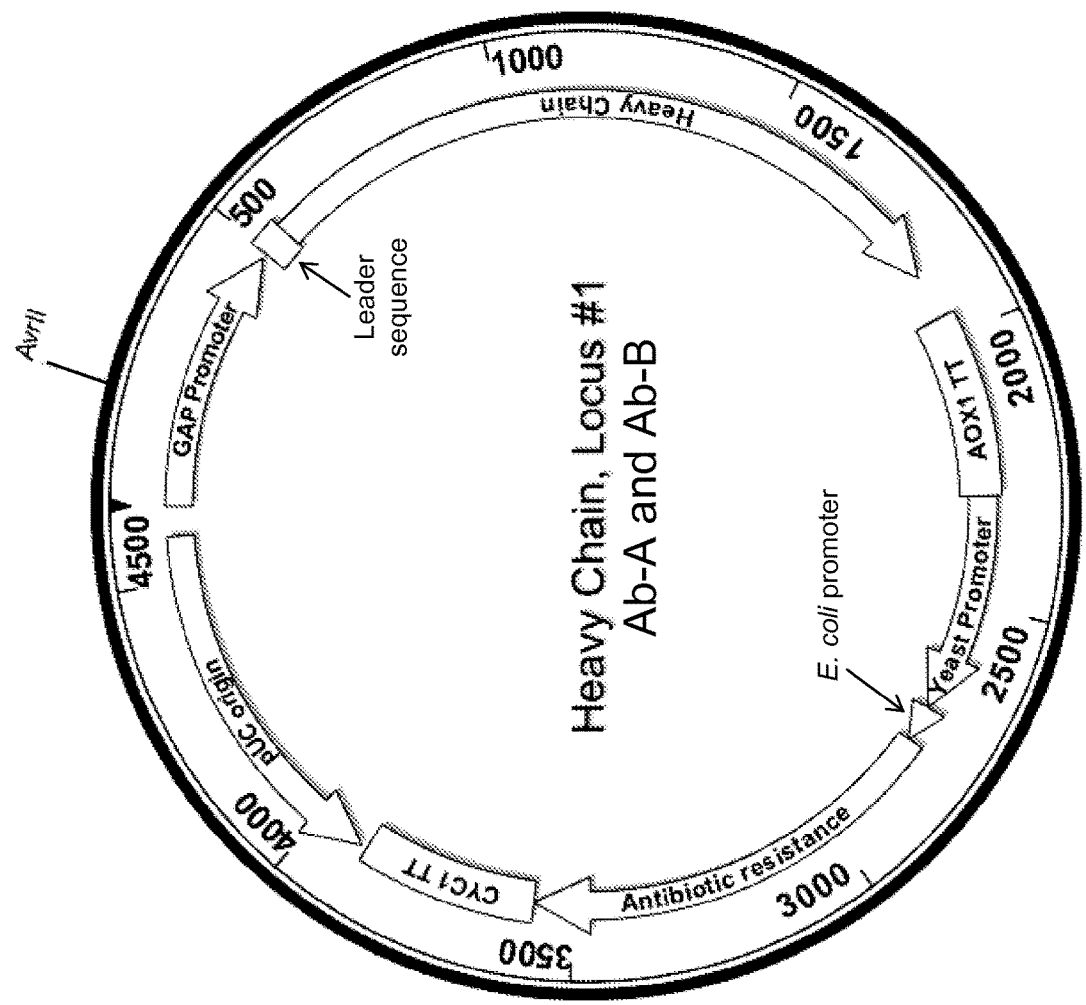
FIG. 14 shows a map of a construct used for targeted integration of an antibody heavy chain sequence for Ab-A or Ab-B into the pGAP locus (Locus #1).
Figure 15:
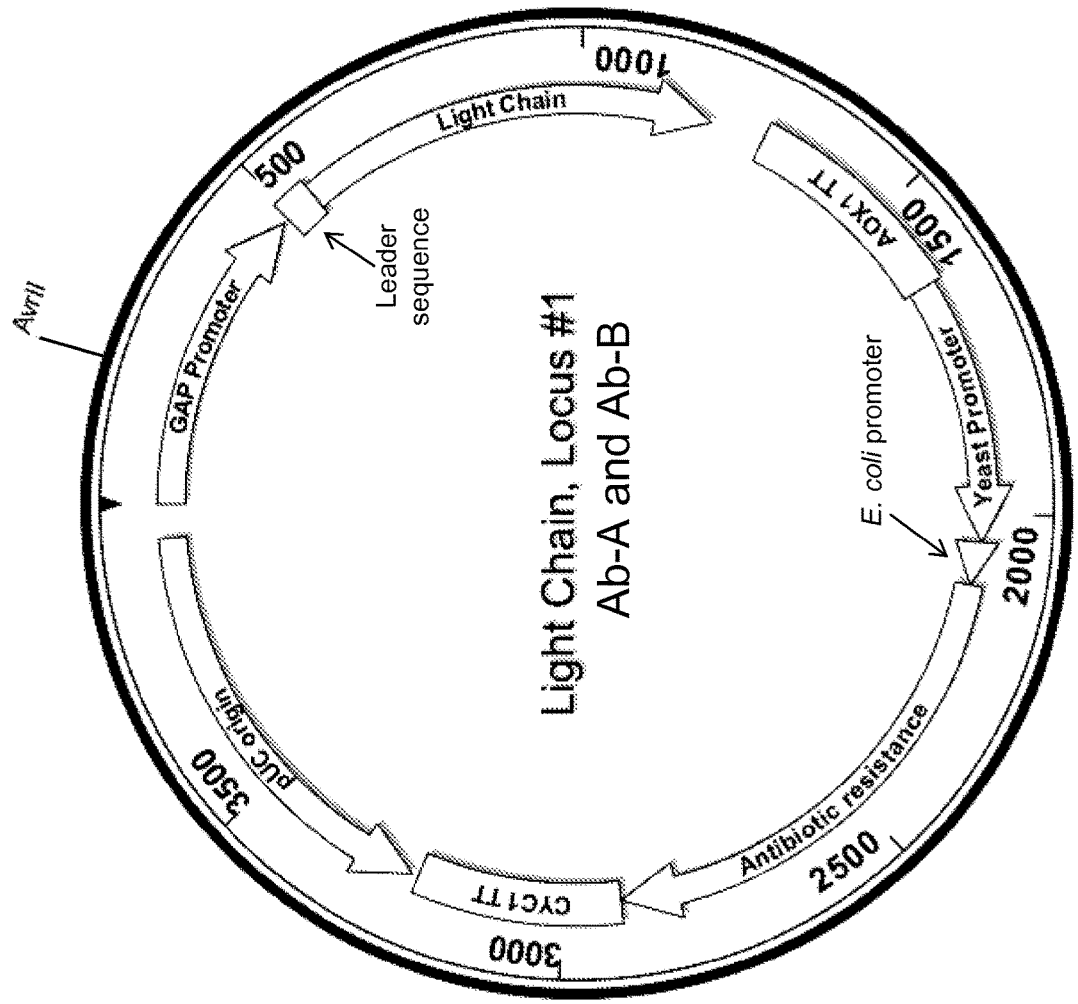
FIG. 15 shows a map of a construct used for targeted integration of an antibody light chain sequence for Ab-A or Ab-B into the pGAP locus (Locus #1).
Figure 16:
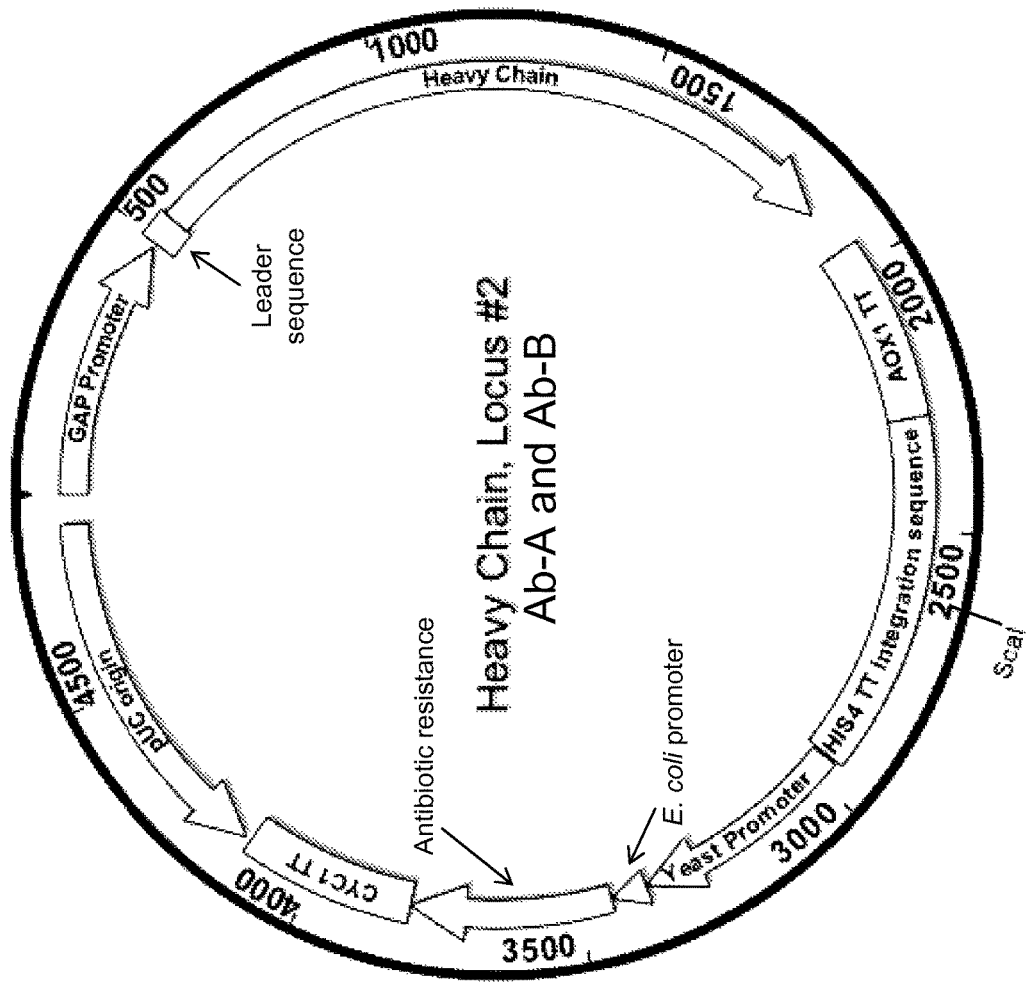
FIG. 16 shows a map of a construct used for targeted integration of an antibody heavy chain sequence for Ab-A or Ab-B into the HIS4 TT locus (Locus #2).
Figure 17:
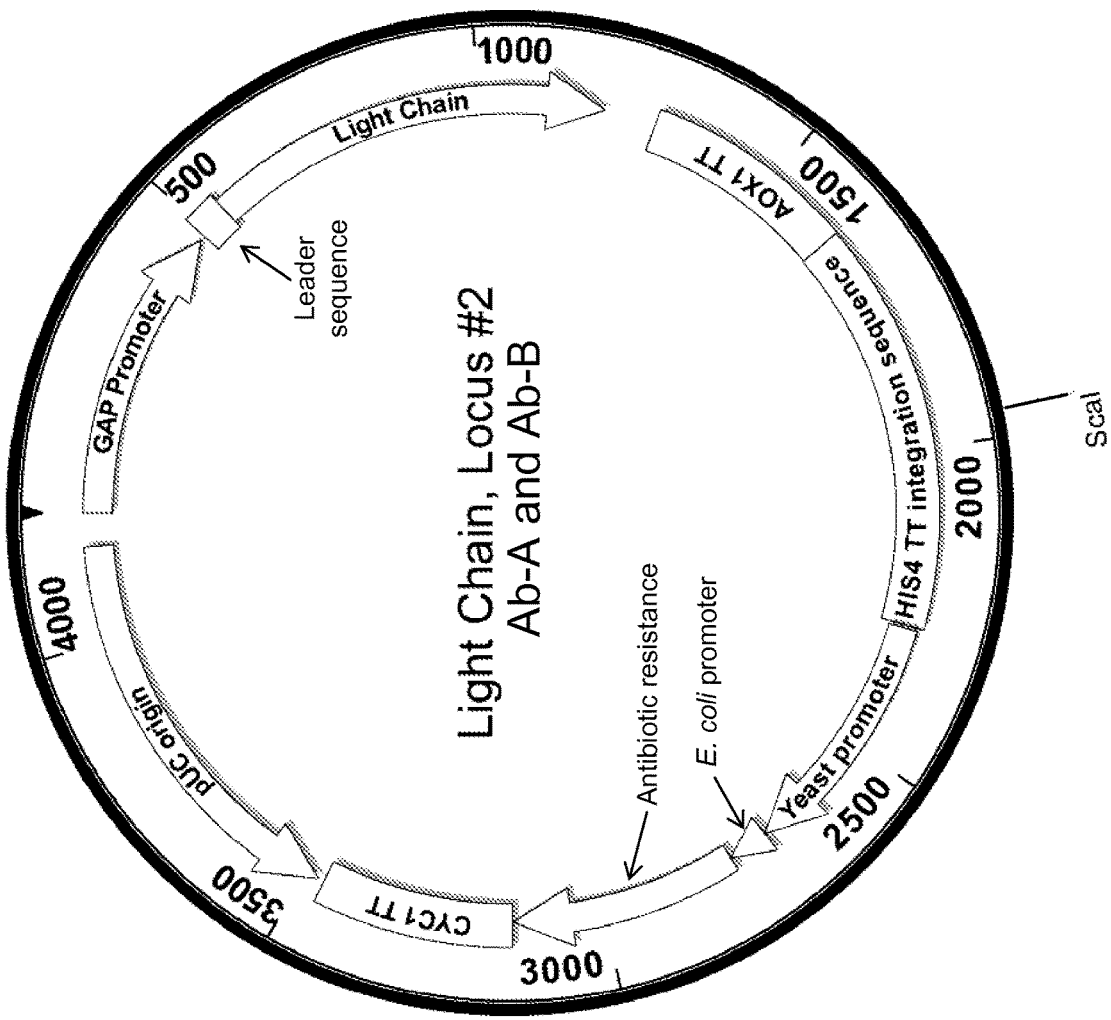
FIG. 17 shows a map of a construct used for targeted integration of an antibody light chain sequence for Ab-A or Ab-B into the HIS4 TT locus (Locus #2).
Figure 18:
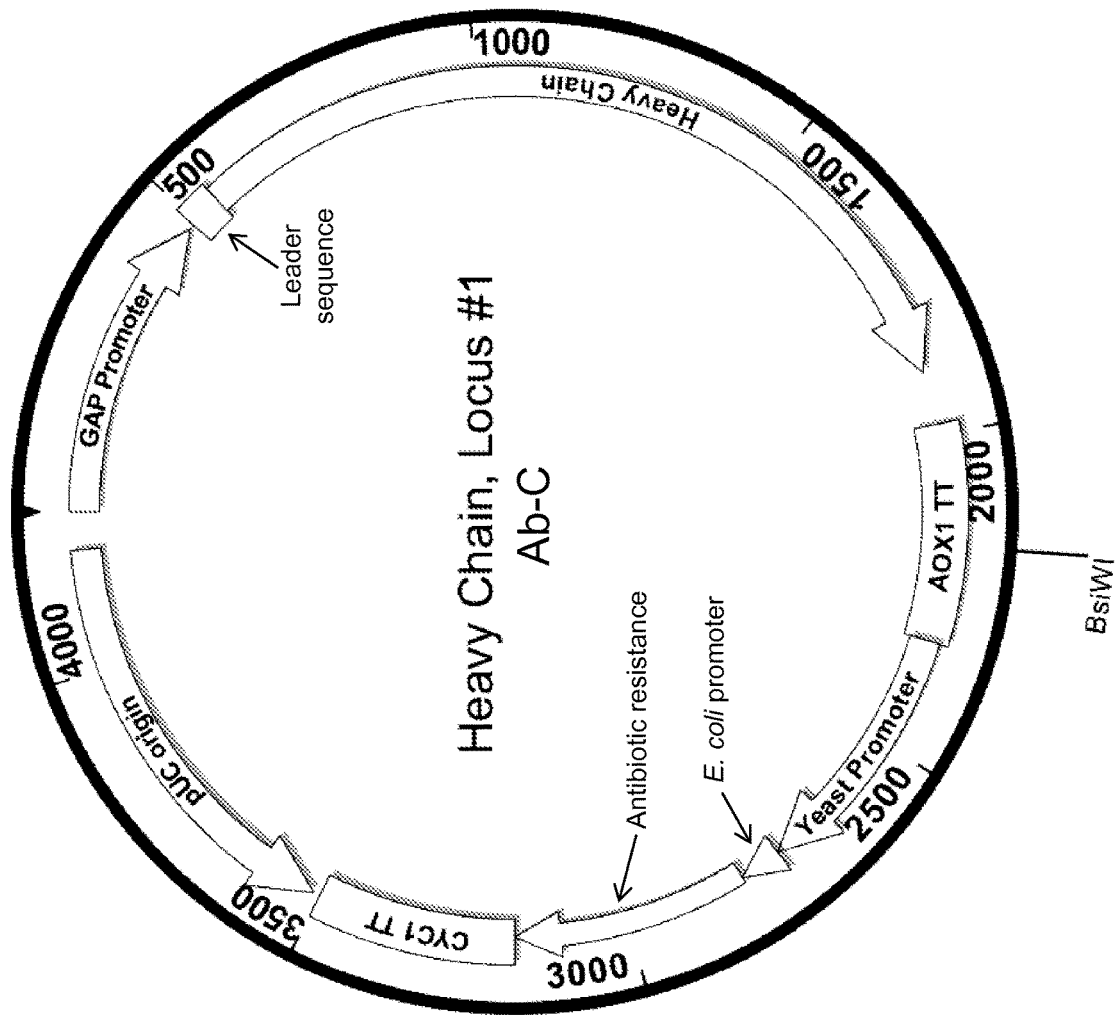
FIG. 18 shows a map of a construct used for targeted integration of an antibody heavy chain sequence for Ab-C into the AOX1 TT locus (Locus #1).

The fraction of the total mass contained in the expected peak and glyco-heavy peak in FIG. 12 and FIG. 13 are shown in Table 4 below. Comparison of the antibody preparations prior to lectin purification ("Load" column) provides a quantitative assessment of antibody purity and prevalence of the glyco heavy form. The relative abundance of the glyco heavy form in the H4×L5 preparation (2.7%) was less than half of what it was in the H4×L3 preparation (6%).

TABLE 4

Quantitative assessment of Ab-B purity in preparations from H4xL3 and H4xL5 strains by HPLC. Percentage of total protein mass contained in the "glyco form" (about 15.5 minutes retention time) and "main peak" (16.7 minutes retention time, corresponding to the expected antibody) is shown for preparations from each strain in the antibody preparation prior to ("Load") and after ("Lectin Eluate") purification with a lectin column.

|  | Load | Lectin Eluate |
|---|---|---|
| Ab-B H4xL3 glyco form | 6% | 58.6% |
| Ab-B H4xL3 main peak | 90.1% | 24.5% |
| Ab-B H4xL5 glyco form | 2.7% | 41.1% |
| Ab-B H4xL5 main peak | 89.6% | 36.1% |

Taken together, these results indicate that the proportion of glycosylated heavy chain can be altered by varying the heavy and light chain gene copy numbers. Thus, manipulation of the light and heavy gene copy numbers can effect a reduction in glycosylated antibody production when desired, and this can be accomplished by direct mating of selected haploid strains.

Example 4

Methods for Generation of a Cell Panel Containing Varying Copy Numbers of Antibody Genes This example describes methods used for the production of a panel of transformed yeast cells comprising variable numbers of copies of genes encoding each subunit of a heterologous multi-subunit protein, and mating of transformed cells to produce a panel of diploid cells that express the multi-subunit protein from varying numbers of gene copies. An overview of the strain generation methodology is shown in FIG. 1.

Construction of *Pichia pastoris* Expression Vectors for Heavy and Light Chain.

The light and heavy chain fragments were commercially synthesized and subcloned into a pGAP expression vector (FIGS. 14, 15, 18, and 20). The pGAP expression vector uses the GAP promoter to drive expression of the immunoglobulin chain. In addition, this vector contains common elements such as a bacterial origin of replication and an expression cassette for antibiotic resistance. For Ab-A and Ab-B, the GAP promoter sequence (about 500 basepairs in length) was used for targeting integration into this locus. The vector includes a copy of the kanamycin resistance gene which confers resistance to the antibiotic G418 in *P. pastoris*. For Ab-C, the AOX1 transcription terminator sequence (about 350 basepairs in length) was used for targeting integration into this locus. The vector includes a copy of the Sh ble gene, which confers resistance to the antibiotic Zeocin™ (phleomycin). G418 and Zeocin™ provide a means of selection for strains that contain the desired expression vector integrated into their genome. Finally, for Ab-A, Ab-B and Ab-C, the vector used for the second round of integration includes 660 basepairs of *P. pastoris* genomic sequence surrounding the HIS4 transcription terminator used for targeting integration into this locus (FIGS. 13, 14, 16, and 17). For Ab-A and Ab-B, the vector used for the second round of transformation includes a copy of the Sh ble gene. For Ab-C, the vector used for the second round of transformation includes a copy of the kanamycin resistance gene.

Transformation of Expression Vectors into Haploid Met1 and Lys3 Host Strains of *Pichia pastoris*

*P. pastoris* cells were transformed by electroporation following a modified protocol from *Pichia* Protocols, Second Edition (Methods in Molecular Biology, Cregg, J M, Ed. 2007. Humana Press, Totowa, N.J.). The transformed strains were derived from JC231 (Lys) or JC239 (Met). A 3-mL YPD (1% yeast extract, 2% peptone, 2% dextrose) culture was inoculated with a *P. pastoris* colony for each host strain and allowed to grow overnight with shaking at 30° C. These cultures were then used to inoculate 400-mL YPD cultures in 2 L Thomson shake flasks at a starting $OD_{600}$ of 0.01. Cells were harvested when $OD_{600}$ reached 1.0-2.0 and resuspended in 100 mL YPD medium containing 0.2M HEPES (pH 8.0) and 0.025M DTT. Cells were incubated at 30° C. for 30 minutes, and the volume was then brought up to 400 mL using 1M cold sorbitol. Cells were washed once in 400 mL 1M cold sorbitol, followed by three times in 30 mL cold sorbitol before resuspending in a final volume of 1 mL of 1M cold sorbitol.

Figure 19:
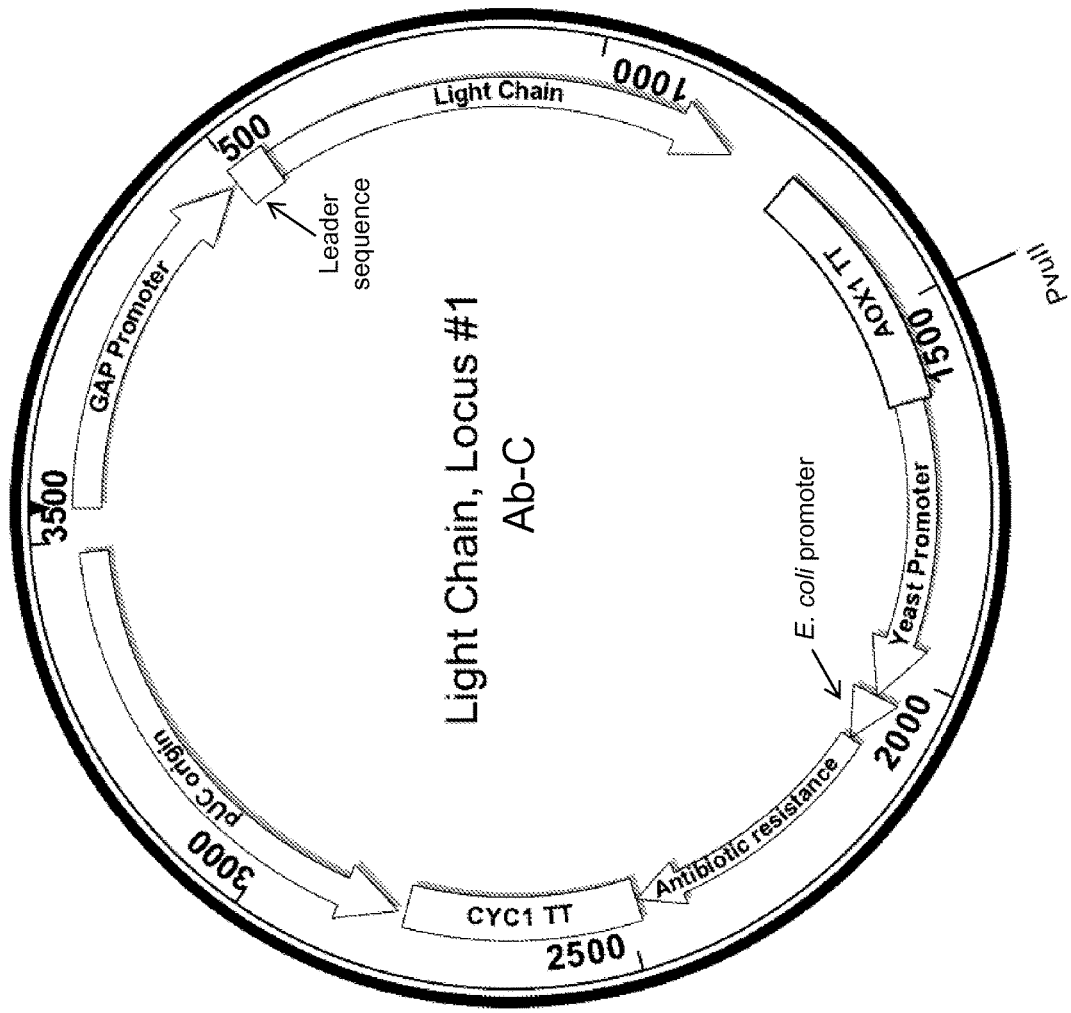
FIG. 19 shows a map of a construct used for targeted integration of an antibody light chain sequence for Ab-C into the AOX1 TT locus (Locus #1).
Figure 20:
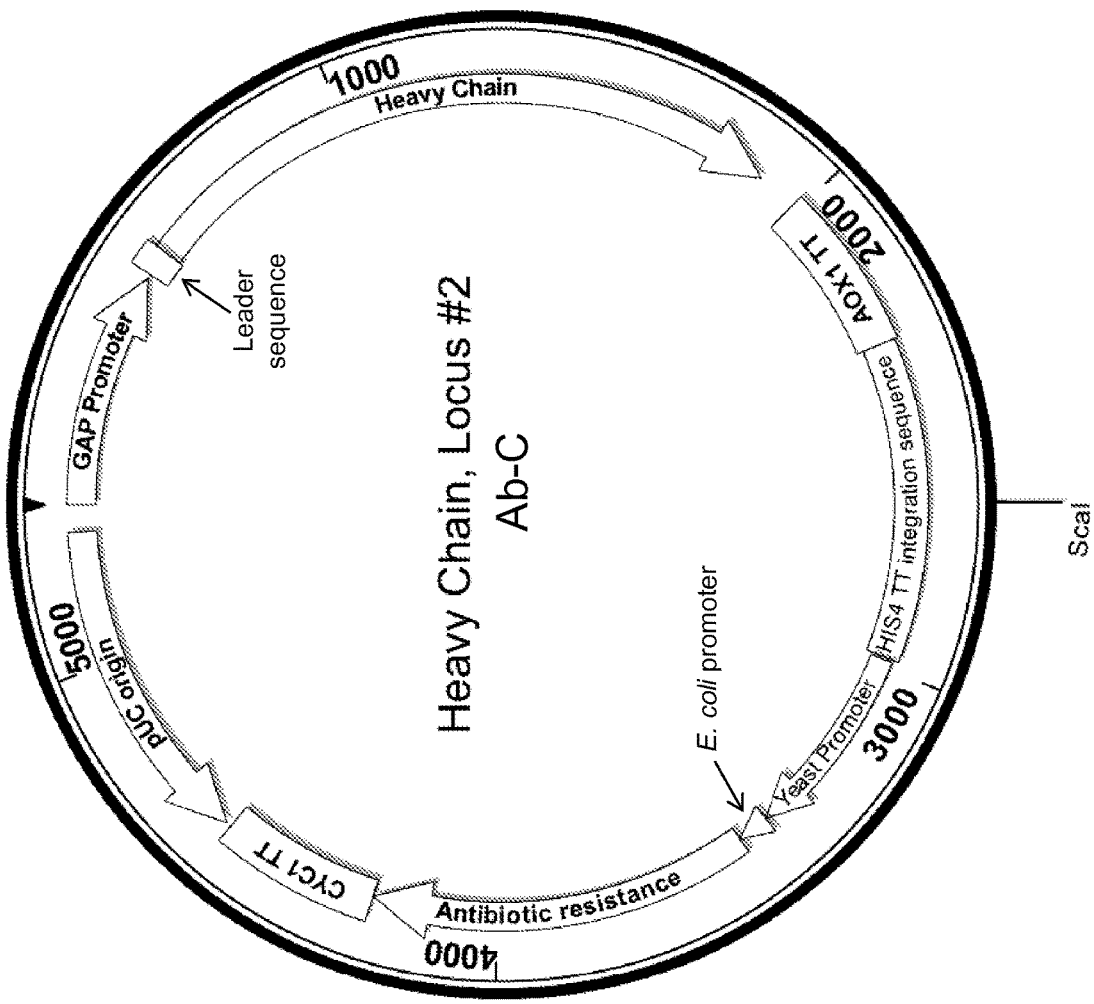
FIG. 20 shows a map of a construct used for targeted integration of an antibody heavy chain sequence for Ab-C into the HIS4 TT locus (Locus #2).
Figure 21:
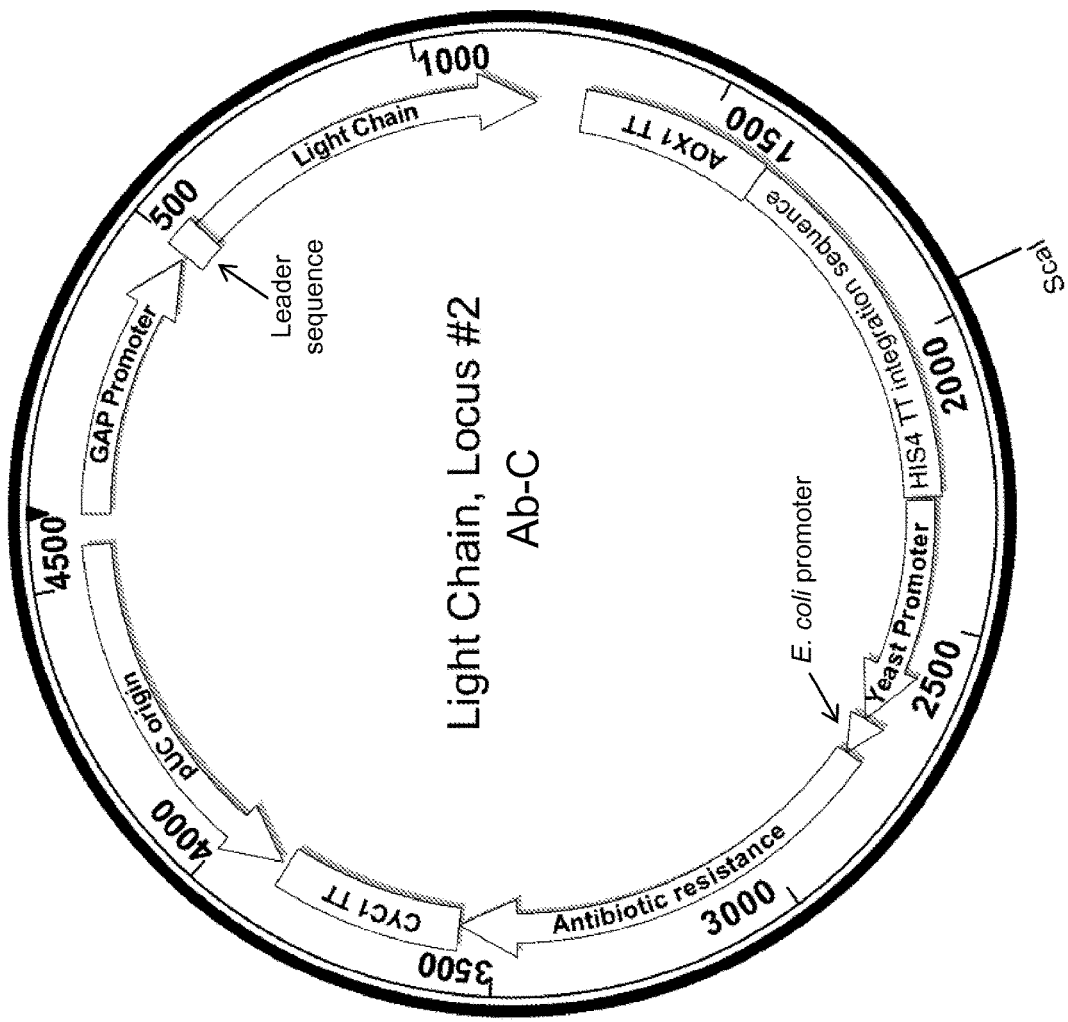
FIG. 21 shows a map of a construct used for targeted integration of an antibody light chain sequence for Ab-C into the HIS4 TT locus (Locus #2).

For preferred integration of Ab-A or Ab-B into the GAP promoter, prior to transformation each vector (FIGS. 14-15) was linearized within the GAP promoter sequences using AvrII restriction endonuclease to direct the integration of the vector into the GAP promoter locus of the *P. pastoris* genome. For preferred integration of Ab-C into the AOX1 transcription terminator, each vector (FIGS. 18-19) was linearized within the 3'AOX TT sequence using either BsiWI (for heavy chain) or PvuII (for light chain). For Ab-A and Ab-B, successful transformants were selected on YPDS (1% yeast extract, 2% peptone, 2% dextrose, 2% agar, 1M sorbitol) agar plates containing G418. For Ab-C, successful transformants were selected on YPDS agar plates containing Zeocin™. This is referred to as the first locus integration. For Ab-A and Ab-C, fluorescence activated cell sorting (FACS) was used to enrich for clones containing higher copies of heavy or light chain. Briefly, transformation plates were scraped in approximately 5 mL PBS. Cells were stained with fluorescence detection antibodies specific for either heavy or light chain. Positive cells were detectable by FACS even though the genes of interest were fused to secretion signals, which was apparently due to at least transient retention of some protein at the cell surface. The top 20-40% of the stained cells were sorted and used to inoculate 25 mL BYED (3% yeast extract, 4% anhydrous dextrose, 1.34% yeast nitrogen base, 0.004% Biotin, and 100 mM potassium phosphate) shake flask cultures. After growing overnight at 30° C. with shaking, cells were harvested, stained, and enriched a second time using FACS. The top 10-20% of the stained cells were streaked to single colony on YPD plates containing G418 (for Ab-A) or Zeocin™ (for Ab-C). The FACS enrichment assay was omitted for Ab-B.

Varying numbers of copies of the construct integrated in tandem into the targeted locus (illustrated in FIG. 22). Copy numbers of heavy and light chain genes were determined for haploid strains by Southern blot analysis. In brief, genomic DNA was digested with a restriction enzyme that cleaves sequences flanking the integration site, resolved by agarose gel electrophoresis, transferred to a membrane, and hybridized to a probe consisting of the integration sequence. The size of the restriction fragment increases linearly with the number of integrated copies (see FIG. 22). If the size of the genomic restriction fragment prior to integration is Y and the length of the integrated sequence is X, then the fragment size after integration of N copies will be Y+NX. Using this relationship, the number of copies per transformant was determined from the length of the detected fragment.

Haploid strains with desired copy numbers were then mated and selected for their ability to grow in the absence of both auxotroph markers (i.e., Lys and Met) on BYNB (1.34% yeast nitrogen base, 2.5% agar, 2% dextrose, 0.1M potassium phosphate pH 6.0) agar plates. Resulting diploid clones were then analyzed by Southern blot to confirm copy numbers of heavy and light chain genes. Diploid clones expressing full length monoclonal antibodies were further characterized by 48 hr growth in a deep-well plate containing 1 mL of BSM (basal salt media, 10 g/L sodium citrate dihydrate, 36.4 g/L ammonium phosphate monobasic, 18.2 g/L potassium sulfate, 12.8 g/L potassium phosphate monobasic, 3.7 g/L magnesium sulfate heptahydrate, 40 g/L dextrose, 40 g/L yeast extract, 4.35 mL/L PTM1 solution, pH 6.0) containing 4% yeast extract. Antibody concentrations in the supernatants were then quantified using biolayer interferometry Protein A biosensors (Octet, ForteBio).

For integration into a second genomic locus, competent cells for the transformation were prepared using haploid strains containing a pre-determined copy number of heavy chain or light chain as per the protocol described above. For preferred integration into the HIS4 TT locus, each expression vector (FIGS. 16-17 and 20-21) was linearized within the HIS4 TT integration sequence using Sca1 restriction endonuclease to direct integration into that locus. For Ab-A and Ab-B, successful transformants were selected on YPDS agar plates containing Zeocin™. For Ab-C, successful transformants were selected on YPDS agar plates containing G418. Copy numbers of heavy and light chain genes integrated at the HIS4 TT locus were determined using Southern blot. Haploid strains were mated, and diploid strains were selected as described above. A final Southern blot was done to confirm copy numbers of heavy and light chain genes at each of the integration loci. A clone was selected using Protein A biosensors to monitor expression (Octet, ForteBio).

Southern Blotting

Copy numbers of heavy and light chain genes were determined for haploid strains by Southern blot analysis. Single colonies were selected from YPD agar plates and used to inoculate 3-mL YPD cultures. Cultures were incubated overnight at 30° C. with shaking until saturated. Genomic DNA was extracted from 1.8 mL of each culture using the MasterPure Yeast DNA Purification Kit (Epicentre) following the manufacturer's protocol. For the pGAP locus, one microgram of DNA was digested with Cla I and separated on a 0.8% TAE agarose gel. Following electrophoresis, the gel was treated with denaturing buffer (0.5M NaOH; 1.5M NaCl) for 45 minutes and neutralization buffer (0.5M Tris-HCl, pH 7.2; 1.5M NaCl; 1 mM EDTA) for 30 minutes. DNA was then transferred to a positively charged nylon membrane (BioRad) by capillary action and fixed using a UV crosslinker. The membrane was hybridized overnight at 41° C. using a digoxigenin (DIG)-labeled DNA probe corresponding to the pGAP sequence. The membrane was washed under high stringency conditions and detected using the DIG High Prime Labeling and Detection Kit (Roche Applied Science). Hybridized bands were visualized by exposing the membrane to X-ray film.

Copy numbers of heavy and light chain genes integrated at the 3'AOX TT or HIS4 TT loci were determined using Southern blot following the steps described above, with some modifications. For the AOX1 transcription terminator locus, HindIII restriction endonuclease was used for the genomic DNA digestion, and a DIG-labeled probe corresponding to the 3'AOX TT sequence was used for hybridization. For the HIS4 TT locus, SspI restriction endonuclease was used for the genomic DNA digestion, and a DIG-labeled probe corresponding to the HIS4 TT sequence was used for hybridization.

Using the foregoing methodology, a panel of transformants containing varying numbers of copies of the individual subunits are obtained, for example, strains labeled H3, H4, H5 and H6 containing three, four, five and six copies, respectively, of an antibody heavy chain, and strains labeled L3 through L7 containing three through seven copies, respectively, of an antibody light chain. These transformants are then mated to obtain diploids containing varying numbers of copies of the light and heavy chain genes, and gene copy numbers are optionally reconfirmed by Southern blot. Diploid cells containing known, varying copy numbers of the light and heavy chain genes are thereby produced. Optionally, a clone expressing the antibody of interest was selected using biolayer interferometry Protein-A biosensors to monitor expression (Octet, ForteBio). Frozen stocks of the resulting haploid and/or diploid strains are typically produced, and transformants are propagated for evaluation of yield, production rate, and purity of the mature antibody.

Generation of a Panel of *P. pastoris* Strains Containing a Varying Number of Copies of the Light and Heavy Chain Genes Encoding Ab-A A panel of *P. pastoris* strains for expression of Ab-A containing variable numbers of copies of the light and heavy chain genes was produced using the methods described above. A total of thirteen diploid strains were produced containing between two and five copies of the heavy chain gene and between two and seven copies of the light chain gene. Initially, haploid strains containing defined numbers of copies of the light chain and heavy chain genes were produced (each haploid strain being either Lys⁻ or Met⁻), then mating between these haploid strains was used to produce diploid prototroph strains containing a known number of copies of the light and heavy chain genes. Each expression cassette was composed of the glyceraldehyde dehydrogenase gene (GAP gene) promoter, fused to a sequences encoding a secretion signal, followed by the sequence of the gene to be expressed, followed by sequences encoding a *P. pastoris* transcriptional termination signal from the *P. pastoris* alcohol oxidase I gene (AOX1) alone or in combination with the HIS4 TT sequence (illustrated in FIGS. 14-21).

Transformants containing a gene encoding the Ab-A heavy chain integrated into the pGAP locus were assigned the identifiers Hc47 through Hc60. Purified genomic DNA was digested with a restriction enzyme that cleaved sites flanking the pGAP locus, and Southern blotting (using a labeled pGAP sequence) was used to determine the number of integrated copies in each strain as described above (FIG. 23). Lane 1 and the two rightmost lanes contain labeled DNA ladders (fragment sizes are written at the left edge of the blot). Lanes 2 through 15 correspond to strains Hc47 through Hc60, respectively. The labels A through C at the right edge of the blot indicate the expected size of the fragment from a strain containing one through three copies, respectively, of the integrated sequence. The fragment detected in strains Hc58 and Hc51 indicated that these strains contained two and three copies, respectively, of the heavy chain gene. Strains Hc58 and Hc51 were selected for mating.

Similarly, a panel of haploid *P. pastoris* strains were produced that contained varying numbers of genomic copies of a gene encoding Ab-A light chain, also integrated into the pGAP locus. The strains were assigned the identifiers Lc1 through Lc27. Purified genomic DNA was digested with a restriction enzyme that cleaved sites flanking the pGAP locus, and Southern blotting (using a labeled pGAP sequence) was used to determine the number of integrated copies in each strain (FIG. 24). Lanes 1 and 22 contain a labeled DNA ladder (fragment sizes are written at the left edge of the blot). Lanes 2 through 21 and 23 through 29 correspond to strains Lc1 to Lc27, respectively. The labels A through F at the right edge of the blot indicate the expected size of the fragment from a strain containing one through five copies and more than 5 copies, respectively, of the integrated sequence. The fragment detected in strains Lc17, Lc7, and Lc27 indicated that these strains contained two, three, and four copies, respectively, of the light chain gene. Strains Lc17, Lc7, and Lc27 were selected for mating.

To further increase the number of copies of the heavy and light chain genes available in the panel, additional gene copies were integrated into a second locus. The total copy number of a specific integrated gene is therefore calculated by adding the number of copies from both integration loci. Specifically, additional copies of a gene encoding Ab-A heavy chain were integrated into the HIS4 TT locus in a strain already containing 3 copies of the Ab-A heavy chain gene integrated in the pGAP locus, thereby introducing one or two additional copies of the heavy chain gene, for a total of four or five copies. Similarly, additional copies of a gene encoding the Ab-A light chain were integrated into the HIS4 TT locus in a strain already containing 3 copies of the Ab-A light chain gene integrated in the pGAP locus, thereby introducing one to four additional copies of the light chain gene, for a total of four to seven copies.

Diploid strains were then produced by mating strains containing heavy and light chain genes. A total of thirteen different strains were produced containing between two and five copies of the heavy chain gene and between two and seven copies of the light chain gene. For each diploid strain, the number of copies of the heavy and light chain genes is indicated by the strain identifier (e.g., Ab-B-H4×L5 indicates 4 copies of the heavy chain gene and five copies of the light chain gene) and the loci from which the genes are expressed are identified in Table 1, above.

Multiple isolates of each diploid strains were generated by mating, and copy numbers were verified by Southern blotting before selecting particular isolates for further analysis. FIG. 25 shows Southern blots of the pGAP locus to verify gene copy numbers for candidates of the Ab-A-H3×L3, Ab-A-H3×L4, Ab-A-H2×L3, and Ab-A-H2×L2 strains (lanes 2-6, 7-11, 12-15, and 16-19, respectively), and asterisks indicate candidates that were selected for further use. Lane 1 contains a labeled DNA ladder (fragment sizes are written at the left edge of the blot). The labels A, C, and E at the right edge of the blot indicate the expected size of the fragment from a strain containing two through four copies, respectively, of the light chain gene, and the labels B and D, indicate the expected size of the fragment from a strain containing two or three copies, respectively, of the heavy chain gene. FIG. 26 shows Southern blots for verification of the gene copy numbers at the pGAP locus for isolates of the strains shown in Table 1, and asterisks indicate the isolates that were selected for further use. The labels A, C, and E at the right edge of the blot indicate the expected size of the fragment from a strain containing one through three copies, respectively, of the heavy chain gene, and the labels B and D, indicate the expected size of the fragment from a strain containing two or three copies, respectively, of the light chain gene. Similarly, FIG. 27 shows Southern blots for verification of the gene copy numbers at the HIS4 TT locus for those strains expected to contain antibody genes integrated at that locus (identified in Table 1). The label A at the right edge of the blot indicates the expected size of a fragment containing an endogenous HIS4 TT locus, the labels B, D, F, and G indicate the expected size of the fragment from a strain containing one through four copies, respectively, of the light chain gene, and the labels C and E, indicate the expected size of the fragment from a strain containing one or two copies, respectively, of the heavy chain gene.

Generation of a Panel of P. *Pastoris* Strains Containing a Varying Number of Copies of the Light and Heavy Chain Genes Encoding Ab-B Haploid strains containing genes encoding the heavy and light chains of Ab-B (targeted to the pGAP locus) were generated using essentially the same methods described for Ab-A. Southern blots (using a pGAP sequence probe) identified strains Hc3 and Hc4 containing 2 and 3 copies, respectively, of the Ab-B heavy chain gene (FIG. 28A), and strains Lc5, Lc11, Lc12, and Lc9 containing 2 through 5 copies, respectively, of the Ab-B light chain gene (FIG. 28B). In FIG. 28A, the labels A, C, E, and G at the right side of the blot indicate the expected size of the fragment containing zero to three copies, respectively, of the Ab-B heavy chain gene integrated into the pGAP locus, and in FIG. 28B, the labels A, B, D, F, H, and I at the left side of the blot indicate the expected size of the fragment containing zero to five copies, respectively, of the Ab-B light chain gene integrated into the pGAP locus. Asterisks indicate haploid strains selected for further mating.

To further increase the number of copies of the heavy chain gene available in the panel, additional copies of a gene encoding Ab-B heavy chain were integrated into the HIS4 TT locus in a strain already containing 3 copies of the Ab-B heavy chain gene integrated in the pGAP locus, thereby introducing one or two additional copies of the heavy chain gene, for a total of four or five copies. Similarly, additional copies of a gene encoding the Ab-B light chain were integrated in to the HIS4 TT locus in a strain already containing 3 copies of the Ab-B light chain gene integrated in the pGAP locus, thereby introducing one to four additional copies of the light chain gene, for a total of four to seven copies.

Diploid strains were then produced by mating strains containing heavy and light chain genes. A total of fourteen different strains were produced containing between two and five copies of the heavy chain gene and between two and seven copies of the light chain gene. For each diploid strain, the number of copies of the heavy and light chain genes is indicated by the strain identifier (e.g., H4×L5 indicates 4 copies of the heavy chain gene and five copies of the light chain gene) and the loci from which the genes are expressed are identified in Table 2, above. Gene copy numbers in the diploid strains were reconfirmed by Southern blots shown in FIGS. 29-30 (pGAP probe) and FIG. 31 (HIS4 TT probe). Multiple isolates of each diploid strain were generated, and asterisks in FIGS. 29-31 indicate isolates selected for further use. In FIG. 29, the labels A, C, and E at the right side of the blot indicate the expected size of the fragment containing one to three copies, respectively, of the Ab-B heavy chain gene integrated into the pGAP locus, and the labels B, D, F, and G indicate the expected size of the fragment containing two to five copies, respectively, of the Ab-B light chain gene integrated into the pGAP locus. In FIG. 30, the labels A, B, C, and E at the right side of the blot indicate the expected size of the fragment containing zero to three copies, respectively, of the Ab-B heavy chain gene integrated into the pGAP locus, and the labels A and D indicate the expected size of the fragment containing zero and three copies, respectively, of the Ab-B light chain gene integrated into the pGAP locus. In FIG. 31, the labels A, C, and E indicate the expected size of the fragment containing zero to two copies, respectively, of the Ab-B heavy chain gene integrated into the HIS4 TT locus, and the labels A, B, D, F, and G indicate the expected size of the fragment containing zero to four copies, respectively, of the Ab-B light chain gene integrated into the HIS4 TT locus.

Generation of a Panel of P. *pastoris* Strains Containing a Varying Number of Copies of the Light and Heavy Chain Genes Encoding Ab-C A panel of P. *pastoris* strains for expression of Ab-C containing variable numbers of copies of the light and heavy chain genes was produced using essentially the same methods for Ab-A and Ab-B. Southern blots (using a 3'AOX TT sequence probe) identified haploid strains Hc 19, Hc25, Hc13, and Hc17 containing 1, 2, 3, and 4 copies, respectively, of the Ab-C heavy chain gene (FIG. 32), and strains Lc7, Lc6, Lc11, Lc19, Lc15, and Lc17 containing 1 through 6 copies, respectively, of the Ab-C light chain gene (FIG. 33). In FIG. 32, the labels A, B, C, and D on the right side of the blot indicate the expected size of the fragment containing one to four copies, respectively, of the Ab-C heavy chain gene integrated into the AOX1 transcription terminator locus. In FIG. 33, the labels A, B, C, D, E, and F at the right side of the blot indicated the expected fragment size containing one to six copies, respectively, of the Ab-C light chain gene integrated at the AOX1 transcription terminator locus. Asterisks indicated haploids selected for further mating.

To further increase the number of copies of the heavy and light chain genes available in the panel, additional gene copies were integrated into a second locus. The total copy number of a specific integrated gene is therefore calculated by adding the number of copies from both integration loci. Specifically, additional copies of a gene encoding Ab-C heavy chain were integrated into the HIS4 TT locus in a strain already containing 3 or 4 copies of the Ab-C heavy chain gene integrated in the AOX1 transcription terminator locus, thereby introducing one or two additional copies of the heavy chain gene, for a total of five or six copies. Similarly, additional copies of a gene encoding the Ab-C light chain were integrated into the HIS4 TT locus in a strain already containing 3 or 4 copies of the Ab-C light chain gene integrated in the AOX1 transcription terminator locus, thereby introducing two additional copies of the light chain gene, for a total of five or six copies.

Diploid strains were then produced by mating haploids containing heavy and light chain genes. A total of nine different strains were produced containing between three and six copies of the heavy chain gene and between three and six copies of the light chain gene. For each diploid strain, the number of copies of the heavy and light chain genes is indicated by the strain identifier (e.g., Ab-C-H4×L5 indicates 4 copies of the heavy chain gene and five copies of the light chain gene) and the loci from which the genes are expressed are identified in Table 3, above. Gene copy numbers in the diploid strains were reconfirmed by Southern blots shown in FIGS. 34-35 (3'AOX TT probe) and FIG. 36 (HIS4 TT probe). Multiple isolates of each diploid strain were generated, and asterisks in FIGS. 34-36 indicate isolates selected for further use. In FIG. 34, the labels B and D at the right side of the blot indicate the expected size of the fragment containing three or four copies, respectively, of the Ab-C heavy chain gene integrated into the AOX1 transcription terminator locus, and the labels A, C, and E indicate the expected size of the fragment containing three to five copies, respectively, of the Ab-C light chain gene integrated into the AOX1 transcription terminator locus. In FIG. 35, the labels A, C, and E at the right side of the blot indicate the expected size of the fragment containing two to four copies, respectively, of the Ab-C heavy chain gene integrated into the AOX1 transcription terminator locus, and the labels B and D indicate the expected size of the fragment containing three and four copies, respectively, of the Ab-C light chain gene integrated into the AOX1 transcription terminator locus. In FIG. 36 the label A indicates the expected size of the fragment containing zero copies of the Ab-C heavy or light chain gene integrated into the HIS4 TT locus, the label B indicates the expected size of the fragment containing two copies of the Ab-C light chain gene integrated into the HIS4 TT locus, and label C indicates the expected size of the fragment containing two copies of the Ab-C heavy chain gene integrated into the HIS4 TT locus.

The Ab-C-H3×L3 expression strain was constructed using a slightly different method. Prior to transformation, each expression vector (FIGS. 18-19) was linearized in the pGAP sequence using AvrII to direct integration of the vectors into the GAP promoter locus. Haploid P. pastoris JC231 (Lys⁻) or JC239 (Met⁻) cells were then transformed individually with the linearized heavy or light chain vectors, respectively, by electroporation following a modified protocol from Pichia Protocols, Second Edition (Methods in Molecular Biology, Cregg, J M, Ed. 2007. Humana Press, Totowa, N.J.). Successful transformants were selected on YPDS agar plates containing Zeocin™. To generate a library of diploid clones that express full-length Ab-C, the haploid transformant colonies were pooled, mixed together, and spread on mating medium agar plates. These were incubated for 24 hours at 30° C. Cells were then scraped from the mating plates and streaked onto BYNB agar plates to select for diploid clones. The ability of each diploid clone to express full-length antibody was assessed by a colony lift/immunoblot method (Wung et al. Biotechniques 21 808-812 (1996)). Briefly, secreted antibodies produced by the clones were transferred to a nitrocellulose membrane by touching the membrane to the plates. The filters were processed using a Western blot protocol employing a Goat anti-Human F(ab')2 HRP (horseradish peroxidase) detection antibody. Using chemiluminescence detection, colonies that expressed elevated levels of Ab-C were visualized on film. A large fraction of these colonies were picked into 96-deep well plates containing 300 µL of BYPD (1% yeast nitrogen base, 2% peptone, 2% glucose, 0.1M potassium phosphate pH 6, and 50 µg/mL Zeocin™). Cultures were grown for 60 hours at 30° C. with constant shaking. The resulting supernatants were assayed by a standard enzyme-linked immunosorbent assay (ELISA). From this, a single diploid clone was selected as having high expression of Ab-C. Southern blot analysis to determine copy numbers of heavy and light chain genes was subsequently performed on the final clone following the methods described above.

Example 5

Methods for Expression of Antibodies in a Bioreactor.
This example describes methods for production of antibodies in a bioreactor for further characterization or use.
First, an inoculum was expanded using the research cell bank using medium comprised of the following nutrients (% w/v): yeast extract 3%, anhydrous dextrose 4%, YNB 1.34%, Biotin 0.004% and 100 mM potassium phosphate. To generate the inoculum for the fermenters, the cell bank was expanded for approximately 24 hours in a shaking incubator at 30° C. and 300 rpm. A 10% inoculum was then added to Labfors 2.5 L working volume vessels containing 1 L sterile growth medium. The growth medium was comprised of the following nutrients: potassium sulfate 18.2 g/L, ammonium phosphate monobasic 36.4 g/L, potassium phosphate dibasic 12.8 g/L, magnesium sulfate heptahydrate 3.72 g/L, sodium citrate dihydrate 10 g/L, glycerol 40 g/L, yeast extract 30 g/L, PTM1 trace metals 4.35 mL/L, and antifoam 204 1.67 mL/L. The PTM1 trace metal solution was comprised of the following components: cupric sulfate pentahydrate 6 g/L, sodium iodide 0.08 g/L, manganese sulfate hydrate 3 g/L, sodium molybdate dihyrate 0.2 g/L, boric acid 0.02 g/L, cobalt chloride 0.5 g/L, zinc chloride 20 g/L, ferrous sulfate heptahydrate 65 g/L, biotin 0.2 g/L, and sulfuric acid 5 mL/L.

The bioreactor process control parameters were set as follows: Agitation 1000 rpm, airflow 1.35 standard liter per minute, temperature 28° C. and pH was controlled (at 6) using ammonium hydroxide. No oxygen supplementation was provided.

Fermentation cultures were grown for approximately 12 to 16 hours until the initial glycerol was consumed as denoted by a dissolved oxygen spike. The cultures were starved for approximately three hours after the dissolved oxygen spike. After this starvation period, a bolus addition of ethanol was added to the reactor to reach 1% ethanol (w/v). The fermentation cultures were allowed to equilibrate for 15 to 30 minutes. Feed addition was initiated 30 minutes post-ethanol bolus and set at a constant rate of 1 mL/min for 40 minutes, then the feed pump was controlled by an ethanol sensor keeping the concentration of ethanol at 1% for the remainder of the run using an ethanol sensing probe (Raven Biotech). The feed was comprised of the following components: yeast extract 50 g/L, dextrose monohydrate 500 g/L, magnesium sulfate heptahydrate 3 g/L, and PTM1 trace metals 12 mL/L. Optionally, sodium citrate dihydrate (0.5 g/L) was also added to the feed. The total fermentation time was approximately 90 hours (T90).

Antibody yield was then determined using analytic high pressure liquid chromatography (HPLC) and fitted with a Protein A affinity column. A purified antibody sample was used to determine a standard curve by integrating the optical absorbance at 280 nm ($A_{280}$) in the HPLC peak.

Example 6

Methods for Determination of Antibody Yield and Purity by HPLC
To analyze the purity of protein-A purified antibody preparations, size exclusion high-pressure liquid chromatography (SE-HPLC) was used. Briefly, an Agilent (Santa Clara, Calif.) 1200 Series HPLC with UV detection instrument was used. For sample separation, a TSKgel GS3000SWx1 7.8×300 mM column connected with a TSKgel Guard SWx1 6×40 mM from Tosoh Bioscience (King of Prussia, Pa.) was used. A 100 mM sodium phosphate, 200 mM sodium chloride pH 6.5 was used as mobile phase with a flow rate of 0.5 mL/min in isocratic mode and absorbance at UV 215 nm was monitored. Before injection of samples the column was equilibrated until a stable baseline was achieved. Samples were diluted to a concentration of 1 mg/mL using mobile phase and a 30 µL volume was injected. To monitor column performance, BioRad (Hercules, Calif.) gel filtration standards were used.

Example 7

Methods for Antibody Purification by Protein-A Affinity

For characterization of *Pichia pastoris* expressed antibodies, protein A purification was performed. Briefly, approximately 20 mL of 0.2µ clarified supernatants from harvested fermentation broth were diluted with the same volume of equilibration buffer (20 mM Histidine pH6). From this diluted broth, 20 mL were then loaded onto a pre-equilibrated 1 mL HiTrap MabSelect Sure column (GE, Piscataway, N.J.). The column was subsequently washed using 30 column volumes of equilibration buffer. The antibody bound onto the column was eluted using a step gradient into 100% elution buffer (100 mM Citric Acid pH 3.0). One mL fractions were collected and immediately neutralized using 100 µL of 2M Tris buffer pH 8.0. Protein containing fractions were determined by measuring absorbance at 280 nM and protein-containing fractions were pooled.

Example 8

Methods for Characterization of Impurities by SDS-PAGE, Western Blotting, and Lectin Column Purification SE-HPLC allowed us to quantitate the product-associated variant being modulated by the ratio of light chain to heavy chain expression in the different strains. To characterize the nature of this product-associated variant we did western blot analysis and purification using an affinity lectin column. Briefly, for western blot analysis, 5 µg samples were prepared in LDS sample loading buffer with NuPAGE reducing agent (Invitrogen, Carlsbad, Calif.), heated at 70 C for 10 minutes. The equivalent of four micrograms of sample were then loaded onto a 4-12% BisTris gradient gel and separated by electrophoresis using MES running buffer (Invitrogen, Carlsbad, Calif.). The proteins separated in the gel were then blotted onto a nitrocellulose membrane using an I-Blot (Invitrogen, Carlsbad, Calif.) and blocked for 60 minutes using a blocking solution (10% powdered milk solution in DPBS-T [DPBS solution containing 0.1% Tween-20 (Invitrogen, Carlsbad, Calif.)]). The blocked membrane was then probed for 30 minutes with a goat-anti-human FC peroxidase conjugated antibody (Jackson Immunoresearch Laboratories, Inc, West Grove, Pa.), using a 1:10,000 dilution in blocking solution. The blot was then washed for five minutes in a DPBS 0.1% Tween solution for a total of four times. For development the ECL advance chemiluminescent reagent (Amersham/GE, Piscataway, N.J.) was used and the image was captured using a CCD camara (Alpha Innotech/Cell Biosciences, Santa Clara, Calif.).

To further characterize the product-associated variant, we used agarose-bound *Galanthus nivalis* lectin (Vector Laboratories, Inc, Burlingame, Calif.). *Galantus nivalis* lectin is a small molecular weight protein that binds to mannose-containing proteins and does not require $Ca^{++}$ or $Mn^{++}$ for binding. For binding, 2 mL of resin was washed with 14 mL of DBS four times by resuspension-centrifugation. After wash, the beads were resuspended to a final 50% slurry concentration in DPBS and 4004 were added to Protein-A purified antibody samples containing 1.5 to 4 mgs of protein. The agarose-bound lectin was then incubated with the antibody at room temperature for 2.5 hours with continuous mixing. At the end of this incubation, the sample was spun, the supernatant collected and labeled as "flow-thru". The beads were then transferred onto an empty Bio-Rad drip column (Hercules, Calif.) and washed by gravity using DPBS. A total of 6 mL were used for washing using 0.5 mL at the time and monitoring 280 nm absorbance. Bound protein was eluted using 0.2M methyl-alpha-D-mannopyranoside. Samples, load and eluted proteins, were then analyzed by SDS-PAGE, and Western blot using an anti-Human Fc specific reagent, and SE-HPLC. SDS-PAGE was carried out using precast polyacrylamide gels (NuPAGE® Bis-Tris Gels) containing a 4%-12% polyacrylamide gradient, using NuPAGE® MES SDS running buffer and NuPAGE® LDS Sample Buffer (all from Invitrogen, Carlsbad, Ca.) in accord with the manufacturer's instructions. Prior to loading, samples were reduced using the NuPAGE® Sample Reducing Agent (Invitrogen, Carlsbad, Ca.) in accord with the manufacturer's instructions.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

The invention may be practiced in ways other than those particularly described in the foregoing description and examples. Numerous modifications and variations of the invention are possible in light of the above teachings and, therefore, are within the scope of the appended claims.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

Certain teachings related to methods for obtaining a clonal population of antigen-specific B cells were disclosed in U.S. Provisional patent application No. 60/801,412, filed May 19, 2006, the disclosure of which is herein incorporated by reference in its entirety.

Certain teachings related to humanization of rabbit-derived monoclonal antibodies and preferred sequence modifications to maintain antigen binding affinity were disclosed in International Application No. PCT/US2008/064421, corresponding to International Publication No. WO/2008/144757, entitled "Novel Rabbit Antibody Humanization Methods and Humanized Rabbit Antibodies", filed May 21, 2008, the disclosure of which is herein incorporated by reference in its entirety.

Certain teachings related to producing antibodies or fragments thereof using mating competent yeast and corresponding methods were disclosed in U.S. patent application Ser. No. 11/429,053, filed May 8, 2006, (U.S. Patent Application Publication No. US2006/0270045), the disclosure of which is herein incorporated by reference in its entirety.

The entire disclosure of each document cited herein (including patents, patent applications, journal articles, abstracts, manuals, books, or other disclosures), including each document cited in the Background, Summary, Detailed Description, and Examples, is hereby incorporated by reference herein in its entirety.

What is claimed is:

1. A diploid *Pichia pastoris* host cell identified as a host cell that produces a desired antibody comprised of a heavy and a light chain with a greater purity by a method comprising:

(a) providing a panel of *Pichia pastoris* host cells, said panel comprising at least two diploid *Pichia pastoris* host cells that each comprise genes that provide for expression of the light and heavy chain of the desired antibody;

wherein said at least two host diploid *Pichia pastoris* cells are each produced by mating or fusion of a first and a second haploid *Pichia pastoris* parental cell, wherein the first haploid *Pichia pastoris* parental cell comprises one or more copies of at least one gene encoding a light chain of said desired antibody wherein at least one of said light chain genes of said desired antibody is integrated into a first locus comprised on two homologous chromosomes via homologous recombination and at least one of said light chain genes of said desired antibody is integrated into a second locus also comprised on two homologous chromosomes via homologous recombination; and a second haploid *Pichia pastoris* parental cell which comprises one or more copies of at least one gene encoding a heavy chain of said desired antibody wherein at least one of said heavy chain genes of said desired antibody is integrated into the same first locus comprised on two homologous chromosomes via homologous recombination and at least one of said heavy chain genes of said desired antibody is integrated into the same second locus comprised on two homologous chromosomes via homologous recombination;

(b) culturing each of said diploid *Pichia pastoris* host cells to express the desired antibody, wherein the genes encoding the light and heavy chains of said desired antibody which are integrated in 2 different loci of said at least two diploid *Pichia pastoris* host cells provide for differing levels of expression of the light and heavy chains of said desired antibody;

(c) measuring the yield of the desired antibody produced by each of said diploid *Pichia pastoris* host cells; and (d) identifying the diploid *Pichia pastoris* host cell that produces a greater yield than another diploid *Pichia pastoris* host cell in said panel of diploid *Pichia pastoris* host cells as a host cell that produces a desired antibody with a greater purity;

and further wherein the total number of heavy chain genes integrated into said identified diploid *Pichia pastoris* cell ranges from 2 to 10 wherein at least 1 copy is present at a first and second gene loci and at most 7 copies are present at either of said 2 loci and the total number of integrated light chain genes ranges from 2 to 10 and at least 1 copy of said light chain genes is present at 2 different loci and at most 7 copies of said light chain genes is present at either of said 2 loci.

2. The diploid *Pichia pastoris* host cell of claim 1, wherein the respective number of copies of the gene encoding the heavy chain of said desired antibody and the number of copies of the gene encoding the light chain of said desired antibody in said diploid *Pichia pastoris* host cell are: 2 and 2, 2 and 3, 3 and 3, 3 and 4, 3 and 5, 4 and 3, 4 and 4, 4 and 5, 4 and 6, 5 and 4, 5 and 5, 5 and 6, or 5 and 7.

3. The host cell of claim 1, wherein the gene copies encoding the light and heavy chains of said desired antibody are respectively integrated into two loci wherein each of said two loci are on two homologous chromosomes.

4. The diploid *Pichia pastoris* host cell of claim 3, wherein each locus contains no more than 5 copies of a given antibody subunit, no more than 4 copies of a given antibody subunit, or no more than 3 copies of a given antibody subunit.

5. The diploid *Pichia pastoris* host cell of claim 3, wherein said 2 different gene loci comprise at least two of pGAP, HIS4 TT and AOX1 TT.

6. A culture medium containing a stable diploid *Pichia pastoris* yeast culture derived from the host cell of claim 1, wherein the culture medium comprises expression levels of said desired antibody which are at least about 50 mg/liter, 100 mg/liter, 500 mg/liter or 1000 mg/liter, 1500 mg/liter or more.

7. A culture medium containing a stable diploid *Pichia pastoris* yeast culture derived from the host cell of claim 1, that expresses said desired antibody into a culture medium wherein the cell density of said diploid cells in said culture are at least about 50 g/L, 100 g/L, 300 g/L, 400 g/L, 500 g/L, 700 g/L, or more.

8. The diploid *Pichia pastoris* host cell of claim 1, wherein the at least one of said different gene loci are selected from pGAP, HIS4 TT and AOX1 TT.

9. The diploid *Pichia pastoris* host cell of claim 1, wherein both of said different gene loci are selected from pGAP, HIS4 TT and AOX1 TT.

* * * * *

SEQUENCE LISTING

<160> NUMBER OF SEQ ID NOS: 54

<210> SEQ ID NO 1
<211> LENGTH: 441
<212> TYPE: PRT
<213> ORGANISM: Artificial
<220> FEATURE:
<223> OTHER INFORMATION: Humanized antibody sequence

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Val Ser Gly Leu Asp Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ile Asn Asp Asn Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Ala Arg
        195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Ala Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro

```
                    355                 360                 365
Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
                435                 440

<210> SEQ ID NO 2
<211> LENGTH: 111
<212> TYPE: PRT
<213> ORGANISM: Artificial
<220> FEATURE:
<223> OTHER INFORMATION: Humanized antibody sequence

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Val Ser Gly Leu Asp Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ile Asn Asp Asn Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
            100                 105                 110

<210> SEQ ID NO 3
<211> LENGTH: 5
<212> TYPE: PRT
<213> ORGANISM: Artificial
<220> FEATURE:
<223> OTHER INFORMATION: Humanized antibody sequence

<400> SEQUENCE: 3

Ser Tyr Tyr Met Gln
1               5

<210> SEQ ID NO 4
<211> LENGTH: 16
<212> TYPE: PRT
<213> ORGANISM: Artificial
<220> FEATURE:
<223> OTHER INFORMATION: Humanized antibody sequence

<400> SEQUENCE: 4

Val Ile Gly Ile Asn Asp Asn Thr Tyr Tyr Ala Ser Trp Ala Lys Gly
1               5                   10                  15

<210> SEQ ID NO 5
<211> LENGTH: 333
<212> TYPE: DNA
<213> ORGANISM: Artificial
```

<220> FEATURE:
<223> OTHER INFORMATION: Humanized antibody sequence

<400> SEQUENCE: 5

```
gaggtgcagc ttgtggagtc tgggggaggc ttggtccagc ctgggggtc  cctgagactc    60
tcctgtgcag tctctggact cgacctcagt agctactaca tgcaatgggt  ccgtcaggct   120
ccagggaagg ggctggagtg ggtcggagtc attggtatca atgataacac  atactacgcg   180
agctgggcga aaggccgatt caccatctcc agagacaatt ccaagaccac  ggtgtatctt   240
caaatgaaca gcctgagagc tgaggacact gctgtgtatt tctgtgctag  agggggacatc   300
tggggccaag ggaccctcgt caccgtctcg agc                                 333
```

<210> SEQ ID NO 6
<211> LENGTH: 1326
<212> TYPE: DNA
<213> ORGANISM: Artificial
<220> FEATURE:
<223> OTHER INFORMATION: Humanized antibody sequence

<400> SEQUENCE: 6

```
gaggtgcagc ttgtggagtc tgggggaggc ttggtccagc ctgggggtc  cctgagactc    60
tcctgtgcag tctctggact cgacctcagt agctactaca tgcaatgggt  ccgtcaggct   120
ccagggaagg ggctggagtg ggtcggagtc attggtatca atgataacac  atactacgcg   180
agctgggcga aaggccgatt caccatctcc agagacaatt ccaagaccac  ggtgtatctt   240
caaatgaaca gcctgagagc tgaggacact gctgtgtatt tctgtgctag  agggggacatc   300
tggggccaag ggaccctcgt caccgtctcg agcgcctcca  ccaagggccc  atcggtcttc   360
cccctggcac cctcctccaa gagcacctct ggggcacag  cggccctggg  ctgcctggtc   420
aaggactact tccccgaacc ggtgacggtg tcgtggaact  caggcgccct  gaccagcggc   480
gtgcacacct tcccggctgt cctacagtcc tcaggactct  actccctcag  cagcgtggtg   540
accgtgccct ccagcagctt gggcacccag acctacatct  gcaacgtgaa  tcacaagccc   600
agcaacacca aggtggacgc gagagttgag cccaaatctt  gtgacaaaac  tcacacatgc   660
ccaccgtgcc cagcacctga actcctgggg ggaccgtcag  tcttcctctt  ccccccaaaa   720
cccaaggaca cccctcatgat ctcccggacc cctgaggtca  catgcgtggt  ggtggacgtg   780
agccacgaag accctgaggt caagttcaac tggtacgtgg  acggcgtgga  ggtgcataat   840
gccaagacaa agccgcggga ggagcagtac gccagcacgt  accgtgtggt  cagcgtcctc   900
accgtcctgc accaggactg gctgaatggc aaggagtaca  agtgcaaggt  ctccaacaaa   960
gccctcccag cccccatcga gaaaaccatc tccaaagcca  agggcagcc  ccgagaacca  1020
caggtgtaca ccctgccccc atcccgggag gagatgacca  gaaccaggt  cagcctgacc  1080
tgcctggtca aaggcttcta tcccagcgac atcgccgtgg  agtgggagag  caatgggcag  1140
ccggagaaca actacaagac cacgcctccc gtgctggact  ccgacggctc  cttcttcctc  1200
tacagcaagc tcaccgtgga caagagcagg tggcagcagg  ggaacgtctt  ctcatgctcc  1260
gtgatgcatg aggctctgca caaccactac acgcagaaga  gcctctccct  gtctccgggt  1320
aaatga                                                              1326
```

<210> SEQ ID NO 7
<211> LENGTH: 219
<212> TYPE: PRT
<213> ORGANISM: Artificial
<220> FEATURE:

<223> OTHER INFORMATION: Humanized antibody sequence

<400> SEQUENCE: 7

```
Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asp Asn Asn
                20                  25                  30

Tyr Leu Ala Trp Tyr Gln Gln Lys Pro Gly Lys Val Pro Lys Gln Leu
            35                  40                  45

Ile Tyr Ser Thr Ser Thr Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Ser Gly Asp Cys Phe Val Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 8
<211> LENGTH: 113
<212> TYPE: PRT
<213> ORGANISM: Artificial
<220> FEATURE:
<223> OTHER INFORMATION: Humanized antibody sequence

<400> SEQUENCE: 8

```
Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asp Asn Asn
                20                  25                  30

Tyr Leu Ala Trp Tyr Gln Gln Lys Pro Gly Lys Val Pro Lys Gln Leu
            35                  40                  45

Ile Tyr Ser Thr Ser Thr Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Ser Gly Asp Cys Phe Val Phe Gly Gly Gly Thr Lys Val Glu Ile Lys
                100                 105                 110

Arg
```

<210> SEQ ID NO 9
<211> LENGTH: 13
<212> TYPE: PRT
<213> ORGANISM: Artificial
<220> FEATURE:
<223> OTHER INFORMATION: Humanized antibody sequence

<400> SEQUENCE: 9

Gln Ala Ser Gln Ser Val Tyr Asp Asn Asn Tyr Leu Ala
1               5                   10

<210> SEQ ID NO 10
<211> LENGTH: 7
<212> TYPE: PRT
<213> ORGANISM: Artificial
<220> FEATURE:
<223> OTHER INFORMATION: Humanized antibody sequence

<400> SEQUENCE: 10

Ser Thr Ser Thr Leu Ala Ser
1               5

<210> SEQ ID NO 11
<211> LENGTH: 13
<212> TYPE: PRT
<213> ORGANISM: Artificial
<220> FEATURE:
<223> OTHER INFORMATION: Humanized antibody sequence

<400> SEQUENCE: 11

Leu Gly Ser Tyr Asp Cys Ser Ser Gly Asp Cys Phe Val
1               5                   10

<210> SEQ ID NO 12
<211> LENGTH: 339
<212> TYPE: DNA
<213> ORGANISM: Artificial
<220> FEATURE:
<223> OTHER INFORMATION: Humanized antibody sequence

<400> SEQUENCE: 12
caagtgctga cccagtctcc atcctccctg tctgcatctg taggagacag agtcaccatc        60
aattgccagg ccagtcagag tgtttatgat aacaactacc tagcctggta tcagcagaaa       120
ccagggaaag ttcctaagca actgatctat tctacatcca ctctggcatc tggggtccca       180
tctcgtttca gtggcagtgg atctgggaca gatttcactc tcaccatcag cagcctgcag       240
cctgaagatg ttgcaactta ttactgtcta ggcagttatg attgtagtag tggtgattgt       300
tttgttttcg gcggaggaac caaggtggaa atcaaacgt                              339

<210> SEQ ID NO 13
<211> LENGTH: 660
<212> TYPE: DNA
<213> ORGANISM: Artificial
<220> FEATURE:
<223> OTHER INFORMATION: Humanized antibody sequence

<400> SEQUENCE: 13
caagtgctga cccagtctcc atcctccctg tctgcatctg taggagacag agtcaccatc        60
aattgccagg ccagtcagag tgtttatgat aacaactacc tagcctggta tcagcagaaa       120
ccagggaaag ttcctaagca actgatctat tctacatcca ctctggcatc tggggtccca       180
tctcgtttca gtggcagtgg atctgggaca gatttcactc tcaccatcag cagcctgcag       240

```
cctgaagatg ttgcaactta ttactgtcta ggcagttatg attgtagtag tggtgattgt    300
tttgttttcg gcggaggaac caaggtggaa atcaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660
```

<210> SEQ ID NO 14
<211> LENGTH: 441
<212> TYPE: PRT
<213> ORGANISM: Artificial
<220> FEATURE:
<223> OTHER INFORMATION: Humanized antibody sequence

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
            20                  25                  30

Tyr Met Asn Trp Val Arg Gln Ala Pro Gly Lys Gly Leu Glu Trp Val
        35                  40                  45

Gly Val Ile Gly Ile Asn Gly Ala Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Ala Arg
        195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Ala Ser Thr Tyr Arg Val Val Ser Val Leu Thr Val Leu His
```

```
                    290                 295                 300
Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
                340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
        370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser Leu Ser Pro Gly Lys
            435                 440

<210> SEQ ID NO 15
<211> LENGTH: 111
<212> TYPE: PRT
<213> ORGANISM: Artificial
<220> FEATURE:
<223> OTHER INFORMATION: Humanized antibody sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
            20                  25                  30

Tyr Met Asn Trp Val Arg Gln Ala Pro Gly Lys Gly Leu Glu Trp Val
        35                  40                  45

Gly Val Ile Gly Ile Asn Gly Ala Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
            100                 105                 110

<210> SEQ ID NO 16
<211> LENGTH: 5
<212> TYPE: PRT
<213> ORGANISM: Artificial
<220> FEATURE:
<223> OTHER INFORMATION: Humanized antibody sequence

<400> SEQUENCE: 16

Gly Tyr Tyr Met Asn
1               5

<210> SEQ ID NO 17
<211> LENGTH: 15
<212> TYPE: PRT
<213> ORGANISM: Artificial
<220> FEATURE:
```

<223> OTHER INFORMATION: Humanized antibody sequence

<400> SEQUENCE: 17

Ile Gly Ile Asn Gly Ala Thr Tyr Tyr Ala Ser Trp Ala Lys Gly
1               5                   10                  15

<210> SEQ ID NO 18
<211> LENGTH: 333
<212> TYPE: DNA
<213> ORGANISM: Artificial
<220> FEATURE:
<223> OTHER INFORMATION: Humanized antibody sequence

<400> SEQUENCE: 18

| gaggtgcagc ttgtggagtc tgggggaggc ttggtccagc ctggggggtc cctgagactc | 60 |
| tcctgtgcag tctctggaat cgacctcagt ggctactaca tgaactgggt ccgtcaggct | 120 |
| ccagggaagg ggctggagtg gtcggagtc attggtatta atggtgccac atactacgcg | 180 |
| agctgggcga aaggccgatt caccatctcc agagacaatt ccaagaccac ggtgtatctt | 240 |
| caaatgaaca gcctgagagc tgaggacact gctgtgtatt tctgtgctag aggggacatc | 300 |
| tggggccaag ggaccctcgt caccgtctcg agc | 333 |

<210> SEQ ID NO 19
<211> LENGTH: 1326
<212> TYPE: DNA
<213> ORGANISM: Artificial
<220> FEATURE:
<223> OTHER INFORMATION: Humanized antibody sequence

<400> SEQUENCE: 19

| gaggtgcagc ttgtggagtc tgggggaggc ttggtccagc ctggggggtc cctgagactc | 60 |
| tcctgtgcag tctctggaat cgacctcagt ggctactaca tgaactgggt ccgtcaggct | 120 |
| ccagggaagg ggctggagtg gtcggagtc attggtatta atggtgccac atactacgcg | 180 |
| agctgggcga aaggccgatt caccatctcc agagacaatt ccaagaccac ggtgtatctt | 240 |
| caaatgaaca gcctgagagc tgaggacact gctgtgtatt tctgtgctag aggggacatc | 300 |
| tggggccaag ggaccctcgt caccgtctcg agcgcctcca caagggccc atcggtcttc | 360 |
| cccctggcac cctcctccaa gagcacctct gggggcacag cggccctggg ctgcctggtc | 420 |
| aaggactact ccccgaacc ggtgacggtg tcgtggaact caggcgccct gaccagcggc | 480 |
| gtgcacacct tcccggctgt cctacagtcc tcaggactct actccctcag cagcgtggtg | 540 |
| accgtgccct ccagcagctt gggcacccag acctacatct gcaacgtgaa tcacaagccc | 600 |
| agcaacacca aggtggacgc gagagttgag cccaaatctt gtgacaaaac tcacacatgc | 660 |
| ccaccgtgcc cagcacctga actcctgggg gaccgtcag tcttcctctt ccccccaaaa | 720 |
| cccaaggaca ccctcatgat ctcccggacc cctgaggtca catgcgtggt ggtggacgtg | 780 |
| agccacgaag accctgaggt caagttcaac tggtacgtgg acggcgtgga ggtgcataat | 840 |
| gccaagacaa agccgcggga ggagcagtac gccagcacgt accgtgtggt cagcgtcctc | 900 |
| accgtcctgc accaggactg gctgaatggc aaggagtaca agtgcaaggt ctccaacaaa | 960 |
| gccctcccag cccccatcga gaaaaccatc tccaaagcca agggcagcc cgagaaccca | 1020 |
| caggtgtaca ccctgccccc atcccgggag gagatgacca agaaccaggt cagcctgacc | 1080 |
| tgcctggtca aaggcttcta tcccagcgac atcgccgtgg agtgggagag caatgggcag | 1140 |
| ccggagaaca actacaagac cacgcctccc gtgctggact ccgacggctc cttcttcctc | 1200 |

```
tacagcaagc tcaccgtgga caagagcagg tggcagcagg ggaacgtctt ctcatgctcc   1260
gtgatgcatg aggctctgca caaccactac acgcagaaga gcctctccct gtctccgggt   1320
aaatga                                                              1326
```

<210> SEQ ID NO 20
<211> LENGTH: 219
<212> TYPE: PRT
<213> ORGANISM: Artificial
<220> FEATURE:
<223> OTHER INFORMATION: Humanized antibody sequence

<400> SEQUENCE: 20

```
Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr His Asn Thr
            20                  25                  30

Tyr Leu Ala Trp Tyr Gln Gln Lys Pro Gly Lys Val Pro Lys Gln Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Thr
                85                  90                  95

Asn Gly Asp Cys Phe Val Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 21
<211> LENGTH: 113
<212> TYPE: PRT
<213> ORGANISM: Artificial
<220> FEATURE:
<223> OTHER INFORMATION: Humanized antibody sequence

<400> SEQUENCE: 21

```
Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr His Asn Thr
            20                  25                  30

Tyr Leu Ala Trp Tyr Gln Gln Lys Pro Gly Lys Val Pro Lys Gln Leu
        35                  40                  45

Ile Tyr Asp Ala Ser Thr Leu Ala Ser Gly Val Pro Ser Arg Phe Ser
    50                  55                  60
```

```
Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Thr
                85                  90                  95

Asn Gly Asp Cys Phe Val Phe Gly Gly Gly Thr Lys Val Glu Ile Lys
            100                 105                 110

Arg

<210> SEQ ID NO 22
<211> LENGTH: 13
<212> TYPE: PRT
<213> ORGANISM: Artificial
<220> FEATURE:
<223> OTHER INFORMATION: Humanized antibody sequence

<400> SEQUENCE: 22

Gln Ala Ser Gln Ser Val Tyr His Asn Thr Tyr Leu Ala
1               5                   10

<210> SEQ ID NO 23
<211> LENGTH: 7
<212> TYPE: PRT
<213> ORGANISM: Artificial
<220> FEATURE:
<223> OTHER INFORMATION: Humanized antibody sequence

<400> SEQUENCE: 23

Asp Ala Ser Thr Leu Ala Ser
1               5

<210> SEQ ID NO 24
<211> LENGTH: 13
<212> TYPE: PRT
<213> ORGANISM: Artificial
<220> FEATURE:
<223> OTHER INFORMATION: Humanized antibody sequence

<400> SEQUENCE: 24

Leu Gly Ser Tyr Asp Cys Thr Asn Gly Asp Cys Phe Val
1               5                   10

<210> SEQ ID NO 25
<211> LENGTH: 339
<212> TYPE: DNA
<213> ORGANISM: Artificial
<220> FEATURE:
<223> OTHER INFORMATION: Humanized antibody sequence

<400> SEQUENCE: 25
caagtgctga cccagtctcc atcctccctg tctgcatctg taggagacag agtcaccatc      60
aattgccagg ccagtcagag tgtttatcat aacacctacc tggcctggta tcagcagaaa    120
ccagggaaag ttcctaagca actgatctat gatgcatcca ctctggcatc tggggtccca    180
tctcgtttca gtggcagtgg atctgggaca gatttcactc tcaccatcag cagcctgcag    240
cctgaagatg ttgcaactta ttactgtctg ggcagttatg attgtactaa tggtgattgt    300
tttgttttcg gcggaggaac caaggtggaa atcaaacgt                            339

<210> SEQ ID NO 26
<211> LENGTH: 660
<212> TYPE: DNA
<213> ORGANISM: Artificial
<220> FEATURE:
```

<223> OTHER INFORMATION: Humanized antibody sequence

<400> SEQUENCE: 26

| | | | | | |
|---|---|---|---|---|---|
| caagtgctga | cccagtctcc | atcctccctg | tctgcatctg | taggagacag | agtcaccatc | 60 |
| aattgccagg | ccagtcagag | tgtttatcat | aacacctacc | tggcctggta | tcagcagaaa | 120 |
| ccagggaaag | ttcctaagca | actgatctat | gatgcatcca | ctctggcatc | tggggtccca | 180 |
| tctcgtttca | gtggcagtgg | atctgggaca | gatttcactc | tcaccatcag | cagcctgcag | 240 |
| cctgaagatg | ttgcaactta | ttactgtctg | gcagttatg | attgtactaa | tggtgattgt | 300 |
| tttgttttcg | gcggaggaac | caaggtggaa | atcaaacgta | cggtggctgc | accatctgtc | 360 |
| ttcatcttcc | cgccatctga | tgagcagttg | aaatctggaa | ctgcctctgt | tgtgtgcctg | 420 |
| ctgaataact | tctatcccag | agaggccaaa | gtacagtgga | aggtggataa | cgccctccaa | 480 |
| tcgggtaact | cccaggagag | tgtcacagag | caggacagca | aggacagcac | ctacagcctc | 540 |
| agcagcaccc | tgacgctgag | caaagcagac | tacgagaaac | acaaagtcta | cgcctgcgaa | 600 |
| gtcacccatc | agggcctgag | ctcgcccgtc | acaaagagct | tcaacagggg | agagtgttag | 660 |

<210> SEQ ID NO 27
<211> LENGTH: 1350
<212> TYPE: DNA
<213> ORGANISM: Artificial
<220> FEATURE:
<223> OTHER INFORMATION: Humanized antibody sequence

<400> SEQUENCE: 27

| | | | | | |
|---|---|---|---|---|---|
| gaggtgcagc | tggtggagtc | tgggggaggc | ttggtccagc | ctggggggtc | cctgagactc | 60 |
| tcctgtgcag | cctctggatt | ctccctcagt | aactactacg | tgacctgggt | ccgtcaggct | 120 |
| ccagggaagg | ggctggagtg | ggtcggcatc | atctatggta | gtgatgaaac | cgcctacgct | 180 |
| acctccgcta | taggccgatt | caccatctcc | agagacaatt | ccaagaacac | cctgtatctt | 240 |
| caaatgaaca | gcctgagagc | tgaggacact | gctgtgtatt | actgtgctag | agatgatagt | 300 |
| agtgactggg | atgcaaagtt | caacttgtgg | ggccaaggga | ccctcgtcac | cgtctcgagc | 360 |
| gcctccacca | agggcccatc | ggtcttcccc | ctggcaccct | cctccaagag | cacctctggg | 420 |
| ggcacagcgg | ccctgggctg | cctggtcaag | gactacttcc | ccgaaccggt | gacggtgtcg | 480 |
| tggaactcag | gcgccctgac | cagcggcgtg | cacaccttcc | cggctgtcct | acagtcctca | 540 |
| ggactctact | ccctcagcag | cgtggtgacc | gtgccctcca | gcagcttggg | cacccagacc | 600 |
| tacatctgca | acgtgaatca | caagcccagc | aacaccaagg | tggacaagag | agttgagccc | 660 |
| aaatcttgtg | acaaaactca | cacatgccca | ccgtgcccag | cacctgaact | cctgggggga | 720 |
| ccgtcagtct | tcctcttccc | cccaaaaccc | aaggacaccc | tcatgatctc | ccggacccct | 780 |
| gaggtcacat | gcgtggtggt | ggacgtgagc | cacgaagacc | ctgaggtcaa | gttcaactgg | 840 |
| tacgtggacg | gcgtggaggt | gcataatgcc | aagacaaagc | cgcggagga | gcagtacgcc | 900 |
| agcacgtacc | gtgtggtcag | cgtcctcacc | gtcctgcacc | aggactggct | gaatggcaag | 960 |
| gagtacaagt | gcaaggtctc | caacaaagcc | ctcccagccc | ccatcgagaa | aaccatctcc | 1020 |
| aaagccaaag | gcagccccg | agaaccacag | gtgtacaccc | tgcccccatc | ccgggaggag | 1080 |
| atgaccaaga | accaggtcag | cctgacctgc | ctggtcaaag | gcttctatcc | cagcgacatc | 1140 |
| gccgtggagt | gggagagcaa | tgggcagccg | gagaacaact | acaagaccac | gcctcccgtg | 1200 |
| ctggactccg | acggctcctt | cttcctctac | agcaagctca | ccgtggacaa | gagcaggtgg | 1260 |
| cagcagggga | acgtcttctc | atgctccgtg | atgcatgagg | ctctgcacaa | ccactacacg | 1320 | cagaagagcc tctccctgtc tccgggtaaa                                    1350

<210> SEQ ID NO 28
<211> LENGTH: 450
<212> TYPE: PRT
<213> ORGANISM: Artificial
<220> FEATURE:
<223> OTHER INFORMATION: Humanized antibody sequence

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Val Thr Trp Val Arg Gln Ala Pro Gly Lys Gly Leu Glu Trp Val
        35                  40                  45

Gly Ile Ile Tyr Gly Ser Asp Glu Thr Ala Tyr Ala Thr Ser Ala Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 29
<211> LENGTH: 651
<212> TYPE: DNA
<213> ORGANISM: Artificial
<220> FEATURE:
<223> OTHER INFORMATION: Humanized antibody sequence

<400> SEQUENCE: 29
gctatccaga tgacccagtc tccttcctcc ctgtctgcat ctgtaggaga cagagtcacc     60
atcacttgcc aggccagtca gagcattaac aatgagttat cctggtatca gcagaaacca    120
gggaaagccc ctaagctcct gatctatagg gcatccactc tggcatctgg ggtcccatca    180
aggttcagcg gcagtggatc tgggacagac ttcactctca ccatcagcag cctgcagcct    240
gatgattttg caacttatta ctgccaacag ggttatagtc tgaggaacat tgataatgct    300
ttcggcggag ggaccaaggt ggaaatcaaa cgtacggtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t              651

<210> SEQ ID NO 30
<211> LENGTH: 217
<212> TYPE: PRT
<213> ORGANISM: Artificial
<220> FEATURE:
<223> OTHER INFORMATION: Humanized antibody sequence

<400> SEQUENCE: 30

Ala Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Glu
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Gly Tyr Ser Leu Arg Asn

```
                    85                  90                  95
Ile Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
            130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
            210                 215
```

<210> SEQ ID NO 31
<211> LENGTH: 18
<212> TYPE: PRT
<213> ORGANISM: Artificial
<220> FEATURE:
<223> OTHER INFORMATION: Secretion signal peptide

<400> SEQUENCE: 31

```
Met Arg Ser Leu Leu Ile Leu Val Leu Cys Phe Leu Pro Leu Ala Ala
1               5                   10                  15

Leu Gly
```

<210> SEQ ID NO 32
<211> LENGTH: 16
<212> TYPE: PRT
<213> ORGANISM: Artificial
<220> FEATURE:
<223> OTHER INFORMATION: Secretion signal peptide

<400> SEQUENCE: 32

```
Met Arg Leu Leu Leu Leu Leu Leu Leu Pro Leu Ala Ala Leu Gly
1               5                   10                  15
```

<210> SEQ ID NO 33
<211> LENGTH: 19
<212> TYPE: PRT
<213> ORGANISM: Artificial
<220> FEATURE:
<223> OTHER INFORMATION: Secretion signal peptide

<400> SEQUENCE: 33

```
Met Leu Leu Gln Ala Phe Leu Phe Leu Leu Ala Gly Phe Ala Ala Lys
1               5                   10                  15

Ile Ser Ala
```

<210> SEQ ID NO 34
<211> LENGTH: 35
<212> TYPE: PRT
<213> ORGANISM: Artificial
<220> FEATURE:
<223> OTHER INFORMATION: Secretion signal peptide

<400> SEQUENCE: 34

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Glu Gly Val Ser Leu
            20                  25                  30

Glu Lys Arg
        35

<210> SEQ ID NO 35
<211> LENGTH: 22
<212> TYPE: PRT
<213> ORGANISM: Artificial
<220> FEATURE:
<223> OTHER INFORMATION: Secretion signal peptide

<400> SEQUENCE: 35

Met Arg Phe Pro Ser Ile Phe Thr Ala Val Leu Phe Ala Ala Ser Ser
1               5                   10                  15

Ala Leu Ala Ala Pro Val
            20

<210> SEQ ID NO 36
<211> LENGTH: 27
<212> TYPE: PRT
<213> ORGANISM: Artificial
<220> FEATURE:
<223> OTHER INFORMATION: Secretion signal peptide

<400> SEQUENCE: 36

Met Arg Phe Pro Ser Ile Phe Thr Ala Val Leu Phe Ala Ala Ser Ser
1               5                   10                  15

Ala Leu Ala Ala Pro Val Ser Leu Glu Lys Arg
            20                  25

<210> SEQ ID NO 37
<211> LENGTH: 41
<212> TYPE: PRT
<213> ORGANISM: Artificial
<220> FEATURE:
<223> OTHER INFORMATION: Secretion signal peptide

<400> SEQUENCE: 37

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Glu Gly Val Ser Leu
            20                  25                  30

Glu Lys Arg Glu Ala Glu Ala Glu Ala
        35                  40

<210> SEQ ID NO 38
<211> LENGTH: 85
<212> TYPE: PRT
<213> ORGANISM: Artificial
<220> FEATURE:
<223> OTHER INFORMATION: Secretion signal peptide

<400> SEQUENCE: 38

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

```
Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg
                85

<210> SEQ ID NO 39
<211> LENGTH: 44
<212> TYPE: PRT
<213> ORGANISM: Artificial
<220> FEATURE:
<223> OTHER INFORMATION: Secretion signal peptide

<400> SEQUENCE: 39

Met Thr Lys Pro Thr Gln Val Leu Val Arg Ser Val Ser Ile Leu Phe
1               5                   10                  15

Phe Ile Thr Leu Leu His Leu Val Val Ala Leu Asn Asp Val Ala Gly
            20                  25                  30

Pro Ala Glu Thr Ala Pro Val Ser Leu Leu Pro Arg
        35                  40

<210> SEQ ID NO 40
<211> LENGTH: 22
<212> TYPE: PRT
<213> ORGANISM: Artificial
<220> FEATURE:
<223> OTHER INFORMATION: Secretion signal peptide

<400> SEQUENCE: 40

Met Phe Ser Pro Ile Leu Ser Leu Glu Ile Ile Leu Ala Leu Ala Thr
1               5                   10                  15

Leu Gln Ser Val Phe Ala
            20

<210> SEQ ID NO 41
<211> LENGTH: 22
<212> TYPE: PRT
<213> ORGANISM: Artificial
<220> FEATURE:
<223> OTHER INFORMATION: Secretion signal peptide

<400> SEQUENCE: 41

Met Gln Thr Leu Leu Val Ser Ser Leu Val Val Ser Leu Ala Ala Ala
1               5                   10                  15

Leu Pro His Tyr Ile Arg
            20

<210> SEQ ID NO 42
<211> LENGTH: 22
<212> TYPE: PRT
<213> ORGANISM: Artificial
<220> FEATURE:
<223> OTHER INFORMATION: Secretion signal peptide

<400> SEQUENCE: 42

Met Ile Phe Leu Lys Leu Ile Lys Ser Ile Val Ile Gly Leu Gly Leu
1               5                   10                  15

Val Ser Ala Ile Gln Ala
            20

<210> SEQ ID NO 43
<211> LENGTH: 24
```

```
<212> TYPE: PRT
<213> ORGANISM: Artificial
<220> FEATURE:
<223> OTHER INFORMATION: Secretion signal peptide

<400> SEQUENCE: 43

Met Lys Trp Val Thr Phe Ile Ser Leu Leu Phe Leu Phe Ser Ser Ala
1               5                   10                  15

Tyr Ser Arg Gly Val Phe Arg Arg
            20

<210> SEQ ID NO 44
<211> LENGTH: 18
<212> TYPE: PRT
<213> ORGANISM: Artificial
<220> FEATURE:
<223> OTHER INFORMATION: Secretion signal peptide

<400> SEQUENCE: 44

Met Lys Trp Val Thr Phe Ile Ser Leu Leu Phe Leu Phe Ser Ser Ala
1               5                   10                  15

Tyr Ser

<210> SEQ ID NO 45
<211> LENGTH: 24
<212> TYPE: PRT
<213> ORGANISM: Artificial
<220> FEATURE:
<223> OTHER INFORMATION: Secretion signal peptide

<400> SEQUENCE: 45

Met Ala Leu Trp Met Arg Leu Leu Pro Leu Leu Ala Leu Leu Ala Leu
1               5                   10                  15

Trp Gly Pro Asp Pro Ala Ala Ala
            20

<210> SEQ ID NO 46
<211> LENGTH: 24
<212> TYPE: PRT
<213> ORGANISM: Artificial
<220> FEATURE:
<223> OTHER INFORMATION: Secretion signal peptide

<400> SEQUENCE: 46

Met Lys Tyr Thr Ser Tyr Ile Leu Ala Phe Gln Leu Cys Ile Val Leu
1               5                   10                  15

Gly Ser Leu Gly Cys Asp Leu Pro
            20

<210> SEQ ID NO 47
<211> LENGTH: 26
<212> TYPE: PRT
<213> ORGANISM: Artificial
<220> FEATURE:
<223> OTHER INFORMATION: Secretion signal peptide

<400> SEQUENCE: 47

Met Ala Ala Asp Ser Gln Thr Pro Trp Leu Leu Thr Phe Ser Leu Leu
1               5                   10                  15

Cys Leu Leu Trp Pro Gln Glu Pro Gly Ala
            20                  25

<210> SEQ ID NO 48
<211> LENGTH: 27
```

```
<212> TYPE: PRT
<213> ORGANISM: Artificial
<220> FEATURE:
<223> OTHER INFORMATION: Secretion signal peptide

<400> SEQUENCE: 48

Met Lys Lys Asn Arg Met Met Met Ile Trp Ser Val Gly Val Val
1               5                   10                  15

Trp Met Leu Leu Leu Val Gly Gly Ser Tyr Gly
            20                  25

<210> SEQ ID NO 49
<211> LENGTH: 18
<212> TYPE: PRT
<213> ORGANISM: Artificial
<220> FEATURE:
<223> OTHER INFORMATION: Secretion signal peptide

<400> SEQUENCE: 49

Met Gln Lys Leu Ile Ile Phe Ala Leu Val Val Leu Cys Val Gly Ser
1               5                   10                  15

Glu Ala

<210> SEQ ID NO 50
<211> LENGTH: 18
<212> TYPE: PRT
<213> ORGANISM: Artificial
<220> FEATURE:
<223> OTHER INFORMATION: Secretion signal peptide

<400> SEQUENCE: 50

Met Lys Ala Leu Ile Val Leu Gly Leu Val Leu Leu Ser Val Thr Val
1               5                   10                  15

Gln Gly

<210> SEQ ID NO 51
<211> LENGTH: 20
<212> TYPE: PRT
<213> ORGANISM: Artificial
<220> FEATURE:
<223> OTHER INFORMATION: Secretion signal peptide

<400> SEQUENCE: 51

Met Val Asp Gly Val Met Ile Leu Pro Val Leu Ile Met Ile Ala Leu
1               5                   10                  15

Pro Ser Pro Ser
            20

<210> SEQ ID NO 52
<211> LENGTH: 19
<212> TYPE: PRT
<213> ORGANISM: Artificial
<220> FEATURE:
<223> OTHER INFORMATION: Secretion signal peptide

<400> SEQUENCE: 52

Met Gly Ala Ala Ala Lys Leu Ala Phe Ala Val Phe Leu Ile Ser Cys
1               5                   10                  15

Ser Ser Gly

<210> SEQ ID NO 53
<211> LENGTH: 31
<212> TYPE: PRT
<213> ORGANISM: Artificial
```

```
<220> FEATURE:
<223> OTHER INFORMATION: Secretion signal peptide

<400> SEQUENCE: 53

Met Leu Ser Leu Lys Pro Ser Trp Leu Thr Leu Ala Ala Leu Met Tyr
1               5                   10                  15

Ala Met Leu Leu Val Val Val Pro Phe Ala Lys Pro Val Arg Ala
                20                  25                  30

<210> SEQ ID NO 54
<211> LENGTH: 22
<212> TYPE: PRT
<213> ORGANISM: Artificial
<220> FEATURE:
<223> OTHER INFORMATION: Secretion signal peptide

<400> SEQUENCE: 54

Met Asp Met Arg Val Pro Ala Gln Leu Leu Gly Leu Leu Leu Leu Trp
1               5                   10                  15

Leu Pro Gly Ala Lys Cys
                20
```